United States Patent [19]

Naito et al.

[11] Patent Number: 5,648,372

[45] Date of Patent: Jul. 15, 1997

[54] ANTIFUNGAL AGENTS, AND COMPOSITIONS

[75] Inventors: Toshihiko Naito; Katsura Hata; Yumiko Kaku; Akihiko Tsuruoka; Itaru Tsukada; Manabu Yanagisawa; Toshio Toyosawa; Kazumasa Nara, all of Ibaraki, Japan

[73] Assignee: Eisai Co., Ltd., Tokyo, Japan

[21] Appl. No.: 382,158

[22] Filed: Feb. 1, 1995

[30] Foreign Application Priority Data

Feb. 7, 1994 [JP] Japan .................. 6-033268
Jul. 5, 1994 [JP] Japan .................. 6-174894
Aug. 10, 1994 [JP] Japan .................. 6-208203
Dec. 9, 1994 [JP] Japan .................. 6-306467

[51] Int. Cl.⁶ .................. A61K 31/44; A61K 31/41; C07D 417/06

[52] U.S. Cl. .................. 514/383; 548/205; 548/179; 548/235; 548/236; 548/266.4; 548/266.6; 548/252; 548/204; 546/194; 514/365; 514/367; 514/374; 514/381; 514/382; 514/342; 514/340

[58] Field of Search .................. 548/204, 205, 548/179, 235, 236, 266.4, 266.6, 252; 514/365, 367, 383, 374, 381, 340, 342, 382; 546/194

[56] References Cited

U.S. PATENT DOCUMENTS

| | | | |
|---|---|---|---|
| 4,657,920 | 4/1987 | Gajowski et al. | 514/365 |
| 4,935,049 | 6/1990 | Kramer et al. | 71/90 |
| 5,049,570 | 9/1991 | Batt et al. | 514/341 |

FOREIGN PATENT DOCUMENTS

| | | | |
|---|---|---|---|
| 313984 | 5/1989 | European Pat. Off. | |
| 3813841 | 12/1988 | Germany. | |
| 2024336 | 2/1992 | Spain | C07D 417/10 |
| 9217474 | 10/1992 | WIPO | C07D 413/06 |

OTHER PUBLICATIONS

Chemical Abstracts, vol. 117, No. 11, (1992) abstract No. 117:111617k.

Primary Examiner—Johann Richter
Assistant Examiner—Laura R. Cross
Attorney, Agent, or Firm—Wenderoth, Lind & Ponack

[57] ABSTRACT

A compound represented by the general formula:

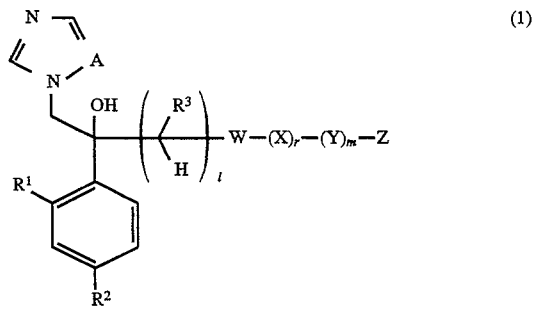

wherein $R^1$ and $R^2$ denote a halogen atom or hydrogen atom; $R^3$ means a hydrogen atom or lower alkyl group; l, r and m stand for 0 or 1; A is N or CH; W denotes an aromatic ring or a condensed ring thereof; X means another aromatic ring, an alkanediyl group, an alkenediyl group, or an alkynediyl group; Y stand for —S—, etc.; Z denotes a hydrogen atom, etc., and a salt thereof, and intermediates thereof or a salt thereof as well as processes for the preparation thereof, and pharmacetical composition suitable for use as an antifungal agent.

4 Claims, No Drawings

ANTIFUNGAL AGENTS, AND COMPOSITIONS

BACKGROUND OF THE INVENTION

1. Field of the Invention

The present invention relates to an antifungal agent. Particularly, the present invention relates to an antifungal agent useful for treatment for dermatomycosis, visceromycosis or the like. More particularly, the present invention relates to a derivative containing a 5-membered heterocyclic ring or a condensed ring thereof, and an acid-addition salt thereof, which are useful as antifungal agents. Further, the present invention relates to a preparation process of such derivative and acid-addition salt, and a pharmaceutical composition comprising the derivative and a pharmaceutically acceptable salt therefor.

Furthermore, the present invention relates to synthetic intermediates of azolic compound useful as an antifungal agent, and a process for the preparation thereof. Particularly, the present invention relates to synthetic intermediates useful for the preparation of antifungal agent effective to the remedy of the dermatomycosis, visceral micotic infection and the like, and a process for the preparation thereof.

2. Description of the Related Art

In the field of antifungal agents, amphoterin B or the like has heretofore been used, for example, in treatment for mycosis profundus. However, azole type synthetic antifungal agents have recently come to be developed. Even in these azole type agents, however, there has been an eager demand for development of a far excellent antifungal agent from the viewpoint of its effect for patients depressed in immune function.

For example, Japanese Patent Application Laid-Open (KOKAI) No. 70885/1982 discloses a tirazole compound as an azole type synthetic antifungal agent. Besides, Japanese Patent Application Laid-Open (KOKAI) No. 224689/1985 discloses a (1,2,4-triazol-1-yl)-methyl-carbinol derivative.

The present invention intends to provide an antifungal agent more effective than the conventional antifungal agents and intermeidates therefor.

SUMMARY OF THE INVENTION

The present inventors have carried out an extensive investigation. As a result, the following inventions have been completed.

I. A compound represented by the general formula:

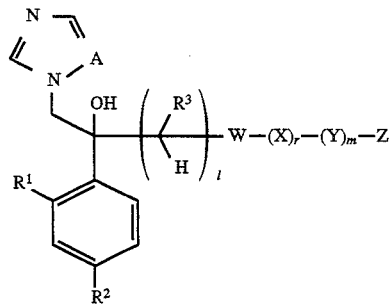

(1)

wherein $R^1$ and $R^2$ are identical with or different from each other and denote individually a halogen atom or hydrogen atom; $R^3$ means a hydrogen atom or lower alkyl group; l, r and m may be identical with or different from each other and stand individually for 0 or 1; A is N or CH; W denotes an aromatic ring or a condensed ring thereof which may have one or more hereto-atoms and may have one or more substituent groups, or W denotes an aromatic ring or a condensed ring thereof wherein a part or the whole of an aromatic ring or a condensed ring thereof which may have one or more hereto-atoms and may have one or more substituent groups is saturated, X means an aromatic ring which may have one or more substituent groups and may contain one or more hetero-atoms selected from N, S and O, an alkanediyl group which may have one or more substituent groups, an alkenediyl group which may have one or more substituent groups, or an alkynediyl group which may have one or more substituent group; Y stands for a group represented by —S—, >SO, >SO$_2$, >C=S, >C=O, —O—, >N—R$^6$, >C=N—OR$^6$ or —(CH$_2$)$_j$—, in which R$^6$ means a hydrogen atom or lower alkyl group, and j stands for an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenyl group which may have one or more substituent groups, phenoxy group which may have one or more substituent group, imidazolyl group which may have one or more substituent groups, triazolyl group which may have one or more substituent groups, tetrazolyl group which may have one or more substituent groups, or amino group which may have one or more substituent groups, except for the case where W is a thiazole ringe, $R^3$ is a methyl group, and Z is a hydrogen atom when l=1 and r=m=0, or a salt thereof.

II. A process for the preparation of optically active (2S, 3R)-3-(2,4-difluorophenyl)-3-hydroxy-2-methyl-4-(1H-1,2,4-triazol-1-yl)butyronitrile, which comprises reacting optically active (2R,3S)-2-(2,4-difluorophenyl)-3-methyl-2-(1H-1,2,4-triazol-1-yl)methyloxirane with diethylaluminum cyanide.

III. A process for the preparation of optically active (2S,3R)-3-(2,4-difluorophenyl)-3-hydroxy-2-methyl-4-(1H-1,2,4-triazol-1-yl)butyronitrile, which comprises reacting optically active (2R,3S)-2-(2,4-difluorophenyl)-3-methyl-2-(1H-1,2,4-triazol-1-yl)methyloxirane with ytterbium cyanide.

IV. A process for the stereoselective preparation of optically active (2S,3R)-3-(2,4-difluorophenyl)-3-hydroxyl-2-methyl-4-(1H-1,2,4-triazol-1-yl)butyronitorile, which comprises reacting optically active (2R,3S)-2-(2,4-difulorophenyl)-3-methyl-2-(1H,-1,2,4-triazol-1-yl) methyloxirane with acetonecyanohydrin.

V. A process for the preparation of a compound represented by the formula:

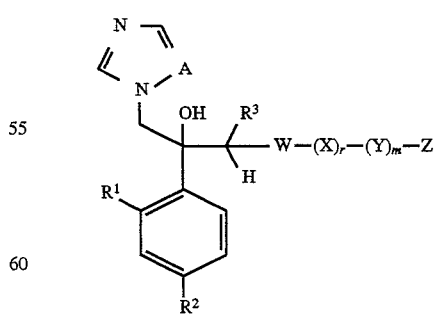

wherein W means a substituted thiazole ring, and A, $R^1$, $R^2$, $R^3$, X, Y, Z, r and m are as defined above or an acid-addition salt thereof, which comprises reacting a compound represented by the formula:

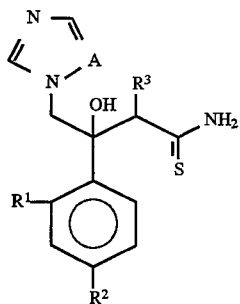

wherein A, R¹, R² and R³ are as defined above, with a compound represented by the formula:

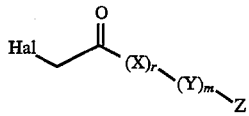

wherein Hal is Br or Cl, and X, Y, Z, r and m are as defined above.

VI. A process for the preparation of a compound represented by the formula:

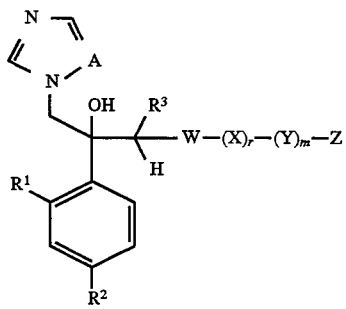

wherein A, R¹, R², R³, X, Y, Z, r and m are as defined above, and W means a substituted or unsubstituted, nitrogen-containing 5-membered heterocyclic ring or a condensed ring thereof, or an acid-addition salt thereof, which comprises reacting a compound represented by the formula:

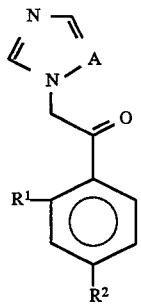

wherein A, R¹ and R² are as defined above with a compound represented by the formula:

wherein D is a group consisting of a substituted or unsubstituted, nitrogen-containing 5-membered heterocyclic ring or a condensed ring thereof, and Z is H or $CH_3$.

VII. A process for the preparation of a compound represented by the formula:

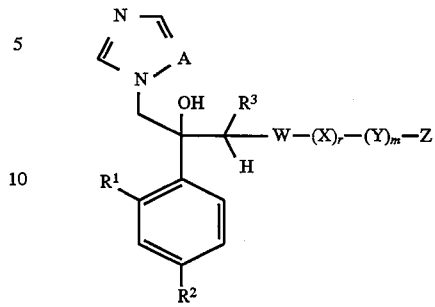

wherein W means a substituted or unsubstituted 5-membered heterocyclic ring or a condensed ring thereof, and A, R¹, R², R³, X, Y, Z, r and m are as defined above, or an acid-addition salt thereof, which comprises reacting a compound represented by the formula:

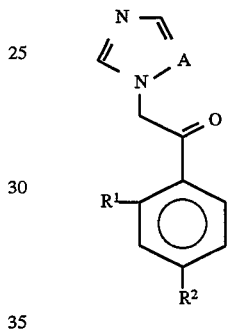

with a compound represented by the formula:

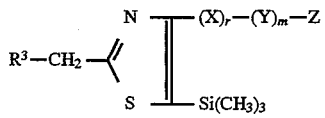

wherein R³, X, Y, Z, r and m are as defined above.

VIII. A process for the preparation of a compound represented by the formula:

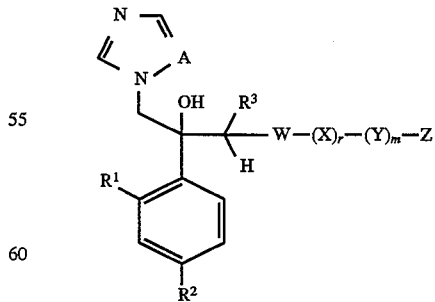

wherein A, R¹, R², R³, W, X, Y, Z, r and m are as defined above, or an acid-addition salt thereof, which comprises reacting a compound represented by the formula:

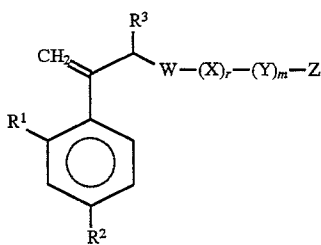

wherein A, R¹, R², R³, W, X, Y, Z, r and m are as defined above, with meta-chloroperbenzoic acid and then with sodium 1,2,4-triazole or sodium 1,3-imidazole.

IX. A pharmaceutical composition comprising a compound represented by the general formula (1):

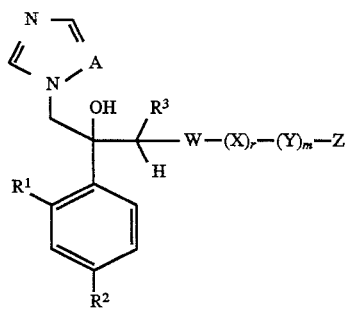 (1)

wherein R¹ and R² are identical with or different from each other and denote individually a halogen atom or hydrogen atom; R³ means a hydrogen atom or lower alkyl group; r and m may be identical with or different from each other and stand individually for 0 or 1; A is N or CH; W denotes an aromatic ring which may have one or more substituent groups and may contain one or more hetero-atoms selected from N, S and O, or a condensed ring thereof; X means an aromatic ring which may have one or more substituent groups and may contain one or more hetero-atoms selected from N, S and O, an alkanediyl group which may have one or more substituent groups, an alkenediyl group which may have one or more substituent groups, or an alkynediyl group which may have one or more substituent group; Y stands for a group represented by —S—, >SO, >SO$_2$, >C=S, >C=O, —O—, >N—R⁶, >C=N—OR⁶ or —(CH$_2$)$_j$—, in which R⁶ means a hydrogen atom or lower alkyl group, and j stands for an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenyl group which may have one or more substituent groups, phenoxy group which may have one or more substituent groups, imidazolyl group which may have one or more substituent groups, triazolyl group which may have one or more substituent groups, tetrazolyl group which may have one or more substituent groups, or amino group which may have one or more substituent groups, except for the case where W is a thiazole ringe, R³ is a methyl group, and Z is a hydrogen atom when r=m=0, or an acid-addition salt thereof and a pharmaceutically acceptable salt.

X. A process for the preparation of a derivative represented by the general formula:

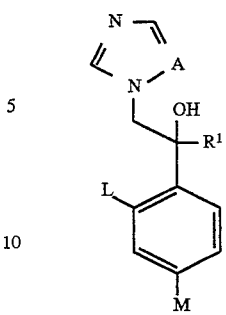

wherein
A is =CH— or =N—,
L and M are identical with or different from each other and denote individually a hydrogen atom or halogen atom, and R¹ means a 5-membered heterocyclic ring which may contain one or more other hetero-atoms in addition to a sulfur atom and has a substituent group; or a condensed ring of a 5-membered heterocyclic ring, which may contain one or more other hetero-atoms in addition to a sulfur atom and has a substituent group, with an aromatic ring which may contain one or more hetero-atoms and may have a substituent group; or a partly or entirely saturated condensed ring thereof, or an acid-addition salt thereof, which comprises, upon the preparation of the derivative or the acid-addition salt thereof, adding a 2-halo-acetophenone represented by the general formula:

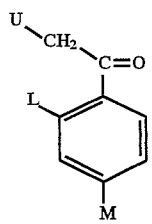

wherein U denotes a halogen atom, and L and M have the same meaning as defined above, to a compound containing a 5-membered heterocyclic ring or a condensed ring thereof or a partly or entirely saturated condensed ring thereof in the presence of an n-alkyllithium to react them, and then adding 1,2,4-triazole and sodium hydride to the resulting reaction product to react them.

XI. A process for the preparation of a derivative represented by the general formula:

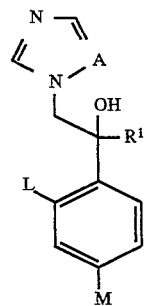

wherein
A is =CH— or =N—,
L and M are identical with or different from each other and denote individually a hydrogen atom or halogen atom, and R¹ means a 5-membered heterocyclic ring which may contain one or more other hetero-atoms in addition to a sulfur atom and has a substituent group; or a condensed ring of a 5-membered heterocyclic ring, which may contain one or more other hetero-atoms in addition to a sulfur atom and has a substituent group, with an aromatic ring which may contain one or more hetero-atoms and may have a substituent group; or a partly or entirely saturated condensed ring thereof, or an acid-addition salt thereof, which comprises, upon the preparation of the derivative or the acid-addition salt thereof, reacting its corresponding derivative containing a cyanophenyl-substituted 5-membered heterocyclic ring with sodium azide and triethylamine hydrochloride.

XII. A process for the preparation of a derivative represented by the general formula

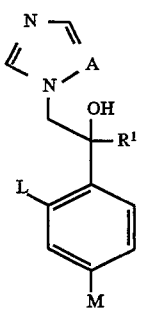

wherein

A is =CH— or =N—,

L and M are identical with or different from each other and denote individually a hydrogen atom or halogen atom, and R¹ means a 5-membered heterocyclic ring which may contain one or more other hetero-atoms in addition to a sulfur atom and has a substituent group; or a condensed ring of a 5-membered heterocyclic ring, which may contain one or more other hereto-atoms in addition to a sulfur atom and has a substituent group, with an aromatic ring which may contain one or more hetero-atoms and may have a substituent group; or a partly or entirely saturated condensed ring thereof, said derivatives being substituted by an alkyl group at a 3- or 4-position of a tetrazole ring, or an acid-addition salt thereof, which comprises, upon the preparation of the derivative or the acid-addition salt thereof, reacting its corresponding derivative containing a tetrazole.phenyl-substituted 5-membered heterocyclic ring with an alkyl halide.

XIII. A process for the preparation of a derivative represented by the general formula

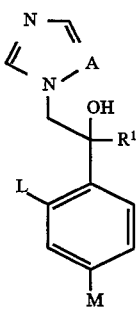

wherein

A is =CH— or =N—,

L and M are identical with or different from each other and denote individually a hydrogen atom or halogen atom, and R¹ means a 5-membered heterocyclic ring which may contain one or more other hetero-atoms in addition to a sulfur atom and has a substituent group; or a condensed ring of a 5-membered heterocyclic ring, which may contain one or more other hetero-atoms in addition to a sulfur atom and has a substituent group, with an aromatic ring which may contain one or more hetero-atoms and may have a substituent group; or a partly or entirely saturated condensed ring thereof, or an acid-addition salt thereof, which comprises, upon the preparation of the derivative or the acid-addition salt thereof, reacting its corresponding derivative containing a halophenyl-substituted 5-membered heterocyclic ring with 1,2,4-triazole and sodium hydride.

XIV. A process for the preparation of a derivative represented by the general formula

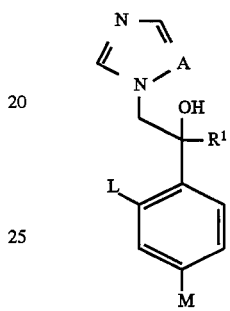

wherein

A is =CH— or =N—,

L and M are identical with or different from each other and denote individually a hydrogen atom or halogen atom, and R¹ means a 5-membered heterocyclic ring which may contain one or more other hetero-atoms in addition to a sulfur atom and has a substituent group; or a condensed ring of a 5-membered heterocyclic ring, which may contain one or more other hetero-atoms in addition to a sulfur atom and has a substituent group, with an aromatic ring which may contain one or more hetero-atoms and may have a substituent group; or a partly or entirely saturated condensed ring thereof, or an acid-addition salt thereof, which comprises, upon the preparation of the derivative or the acid-addition salt thereof, reacting its corresponding derivative containing a 1,2,4-triazol-1-yl)ethanol.

XV. A process for the preparation of a compound represented by the general formula:

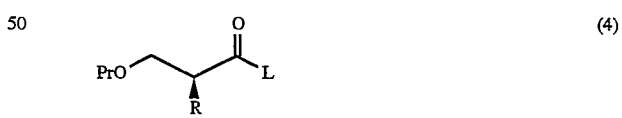

(4)

wherein R means a lower alkyl group, Pr denotes a protecting group for a hydroxyl group, and L stands for a leaving group, or a salt thereof, which comprises protecting the hydroxyl group of a compound represented by the general formula:

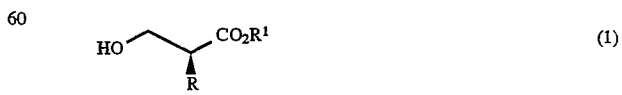

(1)

wherein R means the same group as defined above, and R¹ denotes a hydrogen atom or a protecting group for a carboxyl group, by a protecting group to form a compound represented by the general formula:

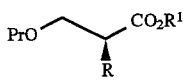

(2)

wherein R, R[1] and Pr each mean the same groups as defined above, then deblocking the protecting group for the carboxyl group of the compound represented by the formula (2) to form a compound represented by the general formula:

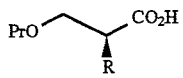

(3)

wherein R and Pr each mean the same groups as defined above, and further reacting the compound represented by the formula (3) with a compound represented by the formula: LH in which L means the same group as defined above.

XVI. A process for the preparation of a compound represented by the general formula:

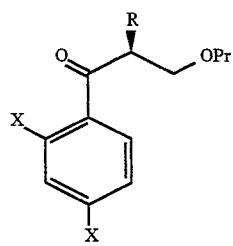

(7)

wherein R means a lower alkyl group, Xs are identical to or different from each other and denote individually a hydrogen or halogen atom, and Pr stands for a protecting group for a hydroxyl group, or a salt thereof, which comprises reacting a compound represented by the general formula:

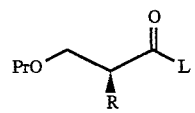

(5)

wherein R and Pr each mean the same groups as defined above, and L denotes a leaving group, with a compound represented by the general formula:

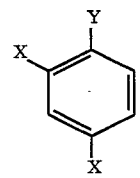

(6)

wherein Xs each mean the same groups as defined above, and Y means a chlorine, bromine or iodine atom, or a reactive derivative thereof.

XVII. A process for the preparation of a compound represented by the general formula:

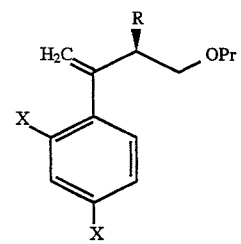

(9)

wherein R means a lower alkyl group, Xs are identical to or different from each other and denote individually a hydrogen or halogen atom, and Pr stands for a protecting group for a hydroxyl group, or a salt thereof, which comprises reacting a compound represented by the general formula:

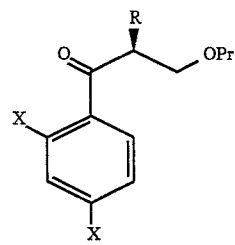

(8)

wherein R, Xs and Pr each mean the same groups as defined above, with triphenylphosphonium methylide derived from methyltriphenylphosphonium chloride, methyltriphenylphosphonium bromide or methyltriphenylphosphonium iodide, or with trimethylsilylmethylmagnesium chloride, trimethylsilylmethylmagnesium bromide or trimethylsilylmethyllithium.

XVIII. A process for the preparation of a compound represented by the general formula:

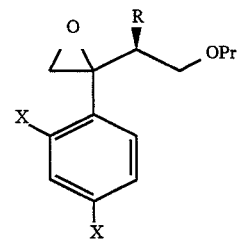

(11)

wherein R means a lower alkyl group, Xs are identical to or different from each other and denote individually a hydrogen or halogen atom, and Pr stands for a protecting group for a hydroxyl group, or a salt thereof, which comprises reacting a compound represented by the general formula:

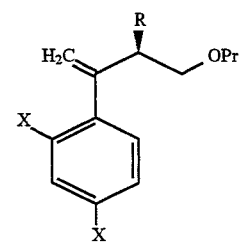

(10)

wherein R, Xs and Pr each mean the same groups as defined above, with a peroxy acid.

XIX. A process for the preparation of a compound represented by the general formula:

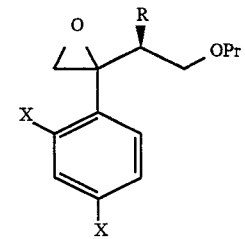

(13)

wherein R means a lower alkyl group, Xs are identical to or different from each other and denote individually a hydrogen or halogen atom, and Pr stands for a protecting group for a hydroxyl group, or a salt thereof, which comprises reacting a compound represented by the general formula:

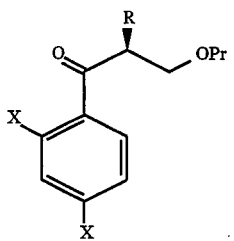

wherein R, Xs and Pr each mean the same groups as defined above, with chloromethyllithium formed from chloroiodomethane or bromochloromethane, or with dimethylsulfoxonium methylide, dimethylsulfonium methylide, diethyl-sulfoxonium methylide or diethylsulfonium methylide.

XX. A process for the preparation of a compound represented by the general formula:

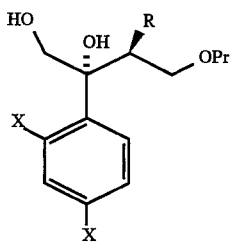

wherein R means a lower alkyl group, Xs are identical to or different from each other and denote individually a hydrogen or halogen atom, and Pr stands for a protecting group for a hydroxyl group, or a salt thereof, which comprises reacting a compound represented by the general formula:

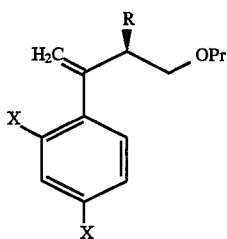

wherein R, Xs and Pr each mean the same groups as defined above, with an oxidizing agent.

XXI. A process for the preparation of a compound represented by the general formula:

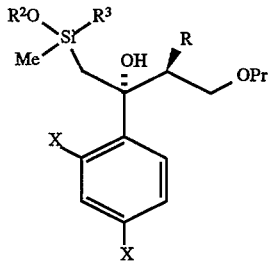

wherein R means a lower alkyl group, Xs are identical to or different from each other and denote individually a hydrogen or halogen atom, Pr stands for a protecting group for a hydroxyl group, $R^2$ means a lower alkyl group, and $R^3$ denotes a methyl or lower alkoxy group, or a salt thereof, which comprises reacting a compound represented by the general formula:

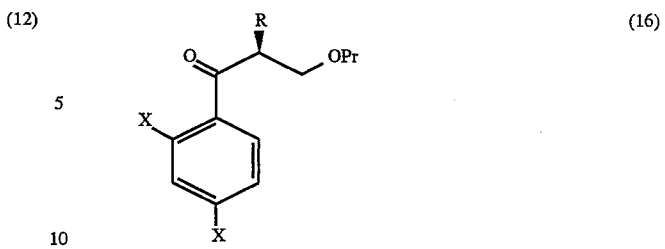

wherein R, Xs and Pr each mean the same groups as defined above, with an alkoxydimethylsilylmethylmagnesium halide or dialkoxymethylsilylmethylmagnesium halide.

XXII. A process for the preparation of a compound represented by the general formula:

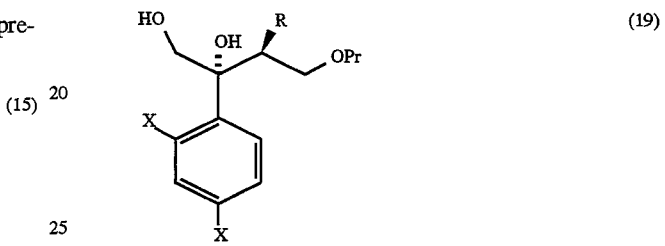

wherein R means a lower alkyl group, Xs are identical to or different from each other and denote individually a hydrogen or halogen atom, and Pr stands for a protecting group for a hydroxyl group, or a salt thereof, which comprises reacting a compound represented by the general formula:

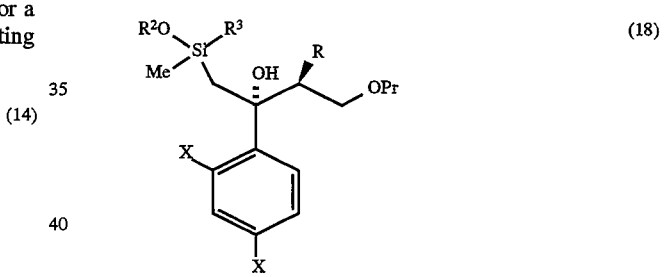

wherein R, Xs and Pr each mean the same groups as defined above, $R^2$ means a lower alkyl group, and $R^3$ denotes a methyl or lower alkoxy group, with a peroxy acid in the presence of a base.

XXIII. A process for the preparation of a compound represented by the general formula:

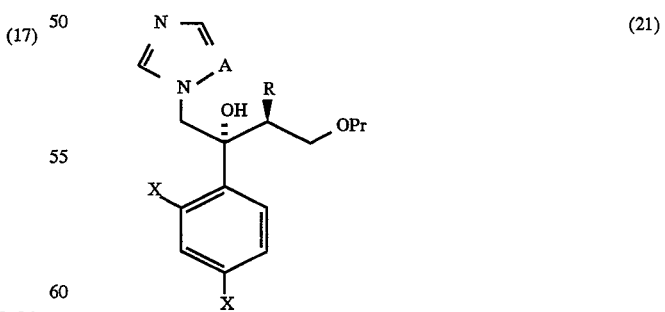

wherein R means a lower alkyl group, Xs are identical to or different from each other and denote individually a hydrogen or halogen atom, Pr stands for a protecting group for a hydroxyl group, and A means CH or a nitrogen atom, or a salt thereof, which comprises reacting a compound represented by the general formula:

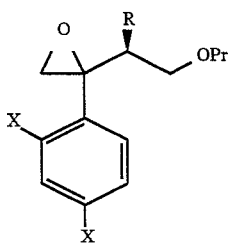
(20)

wherein R, Xs and Pr each mean the same groups as defined above, with 1,2,4-triazole or imidazole, or a salt thereof.

XXIV. A process for the preparation of a compound represented by the general formula:

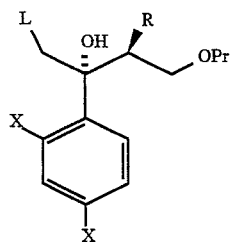
(23)

wherein R means a lower alkyl group, Xs are identical to or different from each other and denote individually a hydrogen or halogen atom, Pr stands for a protecting group for a hydroxyl group, and L means a leaving group, or a salt thereof, which comprises halogenating, alkylsulfonating or arylsulfonating a compound represented by the general formula:

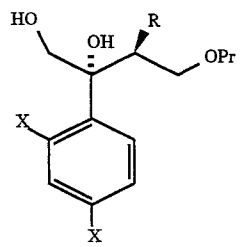
(22)

wherein R, Xs and Pr each mean the same groups as defined above.

XXV. A process for the preparation of a compound represented by the general formula:

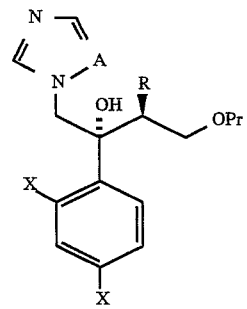
(25)

wherein R means a lower alkyl group, Xs are identical to or different from each other and denote individually a hydrogen or halogen atom, Pr stands for a protecting group for a hydroxyl group, and A means CH or a nitrogen atom, or a salt thereof, which comprises reacting a compound represented by the general formula:

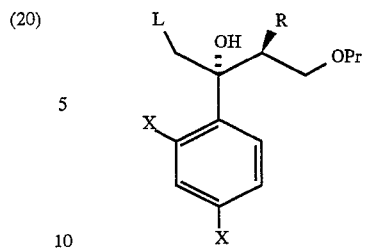
(24)

wherein R, Xs and Pr each mean the same groups as defined above, and L denotes a leaving group, with 1,2,4-triazole or imidazole, or a salt thereof.

XXVI. A process for the preparation of a compound represented by the general formula:

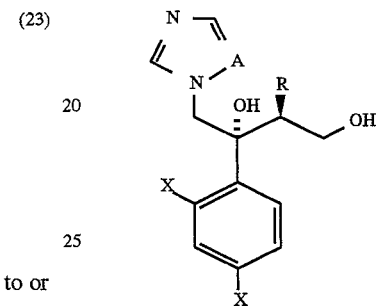
(27)

wherein R means a lower alkyl group, Xs are identical to or different from each other and denote individually a hydrogen or halogen atom, and A means CH or a nitrogen atom, or a salt thereof, which comprises deblocking Pr, which is a protecting group for a hydroxyl group, in a compound represented by the general formula:

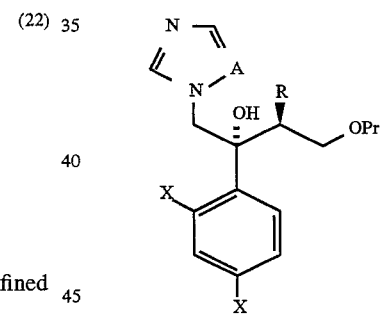
(26)

wherein R, Xs and A each mean the same groups as defined above, and Pr is a protecting group for a hydroxyl group.

XXVII. A process for the preparation of a compound represented by the general formula:

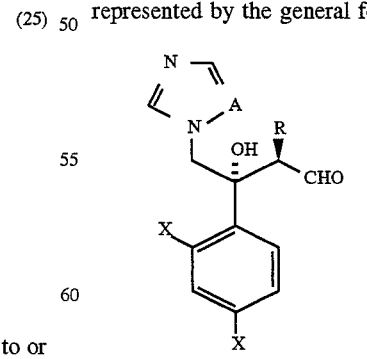
(29)

wherein R means a lower alkyl group, Xs are identical to or different from each other and denote individually a hydrogen or halogen atom, and A stands for CH or a nitrogen atom, or a salt thereof, which comprises reacting a compound represented by the general formula:

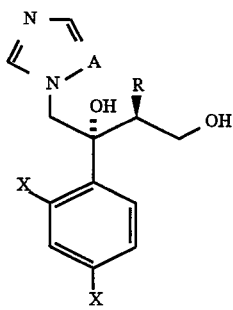

(28)

wherein R, Xs and A each mean the same groups as defined above, with an oxidizing agent.

XXVIII. A process for the preparation of a compound represented by the general formula:

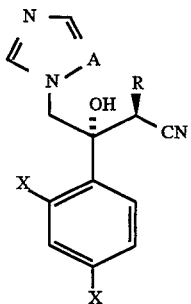

(31)

wherein R means a lower alkyl group, Xs are identical to or different from each other and denote individually a hydrogen or halogen atom, and A stands for CH or a nitrogen atom, or a salt thereof, which comprises reacting a compound represented by the general formula:

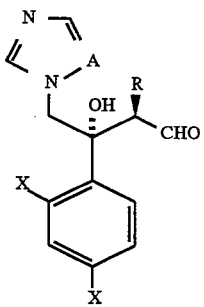

(30)

wherein R, Xs and A each mean the same groups as defined above, with a hydroxylamine derivative.

XXIX. A pharmaceutical composition comprising a compound represented by the general formula:

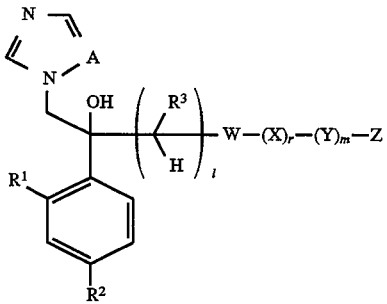

(1)

wherein $R^1$ and $R^2$ are identical with or different from each other and denote individually a halogen atom or hydrogen atom; $R^3$ means a hydrogen atom or lower alkyl group; l, r and m may be identical with or different from each other and stand individually for 0 or 1; A is N or CH; W denotes an aromatic ring or a condensed ring thereof which may have one or more hetero-atoms and may have one or more substituent groups, or W denotes an aromatic ring or a condensed ring thereof wherein a part or the whole of an aromatic ring or a condensed ring thereof which may have one or more hetero-atoms and may have one or more substituent groups is saturated, X means an aromatic ring which may have one or more substituent groups and may contain one or more hetero-atoms selected from N, S and O, an alkanediyl group which may have one or more substituent groups, an alkenediyl group which may have one or more substituent groups, or an alkynediyl group which may have one or more substituent group; Y stands for a group represented by —S—, >SO, >SO$_2$, >C=S, >C=O, —O—, >N—$R^6$, >C=N—$OR^6$ or —(CH$_2$)$_j$—, in which $R^6$ means a hydrogen atom or lower alkyl group, and j stands for an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenyl group which may have one or more substituent groups, phenoxy group which may have one or more substituent group, imidazolyl group which may have one or more substituent groups, triazolyl group which may have one or more substituent groups, tetrazolyl group which may have one or more substituent groups, or amino group which may have one or more substituent groups, except for the case where W is a thiazole ringe, $R^3$ is a methyl group, and Z is a hydrogen atom when l=1 and r=m=0, or a salt thereof and a pharmaceutically acceptable salt.

DETAILED DESCRIPTION OF THE INVENTION AND PREFERRED EMBODIMENTS

The present invention is to provide a derivative represented by the general formula (I)

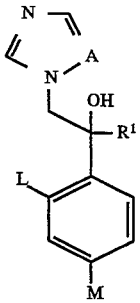

wherein
A is =CH— or =N—,
L and M are identical with or different from each other and denote individually a hydrogen atom or halogen atom, and
$R^1$ means a 5-membered heterocyclic ring which may contain one or more other hetero-atoms in addition to a sulfur atom and has a substituent group; or a condensed ring of a 5-membered heterocyclic ring, which may contain one or more other hetero-atoms in addition to a sulfur atom and has a substituent group, with an aromatic ring which may contain one or more hereto-atoms and may have a substituent group; or a partly or entirely saturated condensed ring thereof, or an acid-addition salt thereof having excellent antifungal properties.

The derivatives according to the present invention can be prepared through various synthetic routes. Some of them are exemplified below.

Process A

2-Chloro-2',4'-difluoroacetophenone is added to 4-(2,4-difluorophenyl)thiazole in the presence of n-butyllithium. After subjecting the reaction product to a post treatment, 1,2,4-triazole and sodium hydride are added thereto to obtain 1-(2,4-difluorophenyl)-1-(4-(2,4-difluorophenyl) thiazol-2-yl)-2-(1H-1,2,4-triazol-1-yl)-ethanol.

Process B (1) 2-Chloro-2',4'-difluoroacetophenone is added to 6-cyanobenzothiazole in the presence of n-butyllithium to form 1-(2,4-difluorophenyl)-1-(6-cyanobenzothiazol-2-yl)-2-chloroethanol.

(2) 1,2,4-Triazole is added to a suspension of sodium hydride in dimethylformamide. To this suspension, 1-(2,4-difluorophenyl)-1-(6-cyanobenzothiazol-2-yl)-2-chloroethanol formed in the step (1) is added to react them, thereby obtaining 1-(2,4-difluorophenyl)-1-(6-cyanobenzothiazol-2-yl)-2-(1H-1,2,4-triazol-1-yl)ethanol.

Process C 1-(2,4-Difluorophenyl)-1-(4-(4-cyanophenyl)thiazol-2-yl)-2-(1H-1,2,4-triazol-1-yl)ethanol is reacted with sodium azide and triethylamine hydrochloride to obtain 1-(2,4-difluorophenyl)-1-(4-[(4-(5-tetrazole)phenyl)-thiazol]-2-yl)-2-(1H-1,2,4-triazol-1-yl)ethanol.

Process D

Methyl iodide is reacted with 1-(2,4-difluorophenyl)-1-{4-[(4-(5-tetrazole)-phenyl)-thiazol]-2-yl}-2-(1H-1,2,4-triazol-1-yl)ethanol obtained in the above-described Process C to obtain two isomers in which a methyl group has been substituted at a 3- or 4-position of the tetrazole ring thereof.

Process E 1-(2,4-Difluorophenyl)-1-(2-(4-fluorophenyl)thiazol-5-yl)-2-(1H-1,2,4-triazol-1-yl)ethanol is reacted with 1,2,4-triazole and sodium hydride to obtain 1-(2,4-difluorophenyl)-1-{2-[(4-(1-1H-1,2,4-triazole)phenyl)-thiazol]-5-yl}-2-(1H-1,2,4-triazol-1-yl)ethanol.

Process F 1-(2,4-Difluorophenyl)-1-(6-thiocarbamoylbenzothiazol-2-yl)-2-(1H-1,2,4-triazol-yl)ethanol is reacted with sodium hydrogencarbonate and bromoacetone to obtain 1-(2,4-difluorophenyl)-1-(6-(3-methylthiazol-1-yl)-benzothiazol-2-yl)-2-(1H-1,2,4-triazol-1-yl)ethanol.

Process G 1-(2,4-Difluorophenyl)-1-(6-cyanobenzothiazol-2-yl)-2-(1H-1,2,4-triazol-1-yl)ethanol and triethylamine are dissolved in dimethylformamide. Into the resultant solution, hydrogen sulfide gas is introduced to react them, thereby obtaining 1-(2,4-difluorophenyl)-1-(6-thiocarbamoylbenzothiazol-2-yl)-2-(1H-1,2,4-triazol-1-yl) ethanol.

Process H 1-(2,4-Difluorophenyl)-1-(6-thiocarbamoylbenzothiazol-2-yl)-2-(1H-1,2,4-triazol-1-yl)ethanol is reacted with bromoacetaldehyde dimethylacetal to obtain 1-(2,4-difluorophenyl)-1-(6-thiazol-1-yl)-benzothiazol-2-yl-2-(1 1H-1,2,4-triazol-1-yl)ethanol.

Process I (1) 1-(2,4-Difluorophenyl)-1-(4-thiocarbamoylthiophenl-2-yl)-2-(1H-1,2,4-triazol-1-yl)ethanol is reacted with α-bromoethylpyruvic acid to form 1-(2,4-difluorophenyl)-1-(4-(4-ethoxycarbonylthiazol-2-yl)-thiophen-2-yl)-2-(1H-1,2,4-triazol-1-yl)ethanol (A).

(2) The thus-obtained compound (A) is dissolved in a saturated methanol solution of ammonia, and the resultant solution is left to stand, thereby reacting the compound and ammonia to obtain 1-(2,4-difluorophenyl)-1-(4-(4-carbamoylthiazol-2-yl)-thiophen-2-yl)-2-(1H-1,2,4-triazol-1-yl)ethanol (B).

Process J

The compound (B) obtained in the step (2) of the above-described Process I is dissolved in pyridine and reacted with phosphorus oxychloride to obtain 1-(2,4-difluorophenyl)-1-(4-(4-cyanothiazol-2-yl)-thiophen-2 yl)-2-(1H-1,2,4-triazol-1-yl)ethanol.

As examples of solvents usable in the present invention, may be mentioned lower alcohols such as methanol, ethanol, propanol and butanol; polyhydric alcohols such as ethylene glycol; ketones such as acetone, methyl ethyl ketone, diethyl ketone and cyclohexanone; ethers such as diethyl ether, isopropyl ether, tetrahydrofuran, dioxane, 2-methoxyethanol and 1,2-dimethoxyethane; nitriles such as acetonitrile and propionitrile; esters such as methyl acetate, ethyl acetate, isopropyl acetate, butyl acetate and diethyl phthalate; halogenated hydrocarbons such as dichloromethane, chloroform, carbon tetrachloride, 1,2-dichloroethane, trichloroethylene and tetrachloroethylene; aromatics such as benzene, toluene, xylene, monochlorobenzene, nitrobenzene, indene, pyridine, quinoline, collidine and phenol; hydrocarbons such as pentane, cyclohexane, hexane, heptane, octane, isooctane, petroleum benzin and petroleum ether; amines such as ethanolamine, diethylamine, triethylamine, pyrrolidine, piperidine, piperazine, morpholine, aniline, dimethylaniline, benzylamine and toluidine; amides such as formamide, N-methylpyrrolidone, N,N-dimethylimidazolone, N,N-dimethylacetamide and N,N-dimethylformamide; phosphoric amides such as hexamethylphosphoric triamide and hexamethylphosphorous triamide; organic acids such as formic acid, acetic acid, difluoroacetic acid, trifluoroacetic acid and chloroacetic acid; sulfoxides such as dimethyl sulfoxide; carbon sulfides such as carbon disulfide; water; and others solvents generally used. These solvents may be simple solvent or mixed solvents of two or more solvents thereof. No particular limitation is imposed on the mixing ratio of the mixed solvents.

As the pharmaceutically acceptable salts for the derivatives or the acid-addition salts thereof according to the present invention, may be mentioned the following salts.

Namely, as examples of inorganic salts, may be mentioned alkali metal salts such as sodium salts and potassium salts; ammonium salts; tetraethylammonium salts; quaternary ammonium salts such as betaine salts; alkaline earth metal salts such as calcium salts and magnesium salts; and inorganic acid salts such as hydrochlorides; hydrobromates, hydriodates, sulfates, carbonates and hydrogencarbonates.

Besides, as examples of organic salts, may be mentioned organic carboxylates such as acetates, maleates, lactates and tartarate; organic sulfonates such as methanesulfonates, hydroxymethanesulfonates, hydroxyethanesulfonates, taurine salts, benzenesulfonates and toluensulfonates; amino acid salts such as arginine salts, lysine salts, serine salts, aspartates, glutamates and glycinates; amine salts such as trimethylamine salts, triethylamine salts, pyridine salts, procaine salts, picoline salts, dicyclohexylamine salts, N,N-dibenzylethylenediamine salts, N-methylglucamine salts, diethanolamine salts, triethanolamine salts, tris (hydroxymethylamino)methane salts and phenetylbenzylamine salts.

Further the present invention is to provide a compound represented by the general formula (I)

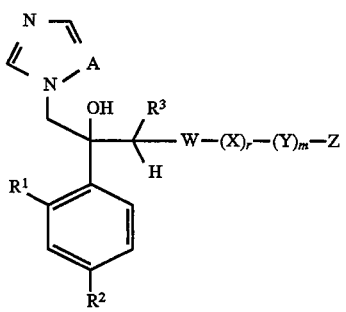

wherein $R^1$ and $R^2$ are identical with or different from each other and denote individually a halogen atom or hydrogen atom; $R^3$ means a hydrogen atom or lower alkyl group; r and m may be identical with or different from each other and stand individually for 0 or 1; A is N or CH; W denotes an aromatic ring which may have one or more substituent groups and may contain one or more hetero-atoms selected from N, S and O, or a condensed ring thereof; X means an aromatic ring which may have one or more substituent groups and may contain one or more hetero-atoms selected from N, S and O, an alkanediyl group which may have one or more substituent groups, an alkenediyl group which may have one or more substituent groups, or an alkynediyl group which may have one or more substituent group; Y stands for a group represented by —S—, >SO, >SO$_2$, >C=S, >C=O, —O—, >N—R$^6$, >C=N—OR$^6$ or —(CH$_2$)$_j$—, in which R$^6$ means a hydrogen atom or lower alkyl group, and j stands for an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenyl group which may have one or more substituent groups, phenoxy group which may have one or more substituent group, imidazolyl group which may have one or more substituent group, triazolyl group which may have one or more substituent group, tetrazolyl group which may have one or more substituent group, or amino group which may have one or more substituent group, except for the case where W is a thiazole ring, $R^3$ is a methyl group, and Z is a hydrogen atom when r=m=0, or an acid-addition salt thereof having excellent antifungal properties.

The compounds according to the present invention can be prepared through various synthetic routes. Some of them are exemplified below.

Route I

A compound of the formula:

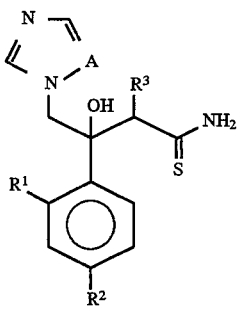

wherein A, $R^1$, $R^2$ and $R^3$ are as defined above, is reacted with a compound of the formula:

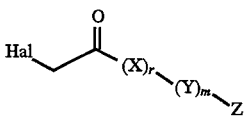

wherein Hal is Br or Cl, and X, Y, Z, r and m are as defined above, thereby obtaining a compound represented by the formula:

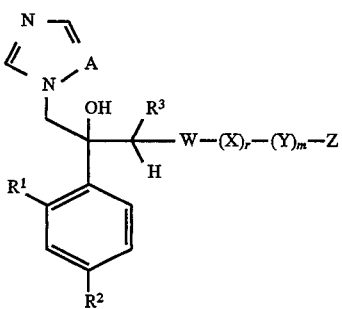

wherein W is a group consisting of a substituted azole, and A, $R^1$, $R^2$, $R^3$, X, Y, Z, r and m are as defined above.

Route II

A compound of the formula:

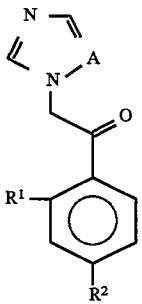

wherein A, $R^1$ and $R^2$ are as defined above, is reacted with a compound of the formula:

wherein D is a group consisting of a substituted or unsubstituted, nitrogen-containing 5-membered heterocyclic ring or a condensed ring thereof, and Z is H or CH₃, thereby obtaining a compound represented by the formula:

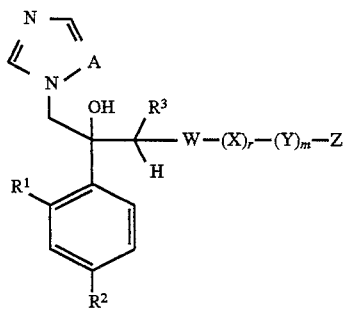

wherein W is a substituted or unsubstituted, nitrogen-containing 5-membered heterocyclic ring or a condensed ring thereof, and A, R¹, R², R³, X, Y, Z, r and m are as defined above.

Route III

A compound of the formula:

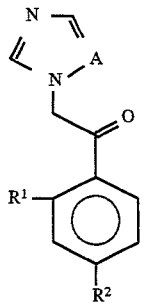

wherein A, R¹ and R² are as defined above, is reacted with a compound of the formula:

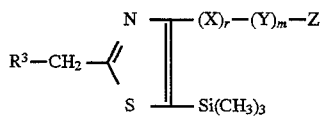

wherein R³, X, Y, Z, r and m are as defined above, thereby obtaining a compound represented by the formula:

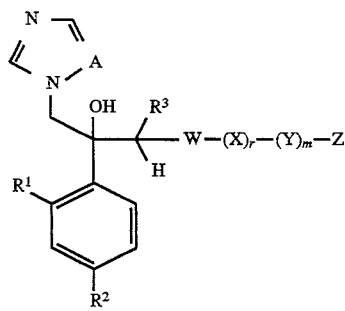

wherein W is a group consisting of a substituted or unsubstituted 5-membered heterocyclic ring or a condensed ring thereof, and A, R¹, R², R³, X, Y, Z, r and m are as defined above.

Route IV

A compound of the formula:

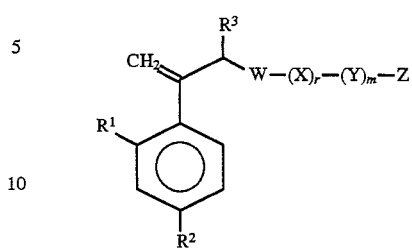

wherein R¹, R², R³, W, X, Y, Z, r and m are as defined above, is reacted with meta-chlorperbenzoic acid and then with sodium 1,2,4-triazole or sodium 1,3-imidazole, thereby obtaining a compound represented by the formula:

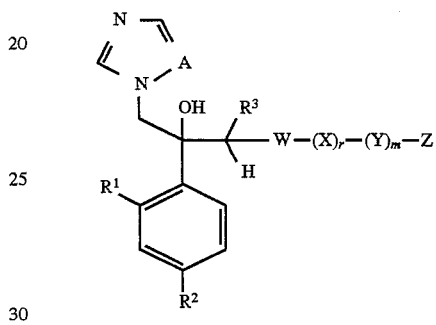

wherein A, R¹, R², R³, W, X, Y, Z, r and m are as defined above.

As an acid forming the acid-addition salt of the compound according to the present invention, may be used usual inorganic acids such as hydrochloric acid and sulfuric acid, and organic acids such as acetic acid and citric acid. Preferred acids are hydrochloric acid and acetic acid.

As examples of solvents usable in the present invention, may be mentioned lower alcohols such as methanol, ethanol, propanol and butanol; polyhydric alcohols such as ethylene glycol; ketones such as acetone, methyl ethyl ketone, diethyl ketone and cyclohexanone; ethers such as diethyl ether, isopropyl ether, tetrahydrofuran, dioxane, 2-methoxyethanol and 1,2-dimethoxyethane; nitriles such as acetonitrile and propionitrile; esters such as methyl acetate, ethyl acetate, isopropyl acetate, butyl acetate and diethyl phthalate; halogenated hydrocarbons such as dichloromethane, chloroform, carbon tetrachloride, 1,2-dichloroethane, trichloroethylene and tetrachloroethylene; aromatics such as benzene, toluene, xylene, monochlorobenzene, nitrobenzene, indene, pyridine, quinoline, collidine and phenol; hydrocarbons such as pentane, cyclohexane, hexane, heptane, octane, isooctane, petroleum benzin and petroleum ether; amines such as ethanolamine, diethylamine, triethylamine, pyrrolidine, piperidine, piperazine, morpholine, aniline, dimethylaniline, benzylamine and toluidine; amides such as formamide, N-methylpyrrolidone, N,N-dimethylimidazolone, N,N-dimethylacetamide and N,N-dimethylformamide; phosphoric amides such as hexamethylphosphoric triamide and hexamethylphosphorous triamide; organic acids such as formic acid, acetic acid, difluoroacetic acid, trifluoroacetic acid and chloroacetic acid; sulfoxides such as dimethyl sulfoxide; carbon sulfides such as carbon disulfide; water; and others solvents generally used. These solvents may be simple solvents or mixed solvents of two or more solvents thereof. No particular limitation is imposed on the mixing ratio of the mixed solvents.

As the pharmaceutically acceptable salts for the compounds or the acid-addition salts thereof according to the present invention, may be exemplified the following salts.

Namely, as examples of inorganic salts, may be mentioned alkali metal salts such as sodium salts and potassium salts; ammonium salts; tetraethylammonium salts; quaternary ammonium salts such as betaine salts; alkaline earth metal salts such as calcium salts and magnesium salts; and inorganic acid salts such as hydrochlorides; hydrobromates, hydriodates, sulfates, carbonates and hydrogencarbonates.

Besides, as examples of organic salts, may be mentioned organic carboxylates such as acetates, maleates, lactates and succinates; organic sulfonates such as methanesulfonates, hydroxymethanesulfonates, hydroxyethanesulfonates, taurine salts, benzenesulfonates and toluenesulfonates; amino acid salts such as arginine salts, lysine salts, serine salts, aspartates, glutamates and glycinates; and amine salts such as trimethylamine salts, triethylamine salts, pyridine salts, procaine salts, picoline salts, dicyclohexylamine salts, N,N-dibenzylethylenediamine salts, N-methylglucamine salts, diethanolamine salts, triethanolamine salts, tris (hydroxymethylamino)methane salts and phenetylbenzylamine salts.

Furthermore, the present invention is to provide a process for the preparation of a compound represented by the general formula:

wherein R means a lower alkyl group, Pr denotes a protecting group for a hydroxyl group and L stands for a leaving group, or salt thereof, which comprises protecting the hydroxyl group of a compound represented by the general formula:

wherein R means the same group as defined above, and $R^1$ denotes a hydrogen atom or a protecting group for carboxyl group, by a protecting group to form a compound represented by the general formula:

wherein R, $R^1$ and Pr have the same groups as defined above respectively, deblocking the protecting group for carboxyl group in the formula (2) to form a compound represetned by the formula:

wherein R and Pr have the same groups as defined above respectively, and reacting this compound of the formula (3) with a compound represented by the formula: LH, wherein L represents a leaving group;

a process for the preparation of compounds represented by the general formula:

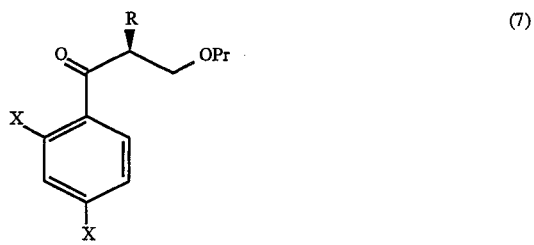

wherein R means a lower alkyl group, Xs are identical to or different from each other and denotes individually a hydrogen atom or a halogen atom, and Pr stands for a protecting group for a hydroxyl group, or a salt thereof, which comprises reacting a compound represented by the general formula:

wherein R and Pr have the same meanigs as defined above, and L represents a leaving group, with a compound represented by the general formula:

wherein Xs have the same groups as defined above, and Y represents chlorine atom, bromine atom or iodine atom respectively, or a reactive derivative thereof;

a process for the preparation of compounds represented by the general formula:

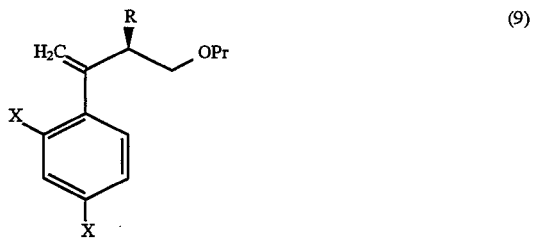

wherein R means a lower alkyl group, Xs are identical to or different from each other and denote hydrogen atom or a halogen atom, and Pr stands for a protecting group for hydroxyl group, respectively, or salt thereof, which comprises reacting a compound represented by the general formaula:

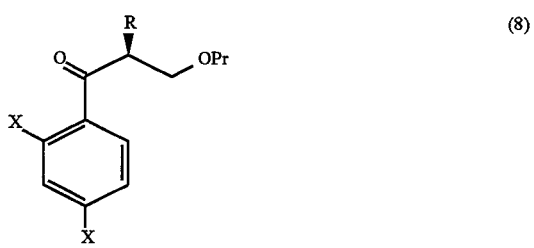

wherein R, X and Pr have the same groups as defined above with triphenylphsphonium methylide derived from methyltriphenylphosponium chloride, methyltriphenylphsphonium bromide or methyltriphenylphsphonium iodide, or with trimethylsilylmethyl magnesium chloride, trimethylsilylmethyl magnesium bromide or trimethylsilylmethyl lithium;

a process for the preparation of compounds represented by the general formula:

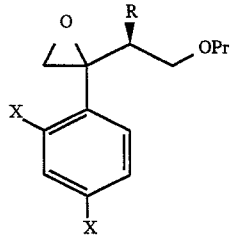
(11)

wherein R means a lower alkyl group, Xs are identical to or different from each other and denote hydrogen atom or a halogen atom, and Pr stands for a protecting group for hydroxyl group, respectively or salts thereof, which comprises reacting a compound represented by the general formula:

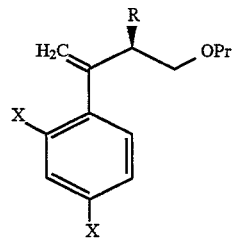
(10)

wherein R, X and Pr have the same groups as defined above, with a peroxyacid;

a process for the preparation of compounds represented by the general formula:

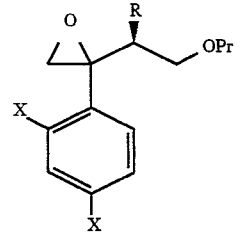
(13)

wherein R means a lower alkyl group, Xs are identical to or different from each other and denote hydrogen atom or a halogen atom, and Pr stands for a protecting group for hydroxyl group, respectively or salts thereof, which comprises reacting a compound represented by the general formula:

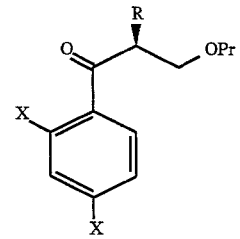
(12)

wherein R, X and Pr have the same groups as defined above with chloromethyl lithium produced from chloroiodomethane or bromoiodomethane, or dimethylsulfoxonium methylide or dimethylsulfonium methylide;

a process for the preparation of compounds represented by the general formula:

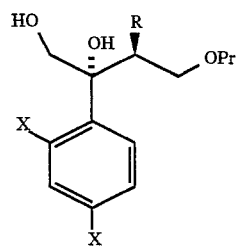
(15)

wherein R means a lower alkyl group, Xs are identical to or different from each other and denote hydrogen atom, or a halogen atom, and Pr stands for a protecting group for hydroxyl group, respectively, and salts thereof, which comprises reacting a compound represented by the general formula:

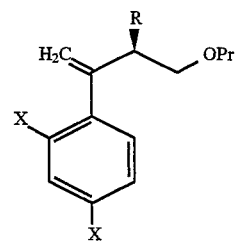
(14)

wherein R, X and Pr have the same groups as defined above respectively, with an oxidizing agent;

a process for the preparation of compounds represented by the general formula:

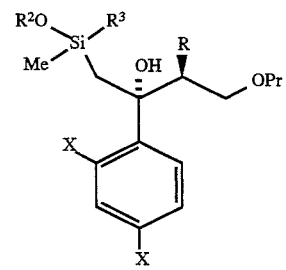
(17)

wherein R means a lower alkyl group, Xs are identical to or different from each other and denote hydrogen atom or a halogen atom, Pr stands for a protecting group for hydroxyl group, $R^2$ represents a lower alkyl group and $R^3$ represents methyl group or a lower alkoxy group respectively, and salts thereof, which comprises reacting a compound represented by the general formula:

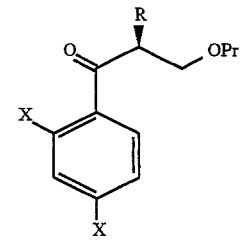
(16)

wherein R, X and Pr have the same groups as defined above with an alkoxydimethylsilylmethyl magnesium halide or a dialkoxymethylsilylmethyl magnesium halide;

a process for the preparation of compounds repreednt by the general formula:

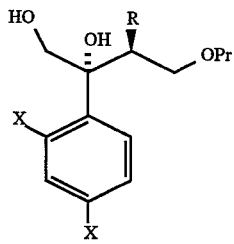
(19)

wherein R means a lower alkyl group, Xs are identical to or different from each other and denote hydrogen atom or a halogen atom, Pr stands for a protecting group for hydroxyl group, respectively, or salts thereof, which comprises reacting a compound represented by the general formula:

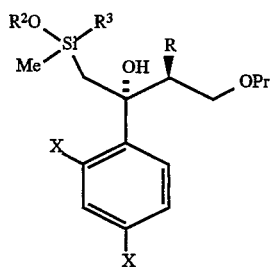
(18)

wherein R, X and Pr have the same groups as defined above, $R^2$ represents a lower alkyl group, and $R^3$ represents methyl group or a lower alkoxy group with peroxy acid in the presence of a base;

a process for the preparation of a compound represented by the formula:

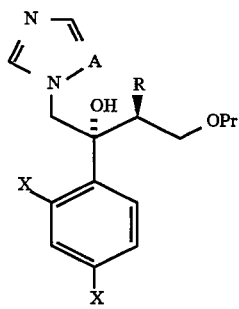
(21)

wherein R means a lower alkyl group, Xs are identical to or different from each other and denote hydrogen atom or a halogen atom, Pr stands for a protecting group for hydroxyl group and A stands for CH or a nitrogen atom, respectively and salts thereof, which comprises reacting a compound represented by the general formula:

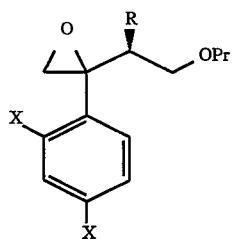
(20)

wherein R, X and Pr have the same groups as defined above with 1,2,4-triazole or imidazole or a salt thereof;

a process for the preparation of compounds represented by the general formula:

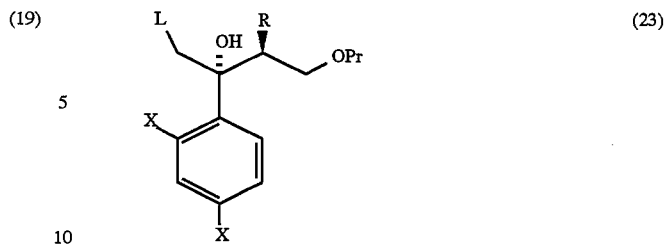
(23)

wherein R means a lower alkyl group, Xs are identical to or different from each other and denote hydrogen atom or a halogen atom, Pr stands for a protecting group for hydroxyl group, and L means a leaving group respectively, and salts thereof, which comprises halogenating, alkylsulfonating or arylsulfonating a compound represent by the general formula:

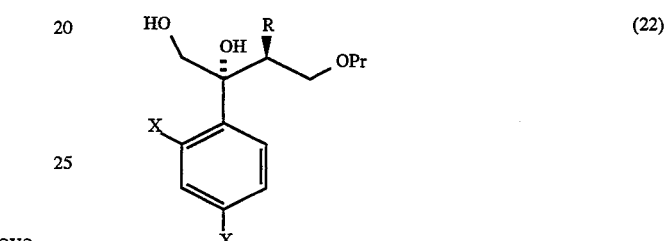
(22)

wherein R, X and Pr have the same groups as defined above;

a process for the preparation of compounds represented by the general formula:

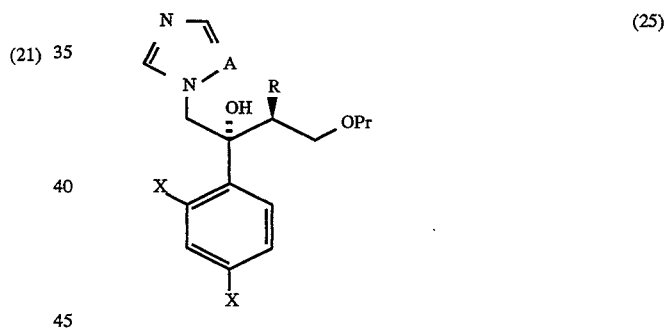
(25)

wherein R means a lower alkyl group, Xs are identical to or different from each other and denote hydrogen atom or a halogen atom, Pr stands for a protecting group for hydroxyl group, and A stands for CH or a nitrogen atom, respectively, or salts thereof, which comprises reacting a compound represented by the formula:

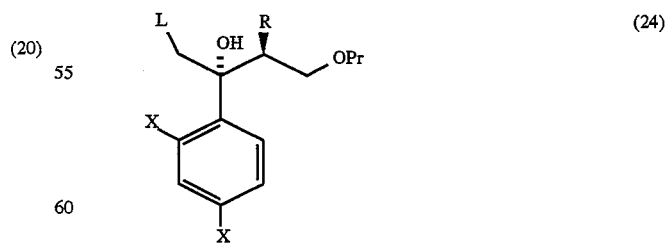
(24)

wherein R, X and Pr have the same groups as defined above and L stands for a leaving group with 1,2,4-triazole or imidazole, or a salt thereof;

a process for the preparation of compounds represented by the general formula:

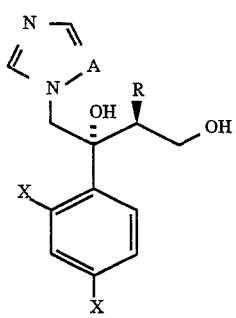

(27)

wherein R means a lower alkyl group, Xs are identical to or different from each other and denote hydrogen atom or a halogen atom, Pr denotes a protecting group for hydroxyl group, and A stands for CH or a nitrogen group, respectively, or salts thereof, which comprises deblocking Pr which is a protecting group for hydroxyl group on a compound represented by the general formula:

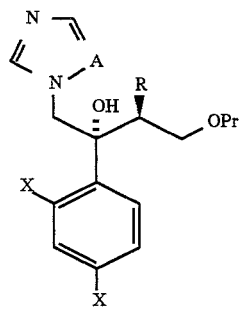

(26)

wherein R, X, Pr and A have the same groups as defined, above respectively, or salts thereof;

a process for the preparation of compounds represented by the general formula:

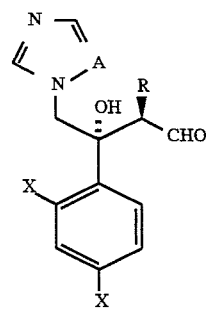

(29)

wherein R means a lower alkyl group, Xs are identical to or different from each other and denote hydrogen atom or a halogen atom, and A stands for CH or a nitrogen atom, respectively, or salts thereof, which comprises reacting a compound represented by the general formula:

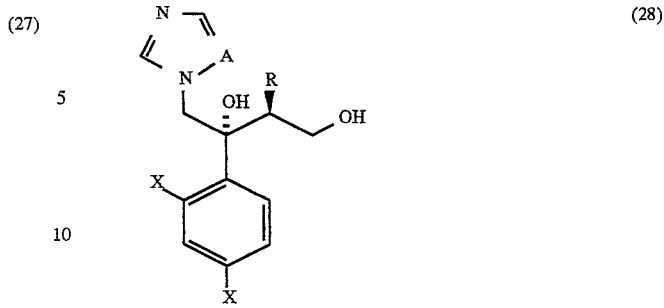

(28)

wherein R, X and A have the same groups as defined above respectively, with an oxidizing agent; and a process for the preparation of compounds represented by the general formula:

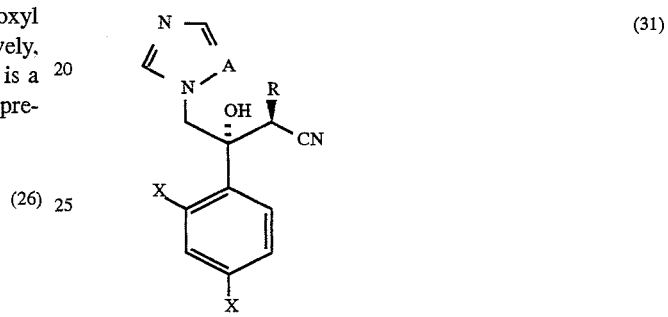

(31)

wherein R means a lower alkyl group, Xs are identical to or different from each other and denote hydrogen atom or a halogen atom, and A stands for CH or a nitrogen atom, respectively, or salts thereof, which comprises reacting a compound represented by the general formula:

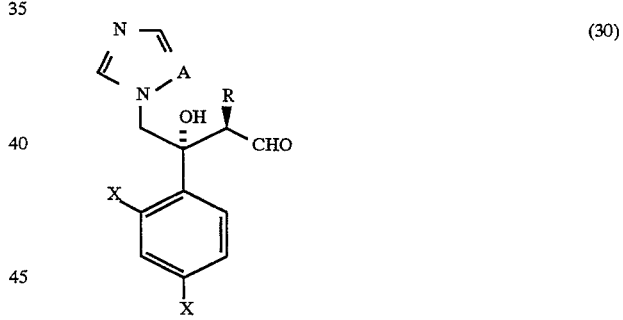

(30)

wherein R, X and A have the same groups as defined above respectively, with hydroxylamine-O-sulfonic acid.

These processes relate to processes for the preparation of synthetic intermediates useful for the preparation of antifungal agent.

This invention further relates to the following compounds or salts thereof which are useful as synthetic intermediates. That is, the present invention relates to compounds represented by the general formula:

(32)

wherein R means a lower alkyl group, Pr denotes a protecting group for hydroxyl group, and L represents a leaving group, respectively, or sales thereof;

compounds represented by the general formula:

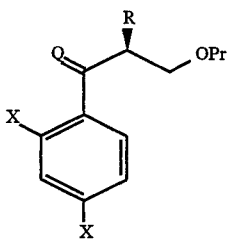

(33)

wherein R means a lower alkyl group, Xs are identical to or different from each other and denote hydrogen atom or a halogen atom, Pr stands for a protecting group for hydroxyl group, and Q represents oxygen atom or CH$_2$, respectively, or salts thereof;

compounds represented by the general formula:

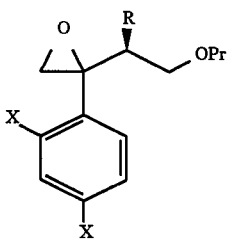

(34)

wherein R means a lower alkyl group, Xs are identical to or different from each other and denote hydrogen atom or a halogen atom, and Pr stands for a protecting group for hydroxyl group, respectively, or salts thereof;

compounds represented by the general formula:

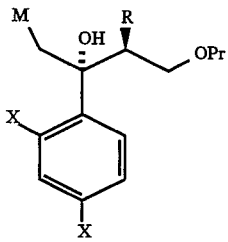

(35)

wherein R means a lower alkyl group, Xs are identical to or different from each other and denote hydrogen atom or a halogen atom, and Pr stands for a protecting group for hydroxyl group, and M represents hydroxyl group or a leaving group, respectively, or salts thereof; and compounds represented by the general formula:

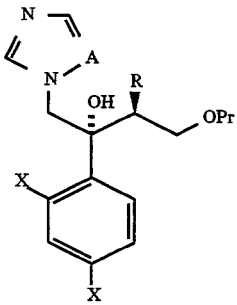

(36)

wherein R means a lower alkyl group, Xs are identical to or different from each other and denote hydrogen atom or a halogen atom, and Pr stands for a protecting group for hydroxyl group, and A represents CH or a nitrogen atom, respectively, and salts thereof.

The following are detailed explanation of this invention and terms used herein.

R means a lower alkyl group. The lower alkyl group stands for a straight or branched chain alkyl group containing 1–6 carbons, for example, methyl group, ethyl group, n-propyl group, i-propyl group, n-butyl group, i-butyl group, sec-butyl group, t-butyl group, n-pentyl group, i-pentyl group, sec-pentyl group, t-pentyl group, neopentyl group, 1-methylbutyl group, 2-methylbutyl group, 1,1-dimethylpropyl group, 1,2-dimethylpropyl group, n-hexyl group, i-hexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3,-dimethylbutyl group, 1-ethylbutyl group, 2-ethylbutyl group, 1,1,2-trimethylpropyl group 1,2,2-trimethylpropyl group, 1-ethyl-1-methylpropyl group, 1-ethyl-2-methylpropyl group and the like. Preferable group includes methyl group, ethyl group, propyl group and the like.

R$_1$ denotes a hydrogen atom or a protecting group for a carboxyl group.

The protecting group for a carboxyl group used herein may be any groups known usually in the organic synthesis art as the protecting group for a carboxyl group, and is not especially limited. The exemplified protecting group for a carboxyl group includes for example, straight chain or branched chain lower alkyl groups containing 1–6 carbon atoms, such as methyl group, ethyl group, isopropyl group and t-butyl group; halogeno lower alkyl groups, such as 2-iodoethyl group and 2,2,2,-trichloroethyl group; lower alkoxyalkyl groups, such as methoxymethyl group, ethyoxymethyl group and isobutoxymethyl group; lower aliphatic acyloxyalkyl groups, such as acetoxymethyl group, propionyloxymethyl group, butyryloxymethyl group and pivaloyloxymethyl group; lower alkoxycarbonyloxyalkyl groups, such as methoxycarbonyloxymethyl group, 1-methoxycarbonyloxyethyl group, ethoxycarbonyloxymethyl group, 1-ethoxycarbonyloxymethyl group and 2-methoxycarbonyloxyethyl group; aralkyl groups, such as benzyl group, p-methoxybenzyl group, o-nitrobenzyl group and p-nitrobenzyl group; benzhydryl group and phthalidyl group; (5-methyl-2-oxo-1,3-dioxo-4-yl)-methyl group, and the like.

Deblocking of these protecting group for a carboxyl group can be achieved by a conventional process such as hydrolysis, reduction or the like depending upon the type of the protecting group used.

Pr denotes a protecting group for a hydroxyl group.

The protecting group for a hydroxyl group used herein may be any groups known in the organic synthesis art as the protecting group for a hydroxyl group, and is not especially limited. The exemplified protecting group for a hydroxyl group includes, for example, lower alkylsilyl groups, such as trimethylsilyl group, t-butyldimethylsilyl group and the like; lower alkylarylsilyl groups, such as t-butyldiphenylsilyl group and the like; lower alkoxymethyl groups, such as methoxymethyl group, 2-methoxyethoxymethyl group and the like; for example, tetrahydropyranyl group; aralkyl groups, such as benzyl group, p-methoxybenzyl group, 2,4-dimethoxybenzyl group, o-nitrobenzyl group, p-nitrobenzyl group, trityl group, methoxytrityl group, dimethoxytrityl group and the like; acyl groups, such as formyl group, acetyl group and the like; lower alkoxycarbonyl groups, such as t-buthoxycarbonyl group, 2-iodoethoxycarbonyl group, 2,2,2-trichloroethoxycarbonyl group and the like; alkenyloxycarbonyl groups, such as 2-propenyloxycarbonyl group, 2-chloro-2-propenyloxycarbonyl group, 3-methoxycarbonyl-2-propenyloxycarbonyl group, 2-methyl-2-propenyloxycarbonyl group, 2-butenyloxycarbonyl group, cinnamyloxycarbonyl group and the like; aralkyloxycarbonyl groups, such as benzyloxycarbonyl group, p-methoxybenzyloxycarbonyl group, o-nitrobenzyloxycarbonyl group, p-nitrobenzyloxycarbonyl group and the like.

Deblocking of thease protecting groups for a hydroxy group can be achieved by a conventional process such as hydrolysis, reduction or the like, depending upon the type of protecting group used.

L stands for a leaving group.

The leaving group used herein may be any groups known in the organic synthesis art as the leaving group, and is not especially limited. The exemplified leaving group includes, for example, halogen atoms, such as chlorine atom, bromine atom, iodine atom and the like; alkylthio groups, such as methylthio group, ethylthio group, propylthio group and the like; arylthio groups, such as phenylthio group, tolylthio group, 2-pyridylthio group and the like; alkylsulfonyloxy groups, such as mesyloxy group, trifuluoromethanesulfonyloxy group, ethanesulfonyloxy group, propanesulfonylolxy group and the like; arylsulfonyloxy groups, such as benzensulufonyloxy group, tosyloxy group and the like; alkanoyloxy groups, such as acetoxy group, trifluoroacetoxy group and the like; alkoxy groups, such as methoxy group, ethoxy group, propoxy group and the like; aklylamino groups, such as methylamino group, ethylamino group, propylamino group, butylamino group and the like; dialkylamino groups such as dimethylamino group, diethylamino group, dipropylamino group, methylethylamino group, ethylpropylamino group, methylpropylamino group and the like; and substituted phosphoryloxy group, such as diphenoxyphosphoryloxy group and the like. Accordingly, the activating reagent used in the reaction of this invention includes, for example, acid anhydrides, such as trifluoroacetic anhydride, methanesulfonic anhydride, trifluoromethanesulfonic anhydride, p-toluenesulfonic anhydride and the like; acid chlorides, such as methanesulfonylchloride, p-toluensulfonylchloride, diphenylchlorophosphate and the like, and moreover includes 2-mercaptopyridine, oxalylchloride, thionylchloride thionylbromide and the like.

Xs are identical to or different from each other and denotes a hydrogen atom or halogen atom. Exemplified halogen atom includes fluorine atom, chlorine atom, bromine atom, iodine atom and the like.

Y means chlorine atom, bromine atom or iodine atom. The reactive derivative of the compound represented by the general formula:

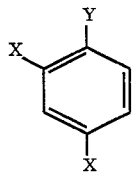

(6)

wherein Xs are identical to or different from each other and denote a hydrogen atom or a halogen atom, and Y represents chlorine atom, bromine atom or iodine atom respectively, can be obtained, for example, by activating Y with a metal such as Mg to form magnesium halide (—MgY), that is, to form Grignard reagent.

The peroxy acid used herein may be any those usually used in organic synthesis, and is not especially limited. Exemplified peroxy acid includes, for example organic peroxy acids, such as methachloroperbenzoic acid (m CPBA), peracetic acid and the like, and aqueous hydrogen peroxide. Methachloroperbenzoic acid is preferable.

The oxidizing agent used herein may be any those conventionally used as an oxidizing agent in organic synthesis, and is not especially limited. Example of the oxidizing agent can includes, for example, osmium tetraoxide, potassium permanganate and the like.

The alkoxydimethylsilylmethyl magnesium halide means a dimethylsilylmethyl magnesium halide substituted with an alkoxy group corresponding to the lower alkyl group as described above, and practically includes methoxydimethylsilylmethyl magnesium chloride, methoxydimethylsilylmethyl magnesium bromide, ethoxydimethylsilylmethyl magnesium chloride, ethoxydimethylsilylmethyl magnesium bromide, propoxydimethylsilylmethyl magnesium chloride, i-propoxydimethylsilylmethyl magnesium chloride, propoxydimethylsilylmethyl magnesium bromide, i-propoxydimethylsilylmethyl magnesium bromide and the like. The dialkoxymethylsilylmethyl magnesium halide means a methylsilylmethyl magnesium halide substituted with an alkoxy group corresponding to the lower alkyl group as described above, and practically includes dimethoxymethylsilylmethyl magnesium chloride, dimethoxymethylsilylmethyl magnesium bromide, diethoxymethylsilylmethyl magnesium chloride, diethoxymethylsilylmethyl magnesium bromide, dipropoxymethylsilylmethyl magnesium chloride, dipropoxymethylsilylmethyl magnesium bromide, dibutoxymethylsilylmethyl magnesium chloride, dibutoxymethylsilylmethyl magnesium bromide and the like.

The base used herein may be any those usually known in the organic synthesis art as a base, and is not especially used. Exemplified base includes, for example, sodium carbonate, sodium hydrogencarbonate, potassium carbonate, sodium hydride, potassium hydride, t-butoxy potassium, pyridine, dimethylaminopyridine, trimethylamine, triethylamine, N,N-diisopropylethylamine, N-methylmorpholine, N-methylpyrolidine, N-methylpiperidine, N,N-dimethylaniline, 1,8-diazabicyclo[5.4.0]undeca-7-en (DBU), pyridine, 4-dimethylaminopyridine, picoline, lutidine, quinoline, isoquinoline, sodium hydroxyde, potassium hydroxide, lithium hydroxide, butyl lithium and the like.

A means CH or nitrogen atom.

$R^2$ represents a lower alkyl group. The lower alkyl group has the same meaning as described above.

$R^3$ represents a methyl group or a lower alkoxy group. The lower alkoxy group corresponds to the above described lower alkyl group, and being practically a straight chain or branched chain alkoxy group containing 1–6 carbons, and includes, for example, methoxy group, ethoxy group, n-propoxy group, i-propoxy group, n-butoxy group, i-butoxy group, sec-butoxy group, t-butoxy group, n-pentyloxy i-pentyloxy group, sec-pentyloxy group, t-pentyloxy group, neopentyloxy group, 1-methylbutoxy group, 2-methylbutoxy group, 1,1-dimethylpropoxy group, 1,2-dimethylpropoxy group, n-hexyloxy group, i-hexyloxy group, 1-methylpentyloxy group, 2-methylpentyloxy group, 3-methylpentyloxy group, 1,1-dimethylbutoxy group, 1,2-dimethylbutoxy group, 2,2-dimethylbutoxy group, 1,3-dimethylbutoxy group, 2,3-dimethylbutoxy group, 3,3,-dimethylbutoxy group, 1-ethylbutoxy group, 2-ethylbutoxy group, 1,1,2-trimethylpropoxy group, 1,2,2-trimethylpropoxy group, 1-ethyl-1-methylpropoxy group, 1-ethyl-2-methylpropoxy group and the like.

Q represents oxygen atom or $CH_2$

M represents hydroxy group or a leaving group. The leaving group has the same meaning as described above.

The salt used is not limited to the type thereof, and includes, for example, addition salts of inorganic acid, such as hydrofluoride, hydrochloride, sulfate, nitrate, perchlorate, phosphate, carbonate, hydrogencarbonate, hydrobromate, hydroiodide and the like; addition salts of organocarboxylic acid, such as acetate, maleate, fumarate, oxalate, lactate, citrate, trifuluoroacetate and the like; addition salts of organosulfonic acid, such as methansulfonate, trifuluoromethanesulfonate, ethanesulfonate, hydroxymethanesulfonate, hydroxyethanesulfonate, benzensulfonate, toluenesulfonate, taurine salt and the like; addition salts of amine, such as a salt of trimethylamine, a salt of triethylamine, a salt of pyridine, a salt of procaine a salt of picoline, a salt of dicyclohexylamine, a salt of N,N'-dibenzylethylenediamine, a salt of N-methylglucamine, a salt of diethanolamine, a salt of triethanolamine, a salt of tris(hydroxymethylamino) methane, a salt of phenetylbenzylamine and the like; addition salts of alkali metal, such as sodium salt, potassium salt and the like; addition salts of alkaline earth metal, such as magnesium salt, calcium salt and the like; addition salts of amino acid, such as a salt of arginine, a salt of lysine, a salt of seline, a salt of glycine, a salt of aspartic acid, a salt of glutamic acid and the like.

The pharmaceutically acceptable salt means conventional salt usualy used for preparing medicines.

The hydroxyamine derivative used herein may be any compound which is usually possible to derive cyano group from formyl group therein in the organic synthesis, and is not especially limited, and includes, for example, hydroxylamine-O-sulfonic acid and the like.

Preparation processes according to the present application, which are represented by the following general scheme, will then be described.

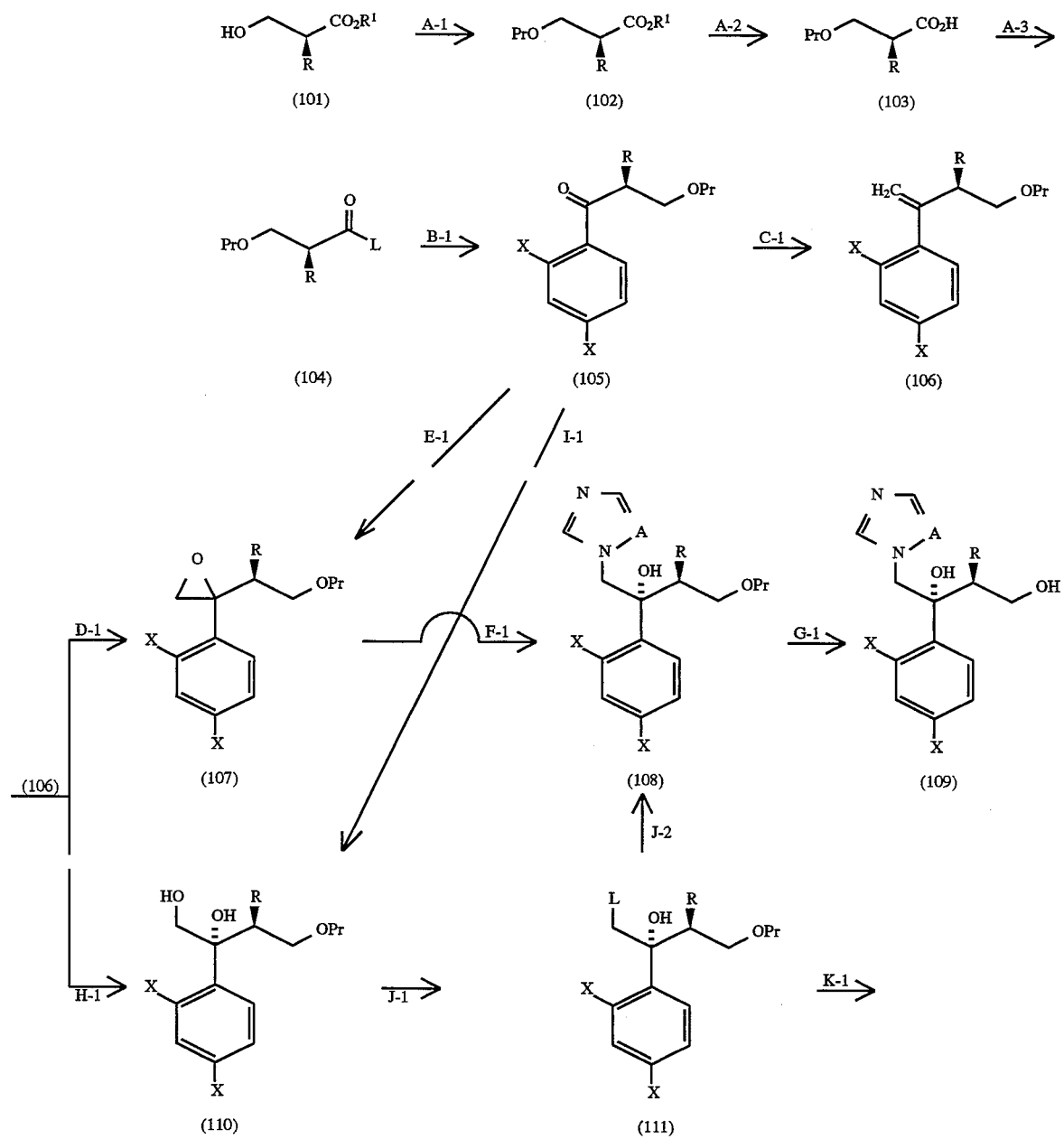

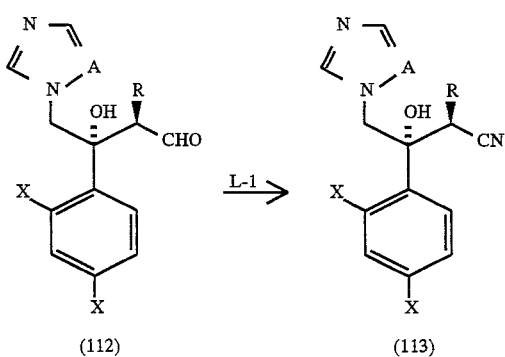
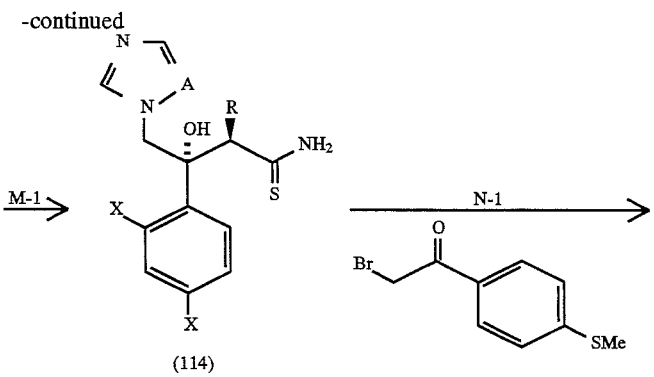

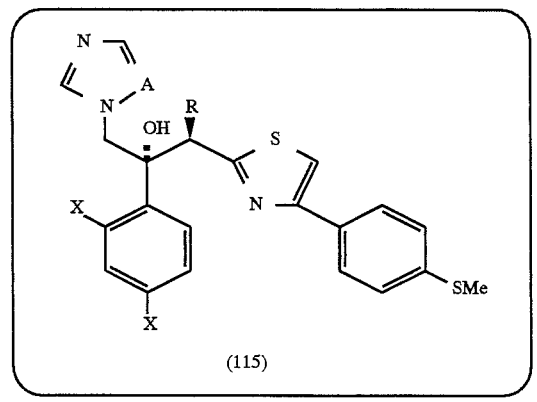

Route A-1 is a route in which the hydroxyl group of a compound represented by the formula (101) [in which R and R¹ each mean the same groups as defined above. The same shall apply hereinafter] is protected. A compound represented by the formula (102) [in which Pr means the same group as defined above. The same shall apply hereinafter], the hydroxyl group of which has been protected in this manner, can be prepared by protecting the hydroxyl group in accordance with a method known per se in the art. Hydroxyl groups protected by various protecting groups may be prepared in accordance with, for example, the method described in Green, "Protective Groups in Organic Synthesis (A Wiley-Interscience Publication Co.,)".

Route A-2 is a route in which the protecting group for the carboxyl group of the compound represented by the formula (102) is deblocked. As with Route A-1, in this route, a compound represented by the formula (103) can be prepared by a method of deblocking the protecting group for the carboxylic acid in accordance with the conventional method, for example, hydrolysis or catalytic reduction with an acid or base. More specifically, the deblocking may be performed by reacting the compound of the formula (102) with hydrochloric acid, trifluoroacetic acid, acetic acid, hydrogen bromide, formic acid, tosic acid, hydrogen peroxide, trimethylsilyl chloride, potassium t-butoxide, lithium hydroxide, sodium hydroxide, potassium hydroxide, hydrazinc, potassium carbonate, sodium carbonate, boron trifluoride, boron tribromide, aluminum halide, tetrabutylammonium fluoride or the like, in a slovent which does not inhibit the reaction.

Route A-3 is a process in which a leaving group (L) is added to the compound represented by the formula (103). A compound of the formula (104) can be obtained by reacting the compound represented by the formula (103) with an activating reagent, for example, an acid anhydride such as trifluoroacetic anhydride, methanesulfonic anhydride, trifluoromethanesulfonic anhydride or p-toluenesulfonic anhydride; an acid chloride, for example, methanesulfonyl chloride, p-toluenesulfonyl chloride, diphenyl chlorophosphate, oxalyl chloride or thionyl chloride; or 2-mercaptopyridine. If desired, a condensation agent such as dicyclohexylcarbodiimide (DCC) may be used according to the reactivity of the reagent used.

In Route B-1, a compound of the formula (105), in which the leaving group L in the formula (104) is replaced by a disubstituted phenyl group, can be prepared by reacting the compound represented by the formula (104) with a compound represented by the formula

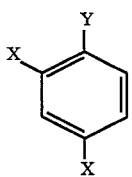

[in which X and Y each mean the same groups as defined above. The same shall apply hereinafter.], or a reactive derivative thereof, for example, a Grignard reagent in which Y means —MgCl, —MgBr or —MgI activated by metallic magnesium.

In Route C-1, an olefin compound represented by the formula (106) can be prepared by reacting (so-called Wittig reaction) the compound represented by the formula (105) with triphenylphosphonium methylide, which is derived by treating methyltriphenylphosphonium chloride, methyltriphenylphosphonium bromide or methyltriphenylphosphonium iodide with a base such as butyllithium, or by reacting it with trimethylsilylmethylmagnesium chloride, trimethylsilylmethylmagnesium bromide or trimethylsilylmethyllithium to form a silyl alcohol intermediate and subjecting the silyl alcohol intermediate to desilylalcoholation with a boron trifluoride ether complex or the like.

Route D-1 is a route in which the olefin compound represented by the formula (106) is epoxidized. No particular limitation is imposed on a reagent for the epoxidation so far as it is a reagent capable of epoxidizing a double bond. However, as examples thereof, may be mentioned organic peroxy acids such as meta-chloroperbenzoic acid (mCPBA) and peracetic acid, and aqueous hydrogen peroxide. An epoxy compound represented by the formula (107) can be prepared, preferably, by a reaction with meta-chloroperbenzoic acid.

The epoxy compound represented by the formula (107) can also be obtained by the following Route E-1. Namely, the epoxy compound can be prepared by reacting the compound of the formula (105) with chloromethyllithium formed from chloroiodomethane or bromoiodomethane by a base such as butyllithium, or with dimethylsulfoxonium methylide, dimethylsulfonium methylide, diethylsulfoxonium methylide or diethylsulfonium methylide.

Route F-1 is directed to a reaction in which the epoxy compound represented by the formula (107) is directly ring-opened to bond an imidazole ring or 1,2,4-triazole ring. A compound represented by the formula (108) [in which A means a nitrogen atom or CH. The same shall apply hereinafter] can be obtained by reacting the epoxy compound represented by the formula (107) with an alkali metal salt of imidazole or 1,2,4-triazole, which is obtained by mixing an alkali metal hydride such as sodium hydride, lithium hydride or potassium hydride with imidazole or 1,2,4-triazole in a solvent.

Route G-1 is a route in which a protecting group for the hydroxyl group is deblocked. This protecting group for the hydroxyl group can be deblocked by a method known per se in the art. For example, it may be conducted by the method described in the Green's literature given above.

Route H-1 is a route in which the olefin compound is oxidized into a 1,2-glycol with an oxidizing agent. A compound represented by the formula (110) can be prepared by treating the compound represented by the formula (106) with an oxidizing agent such as osmium tetroxide or potassium permanganate.

Route I-1 is a route in which the compound represented by the formula (105) is converted to the compound represented by the formula (110). In this route, the compound represented by the formula (110) can be prepared by reacting the compound represented by the formula (105) with an alkoxy-dimethylsilylmethylmagnesium halide or dialkoxymethylsilylmethylmagnesium halide to form a compound represented by the general formula

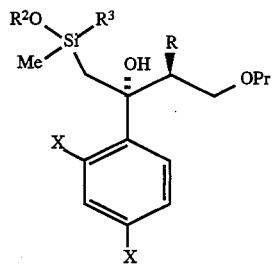

(17)

[in which $R^2$ means a lower alkyl group, and $R^3$ denotes a methyl or lower alkoxy group. The same shall apply hereinafter], and then reacting the thus-obtained compound with a peroxy acid in the presence of a base.

Route J-1 is a route in which the primary hydroxyl group of the compound represented by the formula (110) is replaced by a leaving group L. This process can be conducted in accordance with Route A-3. A compound represented by the formula (111) can be prepared by reacting the compound of the formula (110) with, preferably, an acid chloride such as methanesulfonyl chloride, p-toluenesulfonyl chloride, diphenyl chlorophosphate, oxalyl chloride or thionyl chloride.

In Route J-2, the leaving group L of the compound represented by the formula (111) can be replaced by an imidazolyl or 1,2,4-triazolyl group by conducting a reaction in accordance with Route F-1.

Route K-1 is a route in which the primary hydroxyl group of a compound represented by the formula (109) is oxidized into a formyl group. The oxidation of this primary hydroxyl group can be conducted by a method known per se in the art. It is easy to conduct by using, for example, a salt or oxide of a metal such as chromium, manganese or silver, or an organic oxidizing agent typified by dimethyl sulfoxide (DMSO). As its reagent, there may be used, for example, a chromic acid.pyridine complex, pyridinium chlorochromate or pyridinium dichromate. Alternatively, an oxidizing method with DMSO making use of oxalyl chloride is commonly used.

Route L-1 is a route in which the formyl group of a compound represented by the formula (112) is replaced by a cyano group. A compound represented by the formula (113) can be prepared by reacting the compound represented by the formula (112) with a hydroxylamine derivative such as hydroxylaminesulfonic acid.

Routes M-1 and N-1 are preparation processes of an antifungal agent, which is a final compound and represented by the formula (115). In these routes, the compound exhibiting excellent antifungal activity and represented by the formula (115) can be prepared by adding hydrogen sulfide to the compound represented by the formula (113) to form a compound represented by the formula (114) and then reacting the thus-obtained compound with 2-bromo-4'-methylthioacetophenone.

The reactions in the above-described routes may be conducted in a temperature range of generally from −78° C. to 150° C., preferably from −40° to 50° C., more preferably from −20° to 25° C.

No particular limitation is imposed on solvents usable in the present invention so far as they do not impede the reactions and are usually used in organic syntheses. However, as examples thereof, may be mentioned lower alcohols such as methanol, ethanol, propanol and butanol; polyhydric alcohols such as ethylene glycol and glycerol; ketones such as acetone, methyl ethyl ketone, diethyl ketone and cyclohexanone; ethers such as diethyl ether, isopropyl ether, tetrahydrofuran, dioxane, 2-methoxyethanol and 1,2-dimethoxyethane; nitriles such as acetonitrile and propionitrile; esters such as methyl acetate, ethyl acetate, isopropyl acetate, butyl acetate and diethyl phthalate; halogenated hydrocarbons such as dichloromethane, chloroform, carbon tetrachloride, 1,2-dichloroethane, trichloroethylene and tetrachloroethylene; aromatics such as benzene, toluene, xylene, monochlorobenzene, nitrobenzene, indene, pyridine, quinoline, collidine and phenol; hydrocarbons such as pentane, cyclohexane, hexane, heptane, octane, isooctane, petroleum benzin and petroleum ether; amines such as ethanolamine, diethylamine, triethylamine, pyrrolidine, piperidine, piperazine, morpholine, aniline, dimethylaniline, benzylamine and toluidine; amides such as formamide, N-methylpyrrolidone, N,N-dimethylimidazolone, N,N-dimethylacetamide and N,N-dimethylformamide; phosphoric amides such as hexamethylphosphoric triamide and hexamethylphosphorous triamide; organic acids such as formic acid, acetic acid, difluoroacetic acid, trifluoroacetic acid and chloroacetic acid; sulfoxides such as dimethyl sulfoxide; carbon sulfides such as carbon disulfide; water; and other solvents generally used. These solvents may be simple solvents or mixed solvents of two or more solvents thereof. No particular limitation is imposed on the mixing ratio of the mixed solvents.

In the above routes, the formed products may be purified by a method known per se in the art, such as column chromatography on silica gel or the like if necessary, and they may be subjected to deblocking reactions of their protecting groups if desired. The deblocking of the protecting groups may be conducted by subjecting the products to reduction such as catalytic reduction, or solvolysis.

Besides, compounds represented by the following formula:

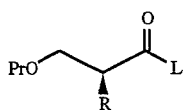

(116)

or salts thereof, compounds represented by the general formula:

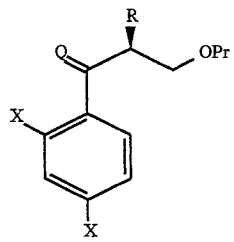

(117)

or salts thereof, compounds represented by the general formula:

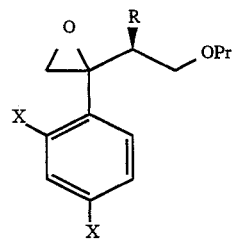

(118)

or salts thereof, compounds represented by the general formula:

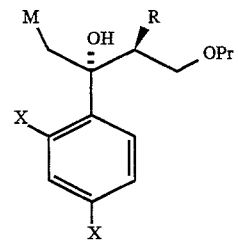

(119)

or salts thereof, and compounds represented by the general formula:

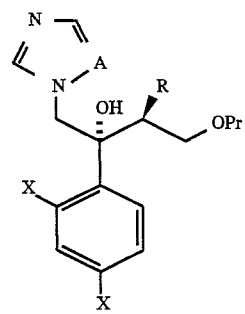

(120)

or salts thereof [in the formulae (116) to (120), R, Pr, L, X, Q, M and A each mean the same groups as defined above] are useful for the preparation processes of the present application and the syntheses of the compounds having excellent antifungal activity.

Here, in the compounds and the preparation processes according to the present invention, stereoisomers having an asymmetric carbon atom in their molecules and taking an S-configuration or an R-configuration exist. Besides, with respect to those having a double bond, geometric isomers of E or Z type exist. For the sake of convenience, one configuration is described in the specification. However, both compounds thereof and mixtures thereof are all embraced in the present invention. The compounds according to the present invention are not limited to those represented by the formulae described for the sake of convenience. Optical isomers can be separated by the general technique of optical resolution, while diastereomers can be separated by using a usual separating method such as chromatography.

When individual isomers are intended to prepared, they may be prepared stereoselectively or enantioselectively in accordance with their corresponding preparation processes of the present application.

From the viewpoint of antifungal activity, it is sterically preferable to use a preparation process wherein optically active (S)-methyl hydroxy-2-methylpropionate is use as a compound of the general formula (101), or a starting material, to perform the above preparation processes so as to form a compound of the general formula (113) while keeping the stereostructure, thereby obtaining optically active (2S,3R)-3-(2,4-difluorophenyl)-3-hydroxy-2-methyl-4-(1H-1,2,4-triazol-1-yl)butyronitrile as a compound of the general formula (113), and intermediates for synthesis having such a stereostructure.

According to the present application, for example, novel compounds represented by the general formula:

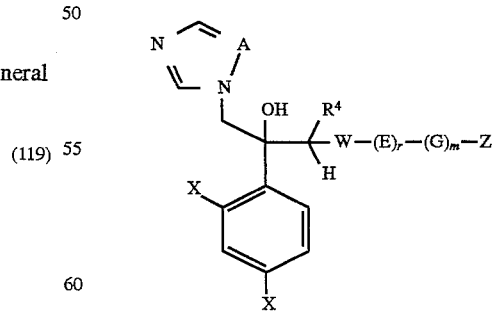

wherein Xs are identical to or different from each other and mean individually a halogen or hydrogen atom; $R^4$ denotes a hydrogen atom or lower alkyl group, r and m may be identical with or different from each other and stand individually for 0 or 1; A is N or CH; W denotes an aromatic ring which may have one or more substituent groups and may contain one or more hetero-atoms selected from N, S and O, or a condensed ring thereof; E means an aromatic ring which may have one or more substituent groups and may contain one or more hetero-atoms selected from N, S and O, an alkanediyl group which may have one or more substituent groups, an alkenediyl group which may have one or more substituent groups, or an alkynediyl group which may have one or more substituent group; G stands for a group represented by the formula —S—, >SO, >SO$_2$, >C=S, >C=O, —O—, >N—R$^5$, >C=N—OR$^5$ or —(CH$_2$)$_j$—, in which R$^5$ means a hydrogen atom or lower alkyl group, and j stands for an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenoxy group which may have one or more substituent group, imidazolyl group which may have one or more substituent group, triazolyl group which may have one or more substituent group, tetrazolyl group which may have one or more substituent group, or amino group which may have one or more substituent group, or salts thereof can be prepared.

Some examples will hereinafter be shown to describe the present invention in more detail. However, the present invention is not limited to these examples only. In the following examples, $^1$H NMR spectra were measured by means of an FT NMR (400 MHz) manufactured by Varian Company.

Incidentally, Tr, Ms, MOM, TBDPS and Bn will hereinafter mean trityl, mesyl, methoxymethyl, t-butyldiphenylsilyl and benzyl groups, respectively.

EXAMPLES

The present invention will hereinafter be described more specifically by Examples, and Experimental Examples, and Preparation Examples. However, the present invention is not limited to these examples, experimental examples and preparation examples, only.

EXAMPLE 1

Synthesis of 1-(2,4-difluorophenyl)-1-(4-(2,4-difluorophenyl)thiazol-2-yl)-2-(1H-1,2,4-triazol-1-yl)ethanol

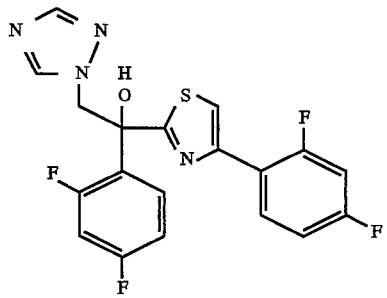

After 4-(2,4-difluorophenyl)thiazole (330 mg) was dissolved in diethyl ether (3 ml), and the resultant solution was cooled to –78° C. in a nitrogen atmosphere, a 1.6M solution (1.06 ml) of n-butyllithium in hexane was added, and the resultant mixture was stirred for about 10 minutes. After a solution of 2-chloro-2',4'-difluoroacetophenone (306 mg) in tetrahydrofuran was added dropwise to this mixture, the liquid reaction mixture was heated to –20° C. to add an aqueous solution of ammonium chloride. The reaction mixture was extracted with ethyl acetate. After drying an organic layer over magnesium sulfate, the solvent was distilled out under reduced pressure. The residue was dissolved in dimethylformamide (3 ml) to form a solution (A). On the other hand, a dimethylformamide solution (3 ml) (B) containing 1,2,4-triazole (350 ml) and 60% sodium hydride (135 mg) was prepared. The solution (B) was then added to the solution (A), and the mixture was heated at 60° C. for 6 hours. After ethyl acetate and water were added to the liquid reaction mixture, and an organic layer was washed several times with water, the solvent was distilled out. The residue was subjected to column chromatography on silica gel to recrystallize a fraction containing the intended compound from diethyl ether, thereby obtaining the title compound (390 mg). Its physical properties are shown in Table 1 which will be described subsequently.

EXAMPLE 2

(1) Synthesis of 1-(2,4-difluorophenyl)-1-(6-cyanobenzothiazol-2-yl)-2-chloroethanol

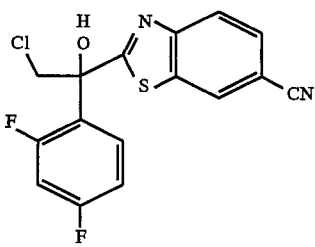

After 6-cyanobenzothiazole (1.60 g) was dissolved in tetrahydrofuran (80 ml), and the solution was cooled to –98° C. in a nitrogen atmosphere, a 1.6M solution (5.9 ml) of n-butyllithium in hexane was added dropwise over 10 minutes, and the resultant mixture was stirred for 5 minutes. A solution of 2-chloro-2',4'-difluoroacetophenone (2.85 g) in tetrahydrofuran (20 ml) was added dropwise to this mixture. After the liquid reaction mixture was heated to –10° C., an aqueous solution of ammonium chloride was added thereto. After the mixture was heated to room temperature, an organic layer was taken out, and the solvent was distilled out under reduced pressure. A water layer was extracted with ethyl acetate and the extract was then put together with the residue of the organic layer. This organic layer was washed with water and then with saturated saline, dried over magnesium sulfate and then distilled under reduced pressure. The residue was subjected to column chromatography on silica gel (solvent: hexane/ethyl acetate=20/1, next, hexane/ethyl acetate=5/1), thereby obtaining the intended compound (1.49 g).

(2) Synthesis of 1-(2,4-difluorophenyl)-1-(6-cyanobenzothiazol-2-yl)-2-(1H-1,2,4-triazol-1-yl)-ethanol

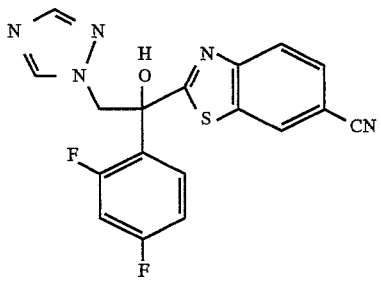

Sodium hydride (440 mg) was suspended in dimethylformamide (10 ml), and 1,2,4-triazole (948 mg) was added to the suspension, to which a solution of 1-(2,4-difluorophenyl)-1-(6-cyanobenzothiazol-2-yl)-2-chloro-ethanol (1.49 g) in dimethylformamide (10 ml) was added. The mixture was heated at 60° C. for 4 hours. After the liquid reaction mixture was cooled to room temperature, ethyl acetate and water were added thereto. An organic layer separated was washed three times with water and then dried over magnesium sulfate, and the solvent was distilled out. The residue was recrystallized from dichloromethane-diisopropyl ether to obtain the intended compound (1.17 g). Melting point: 170°–172° C.

EXAMPLE 3

Synthesis of 1-(2,4-difluorophenyl)-1-{4-[(4(5-tetrazole)-phenyl)thiazol]-2-yl}-2-(1H-1,2,4-triazol-1-yl)ethanol

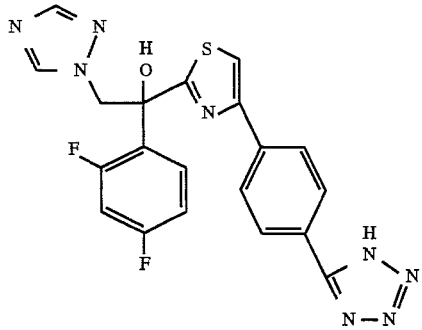

1-(2,4-Difluorophenyl)-1-(4-(4-cyanophenyl)-thiazol-2-yl)-2-(1H-1,2,4-triazol-1-yl)ethanol (melting point: 195°–198° C.) (400 mg) was dissolved in dimethylformamide (1.2 ml). To the solution, were added sodium azide (191 mg) and triethylamine hydrochloride (404 mg). The resultant mixture was heated overnight (for 12 hours) at 100° C. After insoluble matter was removed by filtration, and the solvent was distilled out, the residue was dissolved in a small amount (each about 2 ml) of acetone and ethyl acetate. Water was added to the solution, and the pH of the solution was adjusted to about 4 with concentrated hydrochloric acid. The formed precipitate was collected by filtration, washed with water and then dried, thereby obtaining the title compound (380 mg). Melting point: 252°–254° C. Its physical properties are shown in Table 2 which will be described subsequently.

EXAMPLE 4

Synthesis of 1-(2,4-difluorophenyl)-1-{4-[(4(5-(3-methyl)tetrazole)phenyl)-thiazol]-2-yl}-2-(1H-1,2,4-triazol-1-yl)ethanol [Structural Formula A] and 1-(2,4-difluorophenyl)-1-{4-[(4-(5-(4-methyl)tetrazole)-phenyl)-thiazol]-2-yl}-2-(1H-1,2,4-triazol-1-yl)ethanol [Structural Formula B]

Structural Formula A:

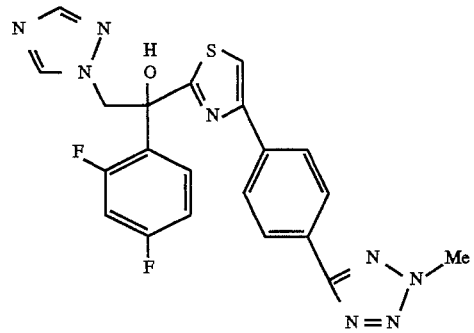

Structural Formula B:

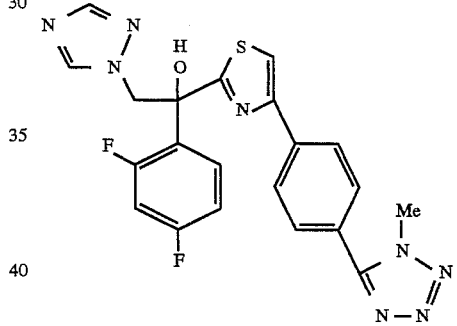

1-(2,4-Difluorophenyl)-1-{4-[(4-(5-tetrazole)-phenyl)-thiazol]-2-yl}-2-(1H-1,2,4-triazol-1-yl)ethanol (320 mg) obtained in Example 3 was dissolved in dimethylformamide (3 ml). To the solution, cesium carbonate (231 mg) was added, and the mixture was stirred at 60° C. for 30 minutes, and then cooled to room temperature. Methyl iodide (0.048 ml) was added, and the resultant mixture was stirred overnight at room temperature. The mixture was added with water and extracted with ethyl acetate. After the solvent was distilled under reduced pressure out of the extract, the residue was subjected to column chromatography on silica gel, thereby obtaining the compound [melting point: 188°–191° C.] of Structural Formula A by elution with 1% methanol.chloroform and then obtaining the compound [double melting point: 110°–115° C. and 185°–187° C.] (60 mg) of Structural Formula B by elution with 2% methanol.chloroform. Their physical properties are shown in Table 2 which will be described subsequently.

EXAMPLE 5

Synthesis of 1-(2,4-difluorophenyl)-1-[2-(4-1-1H-1,2,4-triazole)phenyl)-thiazol-5-yl)]-2-(1H-1,2,4-triazol-1-yl)ethanol

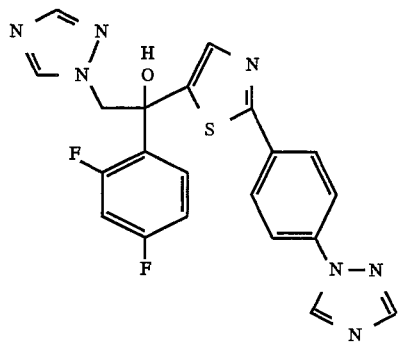

A solution of 1-(2,4-difluorophenyl)-1-(2-(4-fluorophenyl)thiazol-5-yl)-2-(1H-1,2,4-triazol-1-yl)ethanol in dimethylformamide (3 ml) was added dropwise to a solution in dimethylformamide (3 ml) prepared from 1H-1,2,4-triazole (168 mg) and 60% sodium hydride (81 mg). The resultant mixture was heated at 100° C. for 30 hours. After the liquid reaction mixture was cooled to room temperature, it was added with water and extracted with ethyl acetate. The solvent was distilled out of the extract, and the resulting residue was subjected to column chromatography on silica gel (eluted with 3% methanol.ethyl acetate), thereby obtaining the title compound (60 mg). Its physical properties are shown in Table 2 which will be described subsequently.

EXAMPLE 6

Synthesis of 1-(2,4-difluorophenyl)-1-(6-thiocarbamoylbenzothiazol-2-yl)-2-(1H-1,2,4-triazol-1-yl)-ethanol

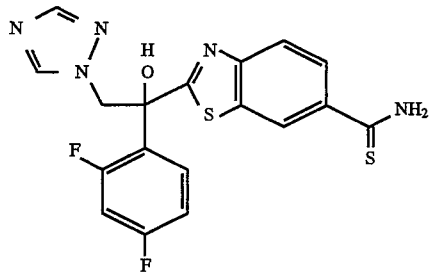

1-(2,4-Difluorophenyl)-1-(6-cyanobenzothiazol-2-yl)-2-(1H-1,2,4-triazol-1-yl)ethanol (418 mg) and triethylamine (500 ml) were dissolved in dimethylformamide (4 ml). While chilling with ice water, hydrogen sulfide gas was introduced into the resultant solution for 5 minutes. After left over for 6 hours at room temperature, water and ethyl acetate were added to the solution to separate liquid layers. An organic layer was washed twice with water and then with saline and then dried over magnesium sulfate. The solvent was distilled out to obtain the intended compound (437 mg). Its physical properties are shown in Table 2 which will be described subsequently.

EXAMPLE 7

Synthesis of 1-(2,4-difluorophenyl)-1-(6-(3-methylthiazol-1-yl)-benzothiazol-2-yl)-2-(1H-1,2,4-triazol-1-yl)ethanol

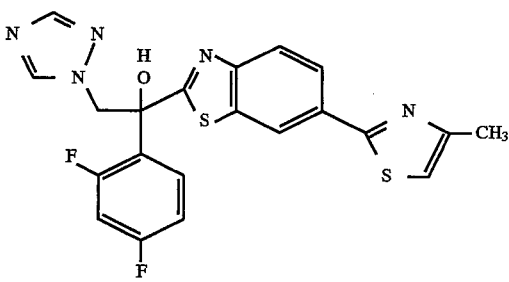

1-(2,4-Difluorophenyl)-1-(6-thiocarbamoylbenzothiazol-2-yl)-2-(1H-1,2,4-triazol-1-yl)ethanol (219 mg) was dissolved in ethanol (2 ml), and sodium hydrogencarbonate (42 mg) and bromoacetone (46 µl) were added to the solution. The resultant mixture was heated at 60° C. for 3 hours. Ethyl acetate and water were added to the liquid reaction mixture to separate liquid layers. An organic layer was washed with saline and then dried, and the solvent was distilled out. The residue was subjected to column chromatography on silica gel (eluting solvent: chloroform:methanol=100:1), thereby obtaining the intended compound (114 mg). Melting point: 213°–215° C.

EXAMPLE 8

Synthesis of 1-(2,4-difluorophenyl)-1-(6-thiazol-1-yl)benzothiazol-2-yl)-2-(1H-1,2,4-triazol-1-yl) ethanol

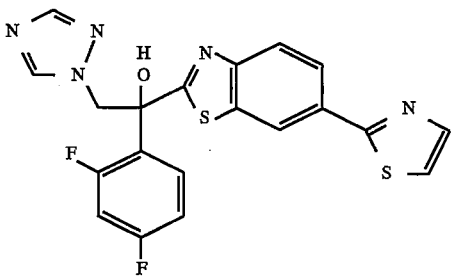

1-(2,4-Difluorophenyl)-1-(6-thiocarbamoylbenzothiazol-2-yl)-2-(1H-1,2,4-triazol-1-yl)ethanol (181 mg) and bromoacetaldehyde dimethylacetal (256 µl) were dissolved in ethanol (2 ml). Three drops of concentrated sulfuric acid were added to the solution to reflux it for 2.5 hours. After cooling the liquid reaction mixture, water and a saturated aqueous solution of sodium hydrogencarbonate were added thereto, and the resultant mixture was extracted with ethyl acetate. An organic layer was washed with water and then with saline, and dried over magnesium sulfate. The solvent was distilled out. Hexane was added to the residue to solidify the reaction product, which was then collected by filtration and washed with hexane, thereby obtaining the intended compound (168 mg). Melting point: 162°–166° C.

EXAMPLE 9

(1) Synthesis of 1-(2,4-difluorophenyl)-1-(4-(4-ethoxycarbonylthiazol-2-yl)-thiophen-2-yl)-2-(1H-1,2,4-triazol-1-yl)ethanol

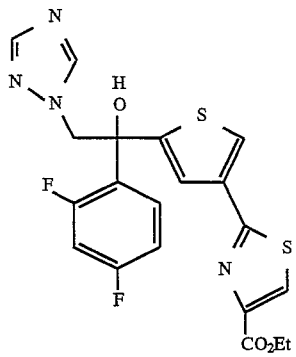

1-(2,4-Difluorophenyl)-1-(4-thiocarbamoylthiophen-2-yl)-2-(1H-1,2,4-triazol-1-yl)ethanol (1.6 g) was dissolved in dimethylformamide (10 ml), and α-bromoethylpyruvic acid (0.67 ml) was added to the solution. The resultant mixture was stirred at 60° C. for 4 hours. After the reaction, water was added, and the reaction mixture was extracted with ethyl acetate. An organic layer was washed with saturated saline. The residue was subjected to chromatography on silica gel (chloroform:methanol=80:1), thereby obtaining an oily substance (1.78 g).

(2) Synthesis of 1-(2,4-difluorophenyl)-1-(4-(4-carbamoylthiazol-2-yl)-thiophen-2-yl)-2-(1H-1,2,4-triazol-1-yl)ethanol

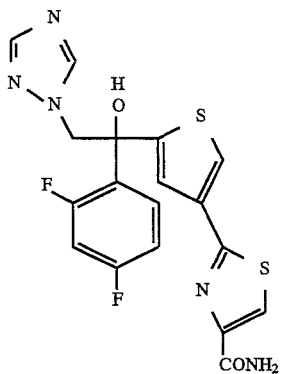

1-(2,4-Difluorophenyl)-1-(4-(4-ethoxycarbonylthiazol-2-yl)-thiophen-2-yl)-2-(1H-1,2,4-triazol-1-yl)ethanol (1.7 g) obtained in the step (1) was dissolved in a saturated methanol solution (35 ml) of ammonia, and the resultant solution was left over for 23 hours at room temperature. After the solvent was distilled out under reduced pressure, crystals (1.2 g) were obtained from dichloromethane-ether. Melting point: 112°–115° C.

EXAMPLE 10

Synthesis of 1-(2,4-difluorophenyl)-1-(4-(4-cyanothiazol-2-yl)-thiophen-2-yl)-2-(1H-1,2,4-triazol-1-yl)ethanol

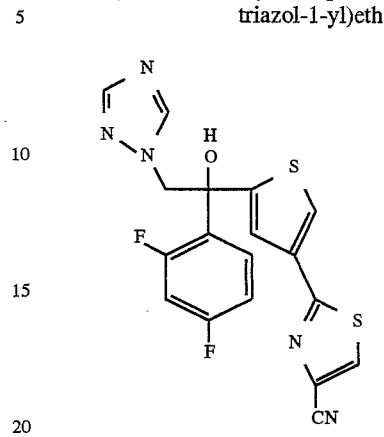

1-(2,4-Difluorophenyl)-1-(4-(4-carbamoylthiazol-2-yl)-thiophen-2-yl)-2-(1H-1,2,4-triazol-1-yl)ethanol (1.2 g) was dissolved in pyridine (7.1 ml). The solution was cooled on an ice bath, and phosphorus oxychloride (0.29 ml) was added thereto. The resultant mixture was stirred for 30 minutes. After the reaction, the reaction mixture was added with saline and extracted with ethyl acetate. An organic layer was washed once with 6N hydrochloric acid (20 ml) and then each once with water, a saturated aqueous solution of sodium hydrogencarbonate and saturated saline. After the thus-washed organic layer was dried over magnesium sulfate, the solvent was distilled out, and the residue was purified by chromatography on silica gel. Recrystallization from a solution of dichloromethane in ether was further conducted to obtain a solid (800 mg). Melting point: 172°–173° C.

EXAMPLES 11–17

Compounds represented by the general formula (II):

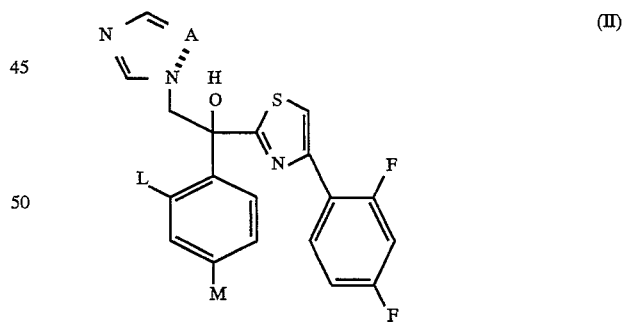

(II)

in which A, M and L were substituted as shown in Table 1, were prepared in the same manner as in Example 1.

TABLE 1

| Ex. | A | M | L | Physical properties |
|---|---|---|---|---|
| 1 | N | F | F | mp: 148–150° C. $^1$HN. M R. (CDCl$_3$) δ5.23(1H, d, J=14.1Hz), 5.28(1H, d, J=14.1Hz), 5.97(1H, s), 6.8–7.0(4H, m), 7.66(1H, d, J=2.2Hz), 7.69(1H, td, J=9.5, 6.4Hz), 7.86(1H, s), 8.10(1H, s), 8.14(1H, td, J=9.5, 6.6Hz) |
| 11 | CH | F | F | mp: 191–192° C. |

TABLE 1-continued

| Ex. | A | M | L | Physical properties |
|---|---|---|---|---|
| | | | | ¹HN. M. R. (DMSO-d₆) δ4.98(2H, brs), 6.67(1H, brs), 6.81(1H, brs), 7.0~7.08(1H, m), 7.18~7.26(2H, m), 7.30(1H, brs), 7.35~7.42(1H, m), 7.39(1H, s), 7.55~7.62(1H, m), 7.91(1H, d, J=2.5Hz), 8.12~8.2(1H, m) |
| 12 | N | F | H | mp: 158~160° C. |
| | | | | ¹HN. M.R. (DMSO-d₆) δ5.08(2H, brs), 7.1~7.18(2H, m), 7.22~7.28(1H, m), 7.35~7.42(1H, m), 7.37(1H, s), 7.6~7.66(2H, m), 7.75(1H, s), 7.86(1H, d, J=2.8Hz), 8.22(1H, s), 8.24~8.3(1H, m) |
| 13 | CH | F | H | mp: 184~186° C. |
| | | | | ¹HN. M.R. (DMSO-d₆) δ4.79(1H, d, J=14.5Hz), 4.87(1H, d, J=14.5Hz), 6.66(1H, brs), 6.81(1H, brs), 7.1~7.18(2H, m), 7.22~7.28(1H, m), 7.30(1H, brs), 7.32(1H, s), 7.35~7.42(1H, m), 7.86(1H, d, J=2.5Hz). 8.25~8.32(1H, m) |
| 14 | N | Cl | Cl | mp: 188~189° C. |
| | | | | ¹HN. M.R. (DMSO-d₆) δ5.35(1H, d, J=14.4Hz), 5.50(1H, d, J=14.4Hz), 7.2~7.26(1H, m), 7.35~7.44(3H, m), 7.54~7.58(2H, m), 7.68(1H, s), 8.00(1H, d, J=2.5Hz), 8.15~8.22(1H, m), 8.31(1H, s) |
| 15 | CH | Cl | Cl | mp: 238~239° C. |
| | | | | ¹HN. M.R. (DMSO-d₆) δ5.05(1H, d, J=14.4Hz), 5.26(1H, d, J=14.4Hz), 6.67(1H, brs), 6.73(1H, brs), 7.2~7.25(1H, m), 7.23(1H, s), 7.37(1H, s), 7.37~7.42(2H, m), 7.57(1H, d, J=2.5Hz), 7.64(1H, d, J=8.8Hz), 7.98(1H, d, J=2.5Hz), 8.14~8.2(1H, m) |
| 16 | N | Cl | H | mp: 167~168° C. |
| | | | | ¹HN. M.R. (DMSO-d₆) δ5.09(2H, brs), 7.22~7.28(1H, m), 7.35~7.40(2H, m), 7.42(1H, s), 7.6~7.64(2H, m), 7.76(1H, s), 7.87(1H, d, J=2.8Hz), 8.24 (1H, s), 8.24~8.3(1H, m) |
| 17 | CH | Cl | H | mp: 201~203° C. |
| | | | | ¹HN. M.R. (DMSO-d₆) δ4.81(1H, d, J=14.5Hz), 4.86(1H, d, J=14.5Hz), 6.67(1H, s), 6.83(1H, s), 7.22~7.28(1H, m), 7.31(1H, s), 7.35~7.42(4H, m), 7.62~7.66(2H, m), 7.87(1H, d, J=2.5Hz), 8.25~8.32(1H, m) |

EXAMPLES 18–87

The intended compounds prepared in the same manner as in Examples 1–10 are shown collectively in Table 2.

TABLE 2

| Ex. | Intended compound | Physical properties |
|---|---|---|
| 18 | (structure: triazolylmethyl-C(OH)(2,4-difluorophenyl)-thiazole-N=CH-C₆H₄-4-F) | mp: 177~179° C.<br>¹HN.M.R. (CDCl₃) δ5.26 (2H, s), 5.93 (1H, s), 6.78~6.90 (2H, m), 7.11(2H, brt. J=8.7Hz), 7.38(1H, s), 7.65~7.72 (1H, m), 7.80~7.86(2H, m), 7.87(1H, s), 8.10(1H, s) |
| 19 | (structure: triazolylmethyl-C(OH)(2,4-difluorophenyl)-thiazole-N=CH-C₆H₄-4-Me) | mp: 124~126° C.<br>¹HN.M.R. (CDCl₃) δ2.39 (3H, s), 5.26(2H, s), 5.86 (1H, s), 6.77~6.87(2H, m), 7.23(2H, brd, J=8.0Hz), 7.38(1H, s), 7.62~7.70(1H, m), 7.75(2H, brd, J=8.0Hz), 7.85(1H, s), 8.10(1H, s) |
| 20 | (structure: triazolylmethyl-C(OH)(2,4-difluorophenyl)-thiazole-N=CH-C₆H₄-4-Cl) | mp: 168~169° C.<br>¹HN.M.R. (CDCl₃) δ5.26(2H, s), 5.95(1H, s), 6.77~6.88 (2H, m), 7.39(2H, brd, J=8.8Hz), 7.43(1H, s), 7.65~7.71 (1H, m), 7.79(2H, brd, J=8.8Hz), 7.86(1H, s), 8.09(1H, s) |

TABLE 2-continued

| Ex. | Intended compound | Physical properties |
|---|---|---|
| 21 | (2,4-difluorophenyl / triazole / thiazole / 4-cyanophenyl compound) | mp : 195~198° C.<br>$^1$HN.M.R. (CDCl$_3$) δ5.24(1H, d, J=14.5Hz), 5.28(1H, d, J=14.5Hz), 6.05(1H, s), 6.78~6.90(2H, m), 7.60(1H, s), 7.68~7.74(1H, m), 7.71(2H, brd, J=8.5Hz), 7.89(1H, s), 7.97(2H, brd, J=8.5Hz), 8.11(1H, s) |
| 3 | (2,4-difluorophenyl / triazole / thiazole / 4-(tetrazol-5-yl)phenyl compound) | mp : 252~254° C.<br>$^1$HN.M.R. (DMSO-d$_6$) δ5.27(2H, s), 7.0~7.05(1H, m), 7.18~7.25(1H, m), 7.43(1H, s), 7.50~7.57(1H, m), 7.72(1H, s), 8.12(2H, brd, J=8.5Hz), 8.20(2H, brd, J=8.5Hz), 8.28(1H, s), 8.33(1H, s) |
| 4 | Structural Formula A<br>(2,4-difluorophenyl / triazole / thiazole / 4-(2-methyltetrazol-5-yl)phenyl compound) | mp : 188~191° C.<br>$^1$HN.M.R. (CDCl$_3$) δ4.42(3H, s), 5.27(1H, d, J=14.4Hz), 5.32(1H, d, J=14.4Hz), 5.94(1H, s), 6.79~6.89(2H, m), 7.55(1H, s), 7.65~7.72(1H, m), 7.88(1H, s), 7.99(2H, brd, J=8.6Hz), 8.13(1H, s), 8.20(2H, brd, J=8.6Hz) |
| 4 | Structural Formula B<br>(Isomer of Structural Formula A)<br>(2,4-difluorophenyl / triazole / thiazole / 4-(1-methyltetrazol-5-yl)phenyl compound) | mp : 185~187° C.<br>$^1$HN.M.R. (CDCl$_3$) δ4.22(3H, s), 5.28(2H, brs), 6.02(1H, s), 6.79~6.91(2H, m), 7.61(1H, s), 7.69~7.76(1H, m), 7.82(2H, brd, J=8.2Hz), 7.89(1H, s), 8.06(2H, brd, J=8.2Hz), 8.14(1H, s) |

TABLE 2-continued

| Ex. | Intended compound | Physical properties |
|---|---|---|
| 22 | | mp : 142~143° C.<br>¹HN.M.R. (CDCl₃) δ2.41(3H, d, J=0.9Hz), 5.19(2H, s), 5.75(1H, s), 6.75~6.9(2H, m), 6.85(1H, brs), 7.55~7.65(1H, m), 7.83(1H, s), 8.07(1H, s) |
| 23 | | mp : 217~220° C.<br>¹HN.M.R. (CDCl₃) δ5.25(2H, s), 5.94(1H, s), 6.77~6.9(2H, m), 7.65~7.72(1H, m), 7.79(1H, s), 7.80(1H, d, J=2.2Hz), 7.86(1H, s), 8.11(1H, s), 8.82(1H, d, J=2.2Hz) |
| 24 | | mp : 147~149° C.<br>¹HN.M.R. (CDCl₃) δ2.32(3H, d, J=2.4Hz), 5.14(1H, d, J=14.1Hz), 5.24(1H, d, J=14.1Hz), 5.83(1H, s), 6.78~7.00(4H, m), 7.38~7.44(1H, m), 7.61~7.68(1H, m), 7.87(1H, s), 8.10(1H, s) |
| 25 | | Oily or waxy matter<br>¹HN.M.R. (CDCl₃) δ0.90(3H, t, J=7.0Hz), 1.25~1.40 (4H, m), 1.60~1.75(2H, m), 2.71(2H, t, J=7.9Hz), 5.15 (1H, d, J=14.1Hz), 5.21(1H, d, J=14.1Hz), 5.75(1H, s), 6.76~6.86(3H, m), 7.56~7.62(1H, m), 7.83(1H, s), 8.06(1H, s) |
| 26 | | Oily matter<br>¹HN.M.R. (CDCl₃) δ5.19(2H, s), 6.34(1H, s), 6.78~6.9(2H, m), 7.65~7.7(1H, m), 7.90(1H, s), 7.96(1H, s), 8.12(1H, s) |

TABLE 2-continued
| Ex. | Intended compound | Physical properties |
| --- | --- | --- |
| 27 | 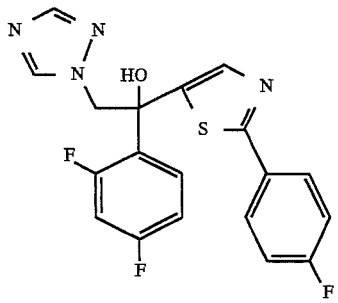 | Solid, amorphous<br>$^1$HN.M.R. (CDCl$_3$) δ4.89(1H, d, J=14.2Hz), 5.22(1H, d, J=14.2Hz), 5.84(1H, s), 6.78~6.90(2H, m), 7.11(2H, brt, J=9.0Hz), 7.61(1H, d, J=1.6Hz), 7.69~7.75(1H, m), 7.84~7.89(2H, m), 7.88(1H, s), 8.05(1H, s) |
| 28 | 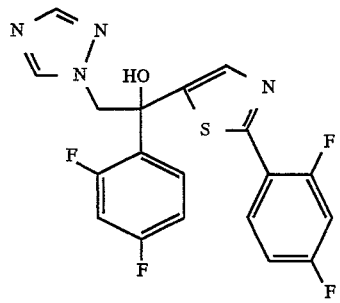 | Solid<br>$^1$HN.M.R. (CDCl$_3$) δ4.91(1H, d, J=14.1Hz), 5.23(1H, d, J=14.1Hz), 5.86(1H, s), 6.78~7.02(4H, m), 7.68~7.76(2H, m), 7.87(1H, s), 8.05(1H, s), 8.18~8.25(1H, m) |
| 29 | 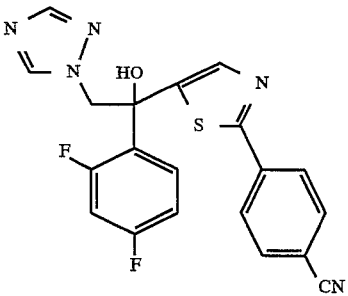 | Solid, amorphous<br>$^1$HN.M.R. (CDCl$_3$) δ4.90(1H, d, J=14.1Hz), 5.22(1H, d, J=14.1Hz), 5.96(1H, s), 6.79~6.91(2H, m), 7.7~7.77(4H, m), 7.89(1H, s), 7.99(2H, brd, J=8.5Hz), 8.06(1H, s) |
| 30 | 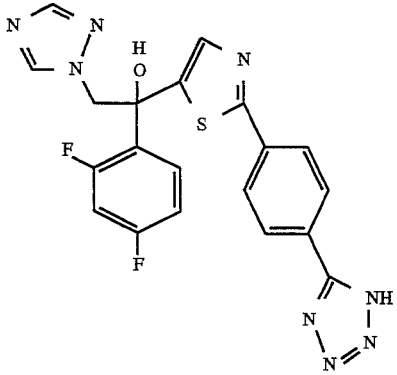 | mp : 129~131° C.<br>$^1$HN.M.R. (DMSO-d$_6$) δ5.08(1H, d, J=14.3Hz), 5.18(1H, d, J=14.3Hz), 6.98~7.05(1H, m), 7.18~7.25(1H, m), 7.25(1H, s), 7.45~7.52(1H, m), 7.73(1H, s), 8.02 (1H, d, J=0.7Hz), 8.11(4H, brs), 8.34(1H, s) |

TABLE 2-continued

| Ex. | Intended compound | Physical properties |
|---|---|---|
| 31 | Structural Formula A 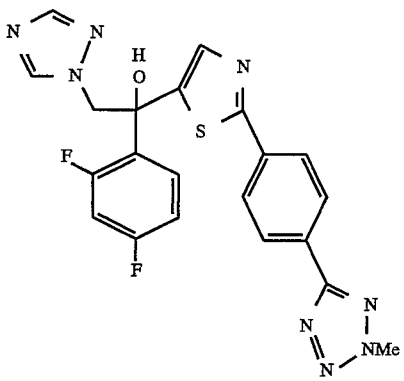 | mp : 147~149° C.<br>$^1$HN.M.R. (CDCl$_3$) δ4.42(3H, s), 4.92(1H, d, J=14.1Hz), 5.24(1H, d, J=14.1Hz), 5.89(1H, s), 6.79~6.91(2H, m), 7.68(1H, d, J=1.5Hz), 7.70~7.77(1H, m), 7.88(1H, s), 8.01(2H, brd, J=8.2Hz), 8.07(1H, s), 8.20(2H, brd, J=8.2Hz) |
| 31 | Structural Formula B (Isomer of Structural Formula A) 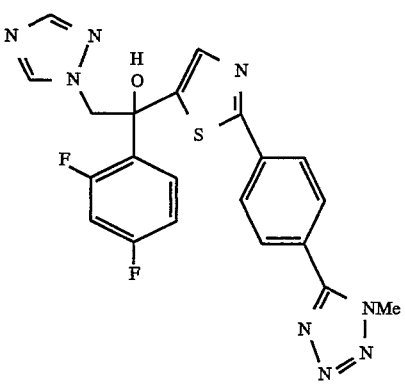 | mp : 113~115° C.<br>$^1$HN.M.R. (CDCl$_3$) δ4.22(3H, s), 4.93(1H, d, J=14.1Hz), 5.24(1H, d, J=14.1Hz), 5.99(1H, s), 6.80~6.92(2H, m), 7.72(1H, d, J=1.6Hz), 7.72~7.78(1H, m), 7.83(2H, brd, J=8.6Hz), 7.89(1H, s), 8.08(1H, s), 8.08(2H, brd, J=8.6Hz) |
| 32 | 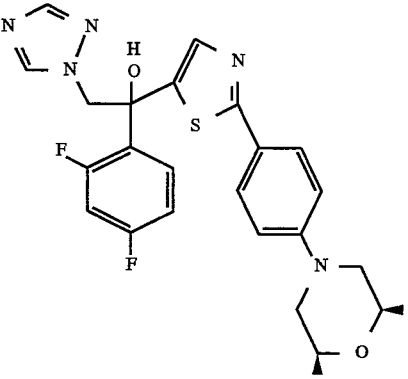 | Oily matter<br>$^1$HN.M.R. (CDCl$_3$) δ1.27(6H, d, J=6.2Hz), 2.48(2H, dd, J=12.1, 10.6Hz), 3.55(2H, dd, J=12.1, 3.1Hz), 3.75~3.83 (2H, m), 4.88(1H, d, J=14.1Hz), 5.21(1H, d, J=14.1Hz), 5.72(1H, s), 6.79~6.9(2H, m), 6.88(2H, brd, J=9.2Hz), 7.51(1H, d, J=1.6Hz), 7.67~7.73(1H, m), 7.76(2H, brd, J=9.2Hz), 7.86(1H, s), 8.04(1H, s) |

TABLE 2-continued

| Ex. | Intended compound | Physical properties |
|---|---|---|
| 33 | | ¹HN.M.R. (CDCl₃) δ4.93(1H, d, J=14.1Hz), 5.19(1H, d, J=14.1Hz), 6.67(1H, brs), 6.78~6.90(2H, m), 7.14(1H, s), 7.28(1H, s), 7.37(2H, d, J=8.2Hz), 7.65(1H, s), 7.70~7.75(1H, m), 7.74(1H, s), 7.81(1H, s), 7.92(2H, d, J=8.2Hz), 8.11(1H, s) |
| 34 | | mp : 170~171° C.<br>¹HN.M.R. (CDCl₃) δ4.92(1H, d, J=14.1Hz), 5.24(1H, d, J=14.1Hz), 5.87(1H, s), 6.80~6.95(2H, m), 7.67(1H, d, J=1.5Hz), 7.71~7.77(1H, m), 7.85(2H, s), 7.89(1H, s), 7.99~8.03(2H, m), 8.07(1H, s), 8.14~8.18(2H, m) |
| 35 | | ¹HN.M.R. (CDCl₃) δ4.87(1H, d, J=14.1Hz), 5.18(1H, d, J=14.1Hz), 6.23(1H, s), 6.79~6.90(2H, m), 7.13(1H, dd, J=1.5, 0.9Hz), 7.38(1H, d, J=1.6Hz), 7.41(1H, t, J=1.5Hz), 7.67~7.73(1H, m), 7.86(1H, s), 8.06(1H, s), 8.07(1H, t, J=0.9Hz) |
| 36 | | mp : 240~242° C.<br>¹HN.M.R (DMSO-d₆) δ3.45~3.57(8H, m), 5.04~5.08(1H, m), 5.20~5.24(1H, m), 6.98~7.16(5H, m), 7.38~7.45(1H, m), 7.58~7.62(2H, m), 8.17(1H, s), 8.88(1H, s) |
| 37 | | mp : 152~153° C.<br>¹HN.M.R. (CDCl₃) δ4.72(1H, d, J=14.1Hz), 5.11(1H, d, J=14.1Hz), 5.75(1H, s), 6.74~6.84(2H, m), 7.10~7.15 (2H, m), 7.40(1H, d, J=1.8Hz), 7.58~7.65(3H, m), 7.82 (1H, s), 7.98(1H, s) |

TABLE 2-continued
| Ex. | Intended compound | Physical properties |
|---|---|---|
| 38 | 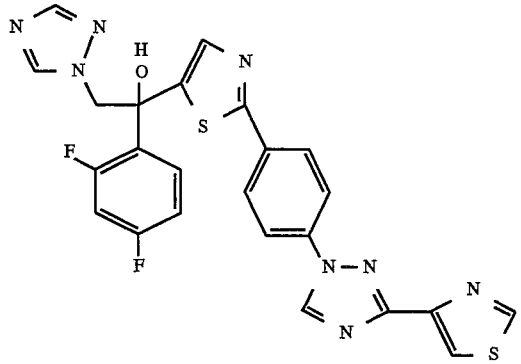 | [1]HN.M.R. (DMSO-d6) δ5.08(1H, d, J=14.3Hz), 5.19(1H, d, J=14.3Hz), 6.9~7.05(1H, m), 7.18~7.28(1H, m), 7.24(1H, s), 7.44~7.52(1H, m), 7.72(1H, s), 7.95~ 8.12(4H, m), 7.99(1H, s), 8.31(1H, d, J=2.0Hz), 8.34 (1H, s), 9.23(1H, d, J=2.0Hz), 9.46(1H, s) |
| 39 (5) | 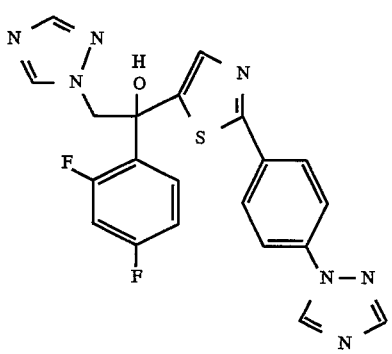 | [1]HN.M.R. (DMSO-d6) δ5.07(1H, d, J=14.4Hz), 5.18(1H, d, J=14.4Hz), 6.97~7.03(1H, m), 7.18~7.25(1H, m), 7.23(1H, s), 7.44~7.5(1H, m), 7.72(1H, s), 7.97(2H, brd, J=8.8Hz), 8.06(2H, brd, J=8.8Hz), 8.27(1H, s), 8.33(1H, s), 9.38(1H, s) |
| 40 | 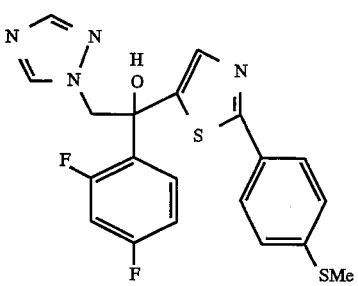 | mp : 142~144° C. <br> [1]HN.M.R. (DMSO-d6) δ2.50(3H, s), 5.04(1H, d, J=14.3Hz), 5.16(1H, d, J=14.3Hz), 6.96~7.02(1H, m), 7.15~7.25(1H, m), 7.18(1H, s), 7.31(2H, brd, J=8.2Hz), 7.42~7.5(1H, m), 7.71(1H, s), 7.79(2H, brd, J=8.2Hz), 7.89(1H, s), 8.32(1H, s) |
| 41 | 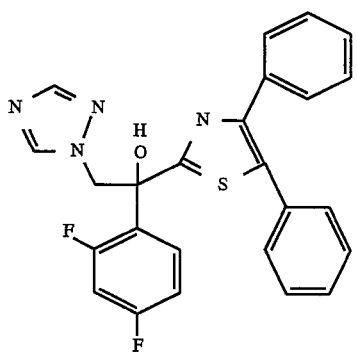 | mp : 162~163° C. <br> [1]HN.M.R. (CDCl3) δ5.27(2H, s), 5.88(1H, s), 6.8~ 6.9(2H, m), 7.25~7.35(8H, m), 7.45~7.5(2H, m) 7.7~7.78(1H, m), 7.89(1H, s), 8.15(1H, s) |

TABLE 2-continued

| Ex. | Intended compound | Physical properties |
|---|---|---|
| 42 | (structure) | mp : 126~127° C.<br>Elemental Calculated C;54.20, H;3.04 N;16.86<br>analysis Found C;53.92, H;3.10 N;16.68<br>$^1$HN.M.R (CDCl$_3$) δ4.84(1H, d, J=14.1Hz), 5.18(1H, d, J=14.1Hz), 6.19(1H, bs,), 6.78~6.89(m. 2H), 7.02 (1H, dd, J=4.0, 1.8Hz), 7.47(1H, d, J=4.0Hz), 7.71(1H, dt, J=6.4, 9.2Hz), 7.81(1H, s), 8.05(1H, s) |
| 43 | (structure) | Mass MH$^+$ 376 Oily matter<br>$^1$HN.M.R. (DMSO-d$_6$) δ5.02(1H, d, J=14.3Hz), 5.14(1H, d, J=14.3Hz), 6.93~6.99(1H, m), 7.13(1H, d, J=2.7Hz), 7.13~7.29(1H, m), 7.43(1H, d, J=2.7Hz), 7.44~7.50(1H, m), 7.69(1H, s), 7.93(1H, s), 8.31(1H, s) |
| 44 | Structural Formula A<br>(structure) | mp : 135~137° C.<br>$^1$HN.M.R. (CDCl$_3$) δ4.36(3H, s), 4.90(1H, d, J=14.1Hz), 5.23(1H, d, J=14.1Hz), 5.80(1H, s), 6.77~6.87(2H, m), 6.99~7.00(1H, m), 7.27(1H, s), 7.61(1H, d, J=3.9Hz), 7.72(1H, dt, J=9.2, 6.4Hz), 7.84(1H, s), 8.06(1H, s) |
| 44 | Structural Formula B<br>(Isomer of Structural<br>Formula A)<br>(structure) | mp : 179~182° C.<br>$^1$HN.M.R. (CDCl$_3$) δ4.20(3H, s), 5.07(1H, d, J=14.3Hz), 5.18(1H, d, J=14.3Hz), 6.98~7.02(1H, m), 7.18~7.23(1H, m), 7.24(1H, s), 7.45(1H, dd, J=1.3, 3.5Hz), 7.48~7.52(1H, m), 7.72(1H, s), 7.73(1H, d, J=3.5Hz), 8.33(1H, s) |
| 45 | (structure) | mp : 142~145° C.<br>$^1$HN.M.R. (CDCl$_3$) δ5.19(1H, d, J=14.1Hz), 5.30(1H, d, J=14.1Hz), 6.41~6.43(1H, m), 6.79~6.84(1H, m), 6.86~6.92(1H, m), 7.18(1H, d, J=5.3Hz), 7.29(1H, d, J=5.3Hz), 7.65(1H, dt, J=6.4, 9.0Hz), 7.84(1H, s), 8.13(1H, s) |

TABLE 2-continued

| Ex. | Intended compound | Physical properties |
|---|---|---|
| | | Elemental calculated C;54.20, H;3.04 N;16.86<br>analysis  Found    C;54.00, H;2.88 N;16.77 |
| 46 | *(structure: triazole-CH2-C(OH)(2,4-difluorophenyl)-thiophene-tetrazole · HNO3)* | Solid, HNO3 salt 205~210° C.<br>1HN.M.R. (DMSO-d6) δ5.18(1H, d, J=13.9Hz), 5.70(1H, d, J=13.9Hz), 6.82~6.87(1H, m), 7.00~7.06(1H, m), 7.31~7.37(1H, m), 7.33(1H, d, J=5.3Hz), 7.64(1H, d, J=5.3Hz), 7.69(1H, s), 8.25(1H, s)<br>Mass MH+ 376 |
| 47 | Structural Formula A<br>*(structure: triazole-CH2-C(OH)(2,4-difluorophenyl)-thiophene-(methyl-tetrazole) · HCl)* | Oily matter<br>1HN.M.R. (CDCl3) δ4.32(3H, s), 5.19(1H, brd, J=12.0Hz), 5.25(1H, brd, J=12.0Hz), 5.90~6.67(2H,m), 7.33~7.39 (1H, m), 7.36(1H, d, J=5.3Hz), 7.44(1H, d, J=1.1Hz), 7.53(1H, d, J=5.3Hz), 7.69(1H, s), 8.23(1H, s) |
| 47 | Structural Formula B<br>(Isomer of Structural Formula A)<br>*(structure: triazole-CH2-C(OH)(2,4-difluorophenyl)-thiophene-(methyl-tetrazole) · HCl)* | Oily matter<br>1HN.M.R. (CDCl3)δ3.75(3H, s), 5.17(1H, d, J=13.6Hz), 5.20(1H d, J=13.6Hz), 6.52(1H, d, J=1.1Hz), 6.58~6.64 (2H, m), 7.09(1H, d, J=5.3Hz), 7.15(1H, dt, J=6.41, 9.0Hz), 7.50(1H, d, J=5.3Hz), 7.71(1H s), 8.23(1H, s) |
| 48 | *(structure: triazole-CH2-C(OH)(2,4-difluorophenyl)-thiophene-CN)* | mp : 244~245° C.<br>MS : MH+413<br>1HN.M.R. (CDCl3) δ5.13(1H, d, J=14.1Hz), 5.29(1H, d, J=14.1Hz), 7.10~7.17(1H, m), 7.22~7.29(1H, m), 7.49(1H, s), 7.70(1H, dt, J=6.4, 9.0Hz), 7.74(1H, s), 7.90(1H, s), 8.30(1H, s)<br>Calculated C;43.75, H;2.21 N;13.61<br>Found     C;43.44, H;2.03 N;13.51 |

TABLE 2-continued

| Ex. | Intended compound | Physical properties |
|---|---|---|
| 49 | (structure) | mp : 203~208° C.<br>$^1$HN.M.R. (DMSO-d$_6$) δ5.15(1H, d, J=13.9Hz), 5.29(1H, d, J=13.9Hz), 7.01~7.07(1H, m), 7.12(1H, brs), 7.16~7.22(1H, m), 7.20(1H, s), 7.56(1H, dt, J=6.8, 9.0Hz), 7.70(1H, s), 8.30(1H, s) |
| 50 | Structural Formula A<br>(structure) | mp : 191~194° C.<br>MS : MH$^+$470.469<br>$^1$HN.M.R. (CDCl$_3$) δ4.18(3H, s), 5.21(1H, dd, J=3.30, 14.4Hz), 5.48(1H, dd, J=5.0, 14.4Hz), 5.94~6.01(1H, m), 6.81~6.87(2H, m), 7.39~7.46(1H, m), 7.59~7.60 (1H, m), 7.86(1H, brd, J=14.5Hz), 8.03(1H, d, J=3.7Hz)<br>Calculated C;41.03, H;2.59 N;20.94<br>Found    C;40.93, H;2.37 N;20.81 |
| 50 | Structural Formula B<br>(Isomer of Structural Formula A<br>(structure) | Solid<br>mp : 88~92° C.<br>$^1$HN.M.R. (CDCl$_3$) δ4.09(3H, s), 5.24(1H, d, J=14.1Hz), 5.48(1H, d, J=14.1Hz), 6.13~6.20(1H, m), 6.82~6.91 (2H, m), 7.41~7.47(1H, m), 7.48(1H, s), 7.87~7.90(1H, m), 8.07(1H, s) |
| 51 | (structure) | mp : 54~58° C.<br>(Solid) IR 2231cm−1<br>$^1$HN.M.R (CDCl$_3$)δ4.81(1H, d, J=13.9Hz), 5.19(1H, d, J=13.9Hz), 6.00(1H, s), 6.80~6.89(2H, m), 7.15(1H, brs), 7.67~7.73(1H, m), 7.86(1H, brs), 7.88(1H, s), 8.05(1H, s)<br>Calculated C;54.20, H;3.04 N;16.86<br>Found    C;54.04, H;3.23 N;16.74 |

TABLE 2-continued

| Ex. | Intended compound | Physical properties |
|---|---|---|
| 52 | 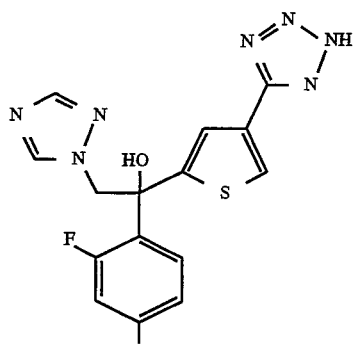 | HCl salt<br>mp : 218~221° C.<br>Oily matter<br>$^1$HN.M.R. (CDCl$_3$) δ5.01(1H, d, J=14.3Hz), 5.22(1H, d, J=14.3Hz), 6.73~6.87(2H, m), 7.67~7.73(1H, m), 7.75(1H, brs), 8.04(1H, s), 8.17(1H, brs), 8.21(1H, s) |
| 53 | Structural Formula A<br>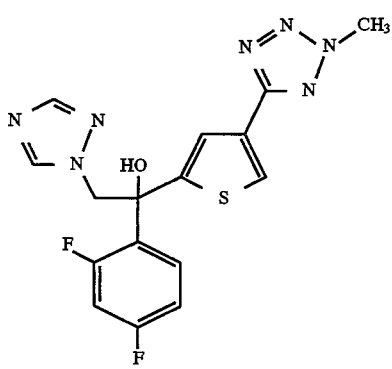 | mp : 118~120° C.<br>$^1$HN.M.R. (CDCl$_3$) δ4.36(3H, s), 4.90(1H, d, J=14.3Hz), 5.25(1H, d, J=14.3Hz), 5.73(1H, s), 6.77~6.89(2H, m), 7.52(1H, brs), 7.72(1H, dt, J=6.4, 9.3Hz), 7.86(1H, s), 7.97(1H, brs), 8.05(1H, s) |
| 53 | Structural Formula B<br>(Isomer of Structural Formula A)<br>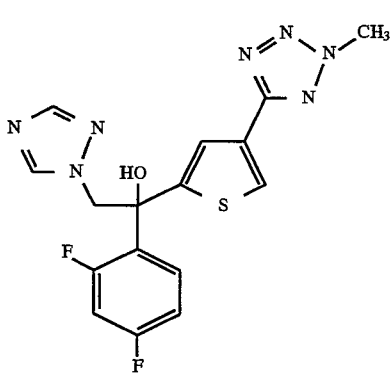 | mp : 117~120° C.<br>$^1$HN.M.R. (CDCl$_3$) δ4.19(3H, s), 4.99(1H, d, J=14.3Hz), 5.25(1H, d, J=14.3Hz), 5.95(1H, s), 6.81~6.87(2H, m), 7.50(1H, brs), 7.73(1H, dt, J=6.4, 9.2Hz), 7.77(1H, brs), 7.88(1H, s), 8.07(1H, s) |
| 54 | 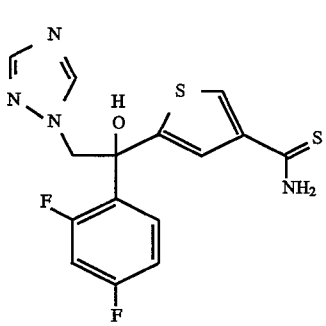 | Yellow solid<br>$^1$HN.M.R. (CDCl$_3$) δ4.85(1H, d, J=14.5Hz), 5.21(1H, d, J=14.5Hz), 5.83(1H, s), 6.77~6.87(2H, m), 7.14(1H, brs), 7.43(1H, brs), 7.50(1H, brs), 7.68(1H, dt, J=6.4, 9.2Hz), 7.83(1H, s), 7.84(1H, s), 8.04(1H, s) |

TABLE 2-continued

| Ex. | Intended compound | Physical properties |
| --- | --- | --- |
| 55 | | mp : 112~115° C.<br>$^1$HN.M.R. (CDCl$_3$) δ4.88(1H, d, J=14.4Hz), 5.27(1H, d, J=14.4Hz), 5.65(1H, brs), 5.80(1H, s), 6.79~6.89(2H, m), 7.19,(1H, brs), 7.42(1H, brs), 7.70~7.76(1H, m), 7.77(1H, brs), 7.87(1H, s), 8.06(1H, s), 8.06(1H, s) |
| 56 | | mp : 172~173° C.<br>$^1$HN.M.R. (CDCl$_3$) δ4.89(1H, d, J=14.0Hz), 5.26(1H, d, J=14.0Hz), 5.87(1H, s), 6.80~6.89(2H, m), 7.47(1H, s), 7.72(1H, dt, J=6.4, 9.3Hz), 7.83(1H, s), 7.87(1H, s), 7.90(1H, s), 8.07(1H, s)<br>Calculated C;52.03, H;2.67 N;16.86<br>Found    C;51.93, H;2.75 N; 16.79 |
| 57 | | mp : 162~165° C.<br>$^1$HN.M.R. (DMSO-d$_6$) δ5.11(1H, d, J=14.1Hz), 5.19(1H, d, J=14.1Hz), 6.98~7.03(1H, m), 7.21~7.26(1H, m), 7.50(1H, dt, J=7.0, 9.2Hz), 7.67(1H, s), 7.79(1H, s), 8.22(1H, s), 8.47(1H, s), 8.49(1H, s) |
| 58 | Structural Formula A | mp : 91~94° C. (Solid)<br>MS : MH$^+$473<br>$^1$HN.M.R. (CDCl$_3$) δ4.49(3H, s), 4.90(1H, d, J=14.5Hz), 5.27(1H, d, J=14.5Hz), 5.85(1H, s), 6.79~6.90(2H, m), 7.45(1H, t, J=1.5Hz), 7.73(1H, dt, J=6.4, 9.2Hz), 7.84 (1H, d, 1.5Hz), 7.88(1H, s), 8.07(1H, s), 8.23(1H, s) |

TABLE 2-continued
| Ex. | Intended compound | Physical properties |
|---|---|---|
| 58 | Structural Formula B (Isomer of Structural Formula A) 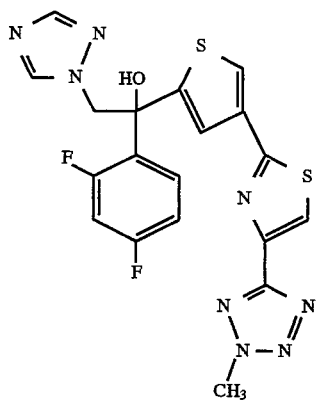 | mp : 178~180° C.<br>¹HN.M.R. (CDCl₃) δ4.44(3H, s), 4.88(1H, d, J=13.6Hz), 5.29(1H, d, J=13.6Hz), 5.71(1H, s), 6.77~6.87(2H, m), 7.57(1H, t, J=1.5Hz), 7.77(1H, dt, J=6.4, 9.2Hz), 7.87(1H, s), 7.88(1H, d, J=1.5Hz), 8.03(1H, s), 8.06(1H, s) |
| 59 | 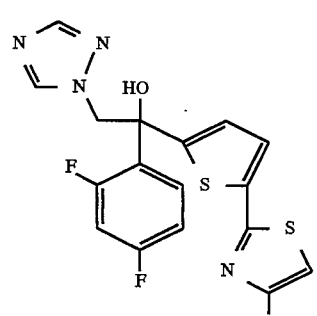 | mp : 189~191° C.<br>¹HN.M.R. (CDCl₃) δ4.89(1H, d, J=14.7Hz), 5.21(1H, d, J=14.7Hz), 5.84(1H, s), 6.77~6.89(2H, m), 6.98(1H, dd, J=1.7, 4.0Hz), 7.41(1H, d, J=4.0Hz), 7.74(1H, dt, J=6.4, 9.0Hz), 7.87(1H, s), 7.88(1H, s), 8.06(1H, s) |
| 60 | 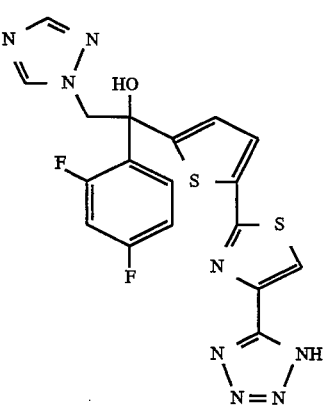 | mp : 140~147° C.<br>¹HN.M.R. (DMSO-d₆) δ5.06(1H, d, J=14.7Hz), 5.15(1H, d, J=14.7Hz), 6.98~7.02(1H, m), 7.14(1H, s), 7.17~7.23(1H m), 7.22(1H, d, J=4.0), 7.49(1H, dt, J=6.8, 9.0Hz), 7.64~7.66(1H, m), 7.71(1H, s), 8.22~8.27 (1H m), 8.32(1H, s) |

TABLE 2-continued

| Ex. | Intended compound | Physical properties |
|---|---|---|
| 61 | | (Solid)<br>Minor component<br>$^1$H N.M.R. (CDCl$_3$)δ4.44(3H, s), 4.90(1H, d, J=14.2Hz), 5.22(1H, d, J=14.2Hz), 5.70(1H, s), 6.78~6.90(2H, m), 6.98~6.99(1H, m), 7.46(1H, d, J=4.0Hz), 7.71~7.79(1H, m), 7.88(1H, s), 8.02(1H, s), 8.06(1H, s)<br>Major component<br>$^1$H N.M.R. (CDCl$_3$)δ4.50(3H, s), 4.90(1H, d, J=14.2Hz), 5.24(1H, d, J=14.2Hz), 5.90(1H, s), 6.78~6.90(2H, m), 6.98(1H, dd, J=1.8, 4.0Hz), 7.42(1H, d, J=4.0Hz), 7.71~7.79(1H, m), 7.89(1H, s), 8.07(1H, s), 8.23(1H, s) |
| 62 | | mp : 166~166.5° C.<br>$^1$H N.M.R. (CDCl$_3$)δ 5.27(1H, d, J=14.1Hz), 5.37(1H, d, J=14.1Hz), 6.26(1H, s), 6.77~6.83(1H, m), 6.86~6.91(1H, m), 7.61(1H, dd, J=1.7, 8.4Hz), 7.74(1H, dt, J=6.4, 9.0Hz), 7.88(1H, s), 7.95(1H, d, J=8.4Hz), 8.17 (1H, s), 8.28(1H, s)<br>Calculated C;50.71, H;2.60 N;13.14<br>Found     C;50.57, H;2.58 N;12.89 |
| 63 | | mp : 130~131° C.<br>$^1$H N.M.R. (CDCl$_3$) δ5.32(2H, q, J=14.3Hz), 6.05(1H, s), 6.77~6.89(2H, m), 7.26~7.40(1H, m), 7.46~7.50(1H, m), 7.70(1H, dt, J=6.4, 8.9Hz), 7.83~7.85(1H, m), 7.86(1H, s), 7.99~8.02(1H, m), 8.15(1H, s)<br>Calculated C;55.31, H;3.60 N;15.18<br>Found     C;55.21, H;3.36 N;15.03 |
| 64 | | mp : 170~172° C.<br>$^1$H N.M.R. (CDCl$_3$) δ5.26(1H, d, J=14.0Hz)5.35(1H, d, J=14.0Hz), 6.33(1H, s), 6.78~6.83(1H, m), 6.87~6.92(1H, m), 7.72(1H, dd, J=1.4Hz, 8.3Hz), 7.89(1H, s, 8.07(1H, dd, J=8.3Hz, 0.4Hz), 8.16(1H, s), 8.18(1H, dd, J=0.4Hz, 1.4Hz)<br>MS : MH$^+$= 384 |
| 65 | | mp : 182~186° C.<br>$^1$H N.M.R. (CDCl$_3$) δ4.42(3H, s), 5.30(1H, d, J=14.0Hz), 5.36(1H, d, J=14.0Hz), 6.18(1H, s), 6.78~6.88(2H, m), 7.48~7.55(1H, m), 7.72(1H, s), 7.78(1H, s), 8.19(1H, dd, J=0.4Hz, 8.8Hz), 8.31(1H, dd, J=1.6Hz, 8.8Hz), 8.66(1H, d, J=0.4Hz)<br>MS : MH$^+$= 441 |

TABLE 2-continued

| Ex. | Intended compound | Physical properties |
|---|---|---|
| 66 | | Solid<br>¹HN.M.R. (CDCl₃) δ5.26(1H, d, J=14.1Hz), 5.34(1H, d, J=14.1Hz), 6.20(1H s), 6.77~6.83(1H, m), 6.86~6.90(1H, m), 7.25(1H, brs), 7.66(1H, brs), 7.69~7.74 (1H, m), 7.80(1H, s), 7.90(1H, dd, J=2.0Hz, 8.8Hz), 7.98(1H, dd, J=0.4Hz, 8.8Hz), 8.14(1H, s), 8.46(1H, dd J=0.4Hz, 2.0Hz) |
| 67 | | mp : 162~166° C.<br>MS : MH⁺= 442<br>¹HN.M.R. (CDCl₃)δ5.29(1H, d, J=14.2Hz), 5.35(1H, d, J=14.2Hz), 6.12(1H, s), 6.78~6.83(1H, m), 6.85~6.91(1H, m), 7.37(1H, d, J=3.4Hz), 7.70~7.76(1H, m), 7.88(1H, s), 7.88(1H, d, J=3.4Hz), 8.03(1H, dd, J=0.8Hz, 8.4Hz), 8.06(1H, dd, J=1.6Hz, 8.4Hz), 8.16(1H, s), 8.48(1H, dd, J=0.8Hz, 1.6Hz) |
| 68 | | mp : 213~215° C.<br>MS : MH⁺= 456<br>¹HN.M.R. (CDCl₃) δ2.51(3H, s), 5.30(1H, d, J=14.4Hz), 5.33(1H, d, J=14.4Hz), 6.10(1H, s), 6.78~6.90(2H, m), 6.91(1H, s), 7.69~7.76(1H, m), 7.87(1H, s), 8.01(1H, s), 8.02(1H, s), 8.16(1H, s), 8.45(1H, s) |
| 69 | | mp : 232~233° C.<br>MS : MH⁺= 552<br>¹HN.M.R. (CDCl₃)δ5.30(1H, d, J=14.0Hz), 5.35(1H, d, J=14.0Hz), 6.13(1H, s), 6.79~6.82(1H, m), 6.87~6.91(1H, m), 7.42(2H, d, J=8.8Hz), 7.49(1H, s), 7.71~7.77(1H, m), 7.88(1H, s), 7.94(2H, d, J=8.8Hz), 8.05 (1H, dd, J=0.4Hz, 8.4Hz), 8.12(1H, dd, J=1.8Hz. 8.4Hz), 8.17(1H, s), 8.55(1H, dd, J=0.4Hz, 1.8Hz) |
| 70 | | mp : 158~160° C.<br>¹HN.M.R. (CDCl₃) δ2.46(3H, s), 5.26(1H, d, J=14.1Hz), 5.32(1H, d, J=14.1Hz), 5.99(1H, s), 6.72~6.88(2H, m), 7.28(1H, dd, J=8.5, 1.6Hz), 7.61(1H, d, J=1.6Hz), 7.63~7.71(1H, m), 7.84(1H, s), 7.87(1H, d, J=8.Hz), 8.13(1H, s) |

TABLE 2-continued

| Ex. | Intended compound | Physical properties |
|---|---|---|
| 71 | | mp : 141~142° C.<br>$^1$HN.M.R. (CDCl$_3$) δ5.26(1H, d, J=14.1Hz), 5.33(1H, d, J= 14.1Hz), 6.13(1H, s), 6.77~6.83(1H, m), 6.85~ 6.90(1H, m), 7.44(1H, dd, J=8.8, 1.6Hz), 7.68~7.74(1H, m), 7.81(1H, d, J=1.6Hz), 7.87(1H, s), 7.90(1H, d, J=8.8Hz), 8.14(1H, s) |
| 72 | | mp : 139~140° C.<br>$^1$HN.M.R. (CDCl$_3$) δ5.28(1H, d, J=14.1Hz), 5.32(1H, d, J= 14.1Hz), 6.16(brs), 6.72~6.82(1H, m), 6.83~6.90(1H, m), 7.20(1H, ddd, J=9.0, 9.0, 2.8Hz), 7.50(1H, dd, J=8.4, 2.8Hz), 7.64~7.74(1H, m), 7.84(1H, s), 7.93(1H, dd, J=9.0, 5.2Hz), 8.13(1H, s) |
| 73 | | $^1$HN.M.R. (CDCl$_3$) δ1.75~2.20(1H, brs), 5.28(1H, d, J=14.1Hz), 5.36(1H, d, J=14.1Hz), 6.74~6.84(1H, m), 6.84~6.90(1H, m), 7.16(1H, d, J=0.8Hz), 7.25~7.28(1H, m), 7.47(1H dd, J=8.8, 2.2Hz), 7.68~7.76(1H, m), 7.77~7.81(1H, m), 7.80(1H, d, J =2.2Hz), 7.82(1H, s), 8.07(1H, d, J=8.8Hz), 8.16(1H, s) |
| 74 | | mp : 175~177° C.<br>$^1$HN.M.R. (CDCl$_3$) δ3.16~3.20(4H, m), 3.86~3.90(4H, m), 5.24(1H, d, J=14.3Hz), 5.32(1H, d, J=14.3Hz), 5.95(1H, s), 6.74~6.89(2H, m), 7.12(1H, dd, J=9.2, 2.5Hz), 7.23(1H, d, J=2.5Hz), 7.63~7.70(1H, m), 7.85(1H, s), 7.86(1H, d, J= 9.2Hz), 8.13(1H, s) |
| 75 | | mp : 148~149° C.<br>$^1$HN.M.R.(CDCl$_3$) δ5.29(1H, d, J=14.2Hz), 5.34(1H, d, J=14.2Hz), 6.24(1H, brs), 6.76~6.83(1H, m), 6.84~ 6.90(1H, m), 7.68~7.75(1H, m), 7.83(2H, brs), 7.85 (1H, s), 8.07(1H, d, J=8.8Hz), 8.16(1H, brs), 8.24(1H, dd, J=8.8, 2.0Hz), 8.54(1H, d, J=2.0Hz) |

TABLE 2-continued

| Ex. | Intended compound | Physical properties |
|---|---|---|
| 76 | | mp : 207~209° C.<br>$^1$HN.M.R. (CDCl$_3$) δ5.28(1H, d, J=14.1Hz), 5.36(1H, d, J=14.1Hz), 6.42(1H, brs), 6.76~6.84(1H, m), 6.84~6.91 (1H, m), 7.69~7.77(1H, m), 7.80(1H, dd, J=8.8, 2.0Hz), 7.84(1H, s), 7.85(1H, d, J=1.6Hz), 8.03(1H, d, J=1.6Hz), 8.10(1H, d, J=8.8Hz), 8.18(1H, s), 8.23(1H, d, J=2.0Hz) |
| 77 | | Oily matter<br>$^1$HN.M.R.(CD$_3$OD) δ5.37(1H, d, J=14.5Hz), 5.44 (1H, d, J=14.5Hz), 6.93~7.02(2H, m), 7.63~7.70(1H, m), 7.73(1H, s), 8.42(1H, s), 8.63(1H, d, J=2.8Hz), 8.74(1H, d, J=2.8Hz) |
| 78 | | Oily matter<br>$^1$HN.M.R. (CDCl$_3$) δ5.26(1H, d, J=14.1Hz), 5.36(1H, d, J=14.1Hz), 6.23(1H, s), 6.77~6.92(2H, m), 7.43(1H, dd, J=8.2, 4.5Hz), 7.73~7.80(1H, m), 7.88(1H, s), 8.16(1H, s), 8.23(1H, dd, J=8.2, 1.6Hz), 8.57(1H, dd, J=4.5, 1.6Hz) |
| 79 | | mp : 199~201° C.<br>$^1$HN.M.R. (CDCl$_3$) δ5.23(1H, d, J=14.4Hz), 5.32(1H, d, J=14.4Hz), 6.30(1H, s)6.76~6.82(1H, m),, 6.87~6.91(1H, m), 7.42(1H, d, J=8.4Hz), 7.73~7.79(1H, m), 7.88(1H, s), 8.15(1H, s), 8.15(1H, d, J=8.4Hz) |
| 80 | | Amorphous<br>$^1$HN.M.R. (CDCl$_3$) δ5.25(1H, d, J=14.4Hz), 5.36(1H, d, J=14.4Hz), 6.33(1H, s), 6.89~6.94(1H, m), 7.22(1H, s, (br)), 7.49(1H, d, J =8.8Hz), 7.67(1H, brs), 7.76~7.82(1H, m), 7.90(1H, s), 8.18(1H, s), 8.32(1H, d, J=8.8Hz), 8.36(1H, brs),<br>MS : MH$^+$ = 427 |

TABLE 2-continued

| Ex. | Intended compound | Physical properties |
|---|---|---|
| 81 | | mp : 144~146° C.<br>$^1$H N.M.R. (CDCl$_3$) δ3.97(3H, s), 5.23(1H, d, J=14.2Hz), 5.31(1H, d, J=14.2Hz), 6.04(1H, s), 6.77~6.90(2H, m), 6.84(1H, d, J=8.8Hz), 7.63~7.74(1H, m), 7.87(1H, s), 8.06(1H, d, J=8.8Hz), 8.14(1H, s) |
| 82 | | mp : 112~115° C.<br>$^1$H N.M.R. (CDCl$_3$) δ4.95(1H, d, J=14.4Hz), 5.28(1H, d, J=14.4Hz), 5.69(1H, s), 6.78~6.88(2H, m), 7.15(1H, d, J=1.1Hz), 7.29~7.36(2H, m), 7.68~7.79(3H, m), 7.85(1H, s), 8.06(1H, s) |
| 83 | | mp : 186~189° C.<br>IR 2227 cm$^+$<br>$^1$H N.M.R. (CDCl$_3$) δ4.95(1H, d, J=14.2Hz), 5.27(1H, d, J=14.2Hz), 5.97(1H, s), 6.58~6.90(2H, m), 7.24(1H, brs), 7.26(1H, s), 7.51~7.54(1H, m), 7.76(1H, dt, J=6.4, 9.2Hz), 7.87(1H, s), 7.87(1H, d, J=8.4Hz), 8.01 (1H, s), 8.07(1H, s)<br>MS : MH$^+$ = 383 |
| 84 | | mp : 122~127° C.<br>$^1$H N.M.R. (DMSO-d$_6$) δ5.17(1H, d, J=14.3Hz), 5.29(1H, d, J=14.3Hz), 6.97~7.03(1H, m), 7.16~7.21(1H, m), 7.51(1H, dt, J=6.8, 9.3Hz), 7.69(1H, s), 7.81(1H, s), 7.98(1H, brd, J=8.4Hz), 8.12(1H, d, J=8.4Hz), 8.50(1H, s), 8.53(1H, s)<br>MS : MH$^+$ = 426 |

TABLE 2-continued

| Ex. | Intended compound | Physical properties |
|---|---|---|
| 85 | Structural Formula A 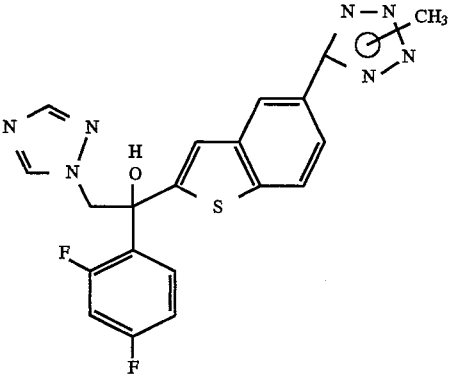 | mp : 162–166° C.<br>$^1$HN.M.R. (CDCl$_3$) δ4.42(3H, s), 4.98(1H, d, J=14.1Hz), 5.31(1H, d, J=14.1Hz), 5.80(1H, s), 6.79–6.85(2H, m), 7.25(1H, brs), 7.75(1H, dt, J=6.4, 9.2Hz), 7.87(1H, s), 7.88(1H, d, J=8.4Hz), 8.08(1H, dd, J=1.7, 8.4Hz), 8.08 (1H, s), 8.49(1H, d, J=1.7Hz)<br>MS : MH$^+$ = 440 |
| 85 | Structural Formula B (Isomer of Structural Formula A) 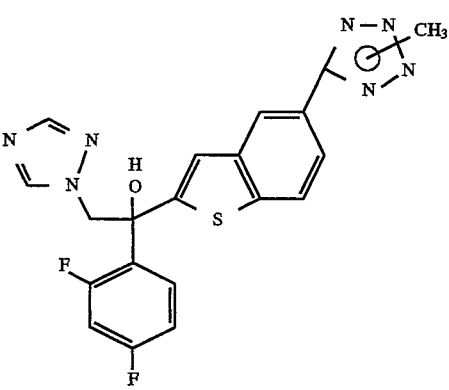 | mp : 105–110° C.<br>$^1$HN.M.R. (CDCl$_3$)δ4.19(3H, s), 4.49(1H, d, J=14.3Hz), 5.29(1H, d, J=14.3Hz), 5.97(1H, s), 6.79–6.91(2H, m), 7.28(1H, brs), 7.64(1H, dd, J=1.7, 8.4Hz), 7.77(1H, 1H, dt, J=6.4, 9.2Hz), 7.88(1H, s), 7.96(1H, d, J=8.4Hz), 8.05(1H, d, J=1.7Hz), 8.10(1H, s)<br>MS : MH$^+$ = 440 |
| 86 | 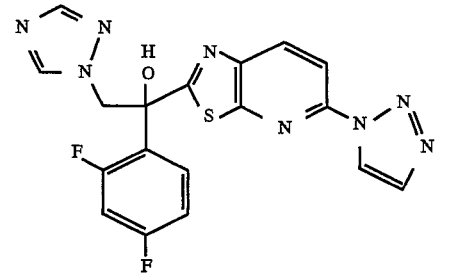 | $^1$HN.M.R. (CDCl$_3$)δ5.27(1H, d, J=14.0Hz), 5.37(1H, d, J=14.0Hz), 6.35(1H, s), 6.79–6.85(1H, m), 6.89–6.94(1H, m), 7.76–7.82(1H, m), 7.85(1H, d, J=1.2Hz), 7.90(1H, s), 8.19(1H, s), 8.37(1H, d, J=8.8Hz), 8.41 (1H, d, J=8.8Hz), 8.61(1H, d, J=1.7Hz)<br>MH$^+$ = 427 |
| 87 | 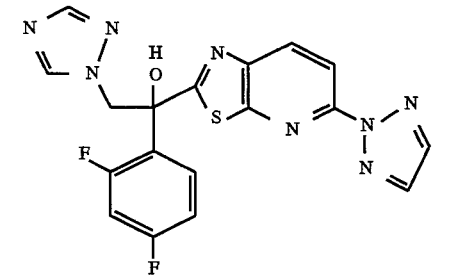 | $^1$HN.M.R. (CDCl$_3$)δ5.28(1H, d, J=10Hz), 5.34(1H, d, J=10 Hz), 6.29(1H, s), 6.78–6.84(1H, m), 6.88–6.94(1H, m), 7.75–7.82(1H, m), 7.89(1H, s), 7.93(2H, s), 8.18(1H, s), 8.26(1H, d, J=9.0Hz), 8.39(1H, d, J=9.0Hz)<br>MH$^+$ = 427 |

EXPERIMENTAL EXAMPLE 1

Five-membered Groups of ICR mice were infected through their tail veins with a *Candida albicans* MCY8622 strain (2×10$^6$ cfu/mouse). After 1 hour, compounds [represented by the general formula (III)] shown in Table 3 were orally administered in a dose of 2.5 mg or 10 mg per kg of a mouse to the respective groups of mice. Observation was carried out for 7 days to calculate the average number of surviving days in each group. This average number was used as an index indicative of antifungal activity in vivo. Incidentally, the general formula (III) is as follows:

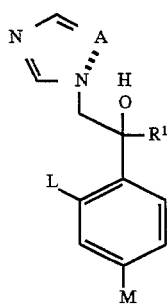

TABLE 3

| R¹ in the general formula (III) | Average number of surviving days (days) | |
|---|---|---|
| | 2.5 mg/kg | 10 mg/kg |
| (thiazolyl-2,4-difluorophenyl) | 3.6 | 7.0 |
| (thiazolyl-4-cyanophenyl) | 7.0 | 7.0 |
| (thiazolyl-2,4-difluorophenyl, isomer) | 6.0 | 7.0 |
| (thiazolyl-4-(N-methyltetrazolyl)phenyl) | 5.6 | 7.0 |

TABLE 3-continued

| R¹ in the general formula (III) | Average number of surviving days (days) | |
|---|---|---|
| | 2.5 mg/kg | 10 mg/kg |
| (thiazolyl-4-methylthiophenyl) | 6.2 | 7.0 |
| (thienyl-cyano) | 6.0 | 6.8 |
| (chlorobenzothiazolyl) | 7.0 | 7.0 |
| (benzothiazolyl-triazolyl) | 6.8 | 7.0 |
| (chlorothiazolopyridyl) | 6.8 | 7.0 |
| (benzothienyl-methyltetrazolyl) | 5.2 | 6.0 |

PREPARATION EXAMPLE 1

Preparation of raw material 1:

(2S,3R)-3-(2,4-Difluorophenyl)-3-hydroxy-2-methyl-4-(1H-1,2,4-triazol-1-yl)butyronitrile Structural formula:

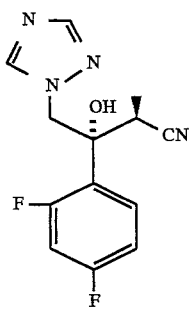

To a solution with 5 g (20.0 mmol) of optically active (2R,3S)-2-(2,4-difluorophenyl)-3-methyl-2-(1H-1,2,4- triazol-1-yl)methyloxirane dissolved in 20 ml of toluene, were added 80 ml of diethylaluminum cyanide (1.0M toluene solution) in a nitrogen atmosphere. The mixture was heated at 50° C. for 12 hours, and 10 ml of water and 120 ml of 1N HCl were succesively added dropwise thereto. The resulting mixture was stirred for 2 hours at room temperature, filtered through a Florisil pad and then subjected to extraction with ethyl acetate. The resultant organic layer was washed 4 times with a liquid obtained by mixing water and saturated saline at a ratio of 1:1, and finally with saturated saline. After the solvent was distilled out under reduced pressure, the residue was washed with diisopropyl ether, thereby obtaining 3.15 g (56.6%) of optically active (2S,3R)-3-(2,4-difluorophenyl)-3-hydroxy-2-methyl-4-(1H-1,2,4-triazol-1-yl)butyronitrile. Physical properties of this product are described below.

mp: 181°–182° C.

NMR: δ Solvent (CDCl$_3$) 1.17(3H,d,J=7.2 Hz), 3.29(1H, q,J=7.2 Hz), 4.82(1H,d,J=14.0 Hz), 4.97(1H,d,J=14.0 Hz), 5.44(1H,d,J=0.8 Hz), 6.74–6.82(2H,m), 7.39–7.46(1H,m), 7.83(1H,s), 7.84(1H,s).

MS: MH$^+$=279.

PREPARATION EXAMPLE 2

Preparation of raw material 1 by another process:

Ytteribium chloride hexahydrate in an amount of 388 mg (1 mmol) was left over for 6 hours at 120° C. under reduced pressure. This compound was suspended in 10 ml of tetrahydrofuran in a nitrogen atmosphere, and the suspension was chilled to −78° C. To this suspension, 1.9 ml of n-butyllithium (1.63M hexane solution) were added dropwise, and the resultant mixture was stirred for 5 minutes at room temperature and then chilled to −78° C. To this mixture, 0.8 ml of trimethylsilyl cyanide was gently added dropwise. The resultant mixture was stirred for 10 minutes at −78° C. and then for 5 minutes at room temperature, and then chilled to −78° C. A solution with 128 mg (0.5 mmol) of optically active 2R,3S)-2-(2,4-difluorophenyl)-3-methyl-2-(1H-1,2,4-triazol-1-yl)methyloxirane dissolved in 1 ml of tetrahydrofuran was added dropwise to this mixture, and temperature of the resultant mixture was spontaneously raised to room temperature. A saturated aqueous solution of ammonium chloride was added to this mixture, followed by extraction with ethyl acetate. The resultant organic layer was washed with water and saturated saline. After the solvent was distilled out under reduced pressure, the residue was recrystallized from diethyl ether, thereby obtaining 81 mg (58.2%) of optically active (2S,3R)-3-(2,4-difluorophenyl)-3-hydroxy-2-methyl-4-(1H-1,2,4-triazol-1-yl)butyronitrile.

PREPARATION EXAMPLE 3

Preparation of raw material 1 by another process:

Litium hydride compound in an amount of 478 mg (60.0 mmol) was added to a ice-cooled solution (50 ml) of tetrahydrofuran to suspend the whole. After 10 minutes, 5.4 g (63.5 mmol) of acetonecyanohydrin [(CH$_3$)$_2$C(OH)CN] were added dropwise to the suspension, followed by continuing the stirring for additional 1.5 hours at room temperature. To this mixture were added 5 g (20.0 mmol) of optically active (2R,3S)-2-(2,4-difluorophenyl)-3-methyl-2-(1H-1,2,4-triazol-1-yl)methyloxirane. And, the whole was refluxed for 7 hours. To the resulting reaction solution were added 100 ml of ethyl acetate, followed by the successive washing with 100 ml of water and 50 ml of sodium chloride solution. And, it was then dried over magnesium sulfate. The resulting solution was then filtered. The filtrate was concentrated under reduced pressure. To the concentrate were added 50 ml of diisopropyl ether. The resulting solution was subjected to the filtration to obtain 4.2 g (76.0%) of optically active (2S,3R)3-(2,4-difluorophenyl)-3-hydroxy-2-methyl-4-(1H-1,2,4-triazol-1-yl)butyronitrile.

PREPARATION EXAMPLE 4

Preparation of raw material 2:

Preparation of 2-(2,4-difluorophenyl)-3-thioamide-1-(1H-1,2,4-triazol-1-yl)-2-butanol Structural formula:

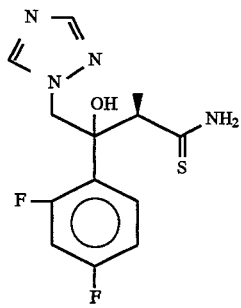

To a racemic modification of the raw material 1 obtained in Preparation Example 1 or 2, i.e., 3-(2,4-difluorophenyl)-3-hydroxy-2-methyl-4-(1H-1,2,4-triazol-1-yl)butyronitrile (14 g), were added 14 ml of H$_2$O and O,O-diethyl dithiophosphate (73 ml), and the resultant mixture was heated and refluxed for 30 minutes. The liquid reaction mixture was cooled back to room temperature, added with H$_2$O and subjected to extraction with AcOEt. The resulting AcOEt layer was washed with H$_2$O and a saturated aqueous solution of NaCl, and dried over MgSO$_4$. Thereafter, the solvent was distilled out. The resultant residue was purified by chromatography on silica gel (SiO$_2$: 300 g, eluted with CH$_2$Cl$_2$, and then with 1% solution of MeOH in CH$_2$Cl$_2$, 2% solution of MeOH in CH$_2$Cl$_2$ and 3% solution of MeOH in CH$_2$Cl$_2$ successively), and then recrystallized from CH$_2$Cl$_2$-IPE, thereby obtaining the intended product (8.1 g). Incidentally, when the optically active substance of the raw material 1 is used in place of the racemic modification of the raw material 1, an optically active raw material 2 can be obtained similarly.

Physical properties of this product are described below.

mp: 164°–167° C.

NMR: δ solvent (CDCl$_3$) 1.11(3H,d,J=7.1 Hz), 3.69–3.72 (1H,m), 4.55(1H,d,J=14.3 Hz), 5.08(1H,d,J=14.3 Hz), 6.71–6.80(2H,m), 7.42–7.48(1H,m), 7.80(1H,brs), 7.94(1H, s), 8.41(1H,brs).

MS: MH$^+$=313.

PREPARATION EXAMPLE 5

Preparation of raw material 3:

Preparation of 2-bromo-4'-cyanoacetophenone

Structural formula:

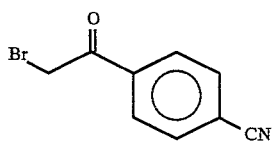

4'-Cyanoacetophenone (10 g) was dissolved in 100 ml of CHCl$_3$, and 1 ml of 48% HBr was added to the resultant solution. To the mixture, a solution of Br$_2$ (3.7 ml) in CHCl$_3$ (10 ml) was added dropwise at room temperature. After stirring for 2 hours at room temperature, a saturated aqueous solution of NaHCO$_3$ was added to the liquid reaction mixture to neutralize it. The CHCl$_3$ layer was washed with H$_2$O and then a saturated NaCl solution and dried over MgSO$_4$. Thereafter, CHCl$_3$ was distilled out. The resulting solid matter was recrystallized from AcOET-nHex, thereby obtaining the intended compound (3.49 g). Physical properties of this product are described below.

mp: 82°–84° C.

NMR: δ solvent (CDCl$_3$) 4.44(2H,s), 7.81–7.84(2H,m), 8.09(1H,d,J=8 Hz), 8.23(1H,d,J=8 Hz).

PREPARATION EXAMPLE 6

Preparation of raw material 4:

Preparation of 2-ethyl-6-chlorobenzothiazole

Structural formula:

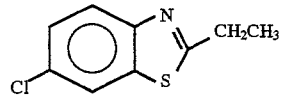

2-Amino-5-chlorothiophenol (2.618 g) was dissolved in N-methylpyrrolidone (6 ml), and propionyl chloride (1.57 ml) was added to the solution, followed by heating at 130° C. for 1.5 hours. Ethyl acetate and an aqueous solution of sodium hydrogencarbonate were added to the liquid reaction mixture to separate the mixture into liquids. The resulting organic layer was washed with water, dried and concentrated. The residue was purified through a silica gel column (hexane:ethyl acetate=20:1), thereby obtaining 2-ethyl-6-chlorobenzothiazole (2.3 g). Physical properties of this product are described below.

State: Solid.

NMR: δ solvent (CDCl$_3$) 1.47(3H,t,J=7.4 Hz), 3.14(2H, q,J=7.4 Hz), 7.40(1H,dd,J=2.0 Hz,8.8 Hz), 7.81(1H,d,J=2.0 Hz), 7.86(1H,d,J=8.8 Hz).

PREPARATION EXAMPLE 7

Preparation of raw material 5:

Preparation of 2-ethyl-6-1,2,3-triazol-2-yl)-benzothiazole

Structural formula:

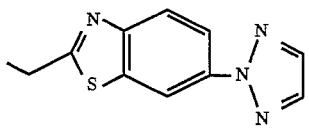

1H-1,2,3-Triazole (10.0 g) was dissolved in dimethylformamide (280 ml), and a 60% dispersion of sodium hydride (5.79 g) in mineral oil was added little by little to the solution over 10 minutes. To this mixture, a solution of 4-fluoronitrobenzene (18.6 g) in dimethylformamide (40 ml) was added dropwise at room temperature, and the resultant mixture was heated and stirred at 50° C. for 9 hours. The reaction mixture was poured into 400 ml of a saturated aqueous solution of ammonium chloride, and 200 ml of water was added thereto. This mixture was subjected to extraction with ethyl acetate (400 ml×1, 200 ml×2), and the ethyl acetate layer was washed with water and then saturated saline, and then dried over anhydrous magnesium sulfate. The organic layer was concentrated under reduced pressure, and purified through a silica gel column (hexane:ethyl acetate=2:1→1:1), thereby obtaining 4-(1,2,3-triazol-2-yl)-nitrobenzene (11.5 g).

4-(1,2,3-Triazol-2-yl)-nitrobenzene (5.75 g) was dissolved in 300 ml of ethanol, and 10% palladium-carbon (0.58 g) and hydrazine hydrate (15.0 g) were added to the solution, followed by heating and refluxing for 5 hours. The reaction mixture was cooled to room temperature and filtered through Celite. The filtrate was concentrated once under reduced pressure, added with 500 ml of water and subjected to extraction with ethyl acetate (200 ml, 100 ml×2). The thus-obtained organic layer was washed with water and then saturated saline, dried over anhydrous magnesium sulfate and then concentrated under reduced pressure, thereby obtaining 4-(1,2,3-triazol-2-yl)-aniline (5.0 g). This product was used in a subsequent reaction without purifying it.

4-(1,2,3-Triazol-2-yl)-aniline (5.0 g) obtained in the preceding reaction was dissolved in 55 ml of acetic acid, and ammonium thiocyanate (6.0 g) was added to the solution. The resultant mixture was stirred while chilling with ice water. To this mixture, a solution of bromine (1.62 ml) in 20 ml of acetic acid was added dropwise over 30 minutes. Thereafter, the mixture was heated to room temperature and stirred for 4 hours at the same temperature.

The reaction mixture was chilled with ice water and added dropwise with concentrated aqueous ammonia, thereby adjusting it to pH 6. Precipitate formed was recovered by filtration, washed with water and then cold ethanol, and dried under reduced pressure, thereby obtaining 2-amino-6-(1,2,3-triazol-2-yl)benzothiazole (5.6 g).

2-Amino-6-(1,2,3-triazol-2-yl)benzothiazole (2.8 g) was dissolved in N,N-dimethylformamide (60 ml), and isoamyl nitrite (8.66 ml) was added to the solution, followed by stirring for 20 minutes at 65° C. The reaction mixture was poured into 100 ml of water and subjected to extraction with ethyl acetate (100 ml×3). The resultant organic layer was washed with water and then saturated saline, dried over anhydrous magnesium sulfate and then concentrated under reduced pressure. The resultant oily substance is purified by column chromatography on silica gel (dichloromethane), thereby obtaining 6-(1,2,3-triazol-2-yl)benzothiazole (1.1 g).

The 6-(1,2,3-triazol-2-yl)benzothiazole (1.1 g) was suspended in ethanol (90 ml), and 12 ml of hydrazine monohydrate were added to the suspension. The resultant mixture was heated and refluxed for 2 hours. After the reaction mixture was concentrated under reduced pressure, 20 ml of water were added thereto, and its pH was adjusted to about 7 with acetic acid. The thus-adjusted mixture was subjected 3 times to extraction with ethyl acetate, and the resultant organic layer was washed with saturated saline, dried over anhydrous magnesium sulfate and then concentrated under reduced pressure, thereby obtaining 2-amino-5-(1,2,3-triazol-2-yl)-thiophenol (2.3 g). This product was used in a subsequent reaction without purifying it.

The 2-amino-5-(1,2,3-triazol-2-yl)-thiophenol (2.3 g) was dissolved in N-methylpyrrolidone (8 ml), and propionyl chloride (0.472 ml) was added to the solution, followed by heating and stirring at 70° C. for 5 hours. The reaction mixture was poured into a saturated aqueous solution of sodium hydrogencarbonate, and subjected to extraction with dichloromethane. The resultant organic layer was dried over anhydrous magnesium sulfate, concentrated under reduced pressure and then purified through a silica gel column (hexane-ethyl acetate=4:1→1:1), thereby obtaining the intended compound, 2-ethyl-6-(1,2,3-triazol-2-yl) benzothiazole (940 mg). Physical properties of this product are described below.

State: Solid.

NMR: δ solvent (CDCl$_3$) 1.49(3H,t,J=7.7 Hz), 3.17(2H, q,J=7.7 Hz), 7.83(2H,s), 8.03(1H,d,J=8.8 Hz), 8.20(1H,dd, J=8.8,3.2 Hz), 8.55(1H,d,J=8.8 Hz).

EXAMPLE 88

Preparation of a compound of the structural formula:

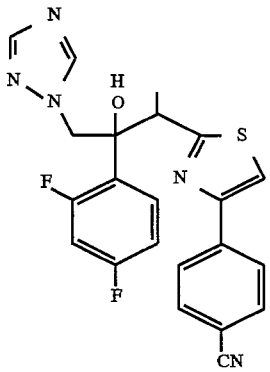

2-(2,4-Difluorophenyl)-3-thioamide-1-(1H-1,2,4-triazol-1-yl)-2-butanol (the raw material 2) (156 mg) was dissolved in EtOH (2 ml), and 2-bromo-4'-cyanoacetophenone (the raw material 3) (224 mg) was added to the solution, followed by heating and refluxing for 1 hour. The liquid reaction mixture was neutralized with a saturated aqueous solution of NaHCO$_3$ and subjected to extraction with AcOEt. After the extract was washed with H$_2$O and then a saturated aqueous solution of NaCl and dried over MgSO$_4$, AcOEt was distilled out. The resultant residue was purified by chromatography on silica gel (SiO$_2$: 20 g, eluted with CH$_2$Cl$_2$ and then with 1% solution of MeOH in CH$_2$Cl$_2$), and then crystallized from IPE, thereby obtaining the intended compound (109 mg). Physical properties of this compound are described below.

mp: 196°–197° C.

NMR: δ solvent (CDCl$_3$) 1.23(3H,d,J=8.0 Hz), 4.09(1H, q,J=8.0 Hz), 4.26(1H,d,J=14.3 Hz), 4.92(1H,d,J=14.3 Hz), 5.74(1H,s), 6.78–6.85(2H,m), 7.48–7.54(1H,m), 7.64(1H,s), 7.69(1H,s), 7.75(1H,d,J=8.1 Hz), 7.85(1H,s), 8.03(1H,d,J= 8.1 Hz).

MS: MH$^+$=438.

EXAMPLE 89

Preparation of a compound represented by the structural formula:

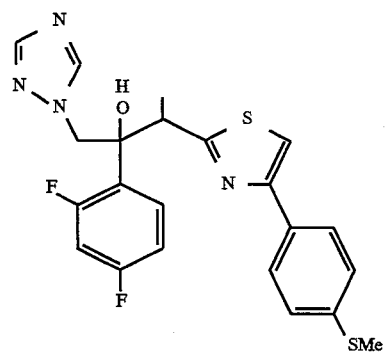

The intended compound was obtained in accordance with the same procedure as that described in Example 88 except that 2-bromo-4'-methylthioacetophenone was used in place of 2-bromo-4'-cyanoacetophenone. Physical properties of this compound are described below.

State: Solid.

NMR: δ solvent (CDCl$_3$) 1.23(3H,d,J=7.2 Hz), 2.54(3H, s), 4.05(1H,q,J=7.2 Hz), 4.28(1H,d,J=14.4 Hz), 4.88(1H,d, J=14.4 Hz), 6.13(1H,s), 6.75–6.85(2H,m), 7.33(2H,br-d,J= 8.4 Hz), 7.42(1H,s), 7.46–7.54(1H,m), 7.66(1H,s), 7.82(2H, br-d,J=8.4 Hz), 7.92(1H,s).

MS: MH$^+$=459.

EXAMPLE 90

[0081]

Preparation of a compound represented by the structural formula:

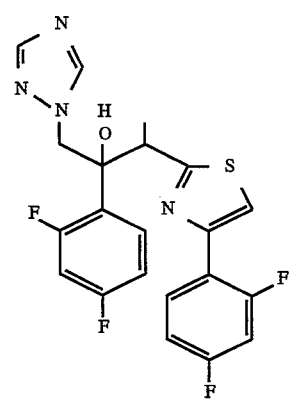

The intended compound was obtained in accordance with the same procedure as that described in Example 88 except that 2-bromo-2',4'-difluoroacetophenone was used in place of 2-bromo-4'-cyanoacetophenone. Physical properties of this compound are described below.

State: Solid.

NMR: δ solvent (CDCl₃) 1.23(3H,d,J=7.1 Hz), 4.07(1H, q,J=7.1 Hz), 4.26(1H,d,J=14.4 Hz), 4.89(1H,d,J=14.4 Hz), 5.93(1H,s), 6.92–6.98(1H,m), 7.00–7.05(1H,m), 7.47–7.54 (1H,m), 7.67(1H,s), 7.68(1H,s), 7.88(1H,s), 8.13–8.19(1H,m).

MS: MH⁺=449.

EXAMPLE 91

Preparation of a compound represented by the structural formula:

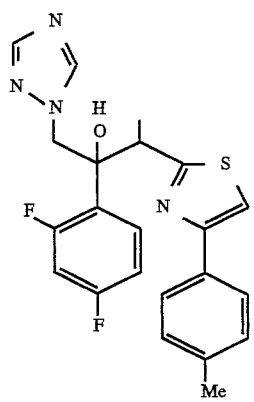

The intended compound was obtained in accordance with the same procedure as that described in Example 88 except that 2-bromo-4'-methylacetophenone was used in place of 2-bromo-4'-cyanoacetophenone. Physical properties of this compound are described below.

State: Solid.

NMR: δ solvent (CDCl₃) 1.23(3H,d,J=7.1 Hz), 2.41(3H, s), 4.04(1H,d,J=7.1 Hz), 4.28(1H,d,J=14.3 Hz), 4.88(1H,d, J=14.3 Hz), 6.24(1H,s), 6.76–6.84(1H,s), 7.27(2H,d,J=8.3 Hz), 7.40(1H,s), 7.47–7.53(1H,m), 7.65(1H,s), 7.80(2H,d, J=8.3 Hz), 7.94(1H,s).

MS: MH⁺=427.

EXAMPLE 92

Preparation of a compound represented by the structural formula:

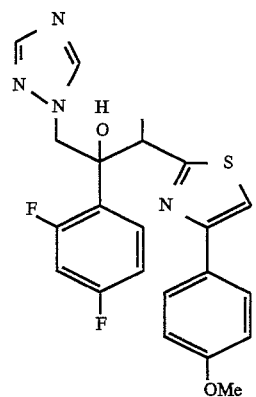

The intended compound was obtained in accordance with the same procedure as that described in Example 88 except that 2-bromo-4'-methoxyacetophenone was used in place of 2-bromo-4'-cyanoacetophenone. Physical properties of this compound are described below.

State: Solid.

NMR: δ solvent (CDCl₃) 1.23(3H,d,J=7.1 Hz), 3.88(3H, s), 4.04(1H,q,J=7.1 Hz), 4.28(1H,d,J=14.3 Hz), 4.87(1H,d, J=14.3 Hz), 6.24(1H,s), 6.76–6.84(2H,m), 7.00(2H,d,J=8.2 Hz), 7.32(1H,s), 7.47–7.53(1H,m), 7.65(1H,s), 7.84(2H,d, J=8.2 Hz), 7.94(1H,s).

MS: MH⁺=443.

EXAMPLE 93

Preparation of a compound represented by the structural formula:

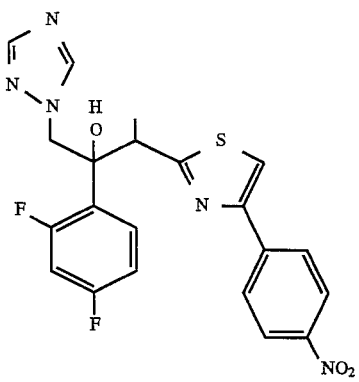

The intended compound was obtained in accordance with the same procedure as that described in Example 88 except that 2-bromo-4'-nitroacetophenone was used in place of 2-bromo-4'-cyanoacetophenone. Physical properties of this compound are described below.

mp: 180°–182° C.

NMR: δ solvent (CDCl₃) 1.25(3H,d,J=7.1 Hz), 4.11(1H, d,J=7.1 Hz), 4.27(1H,d,J=14.2 Hz), 4.94(1H,d,J=14.2 Hz), 5.70(1H,s), 6.79–6.85(2H,m), 7.43–7.55(1H,m), 7.70(1H,s), 7.71(1H,s), 7.85(1H,s), 8.08(2H,d,J=9.0 Hz), 8.32(2H,d,J= 9.0 Hz).

MS: MH⁺=458.

EXAMPLE 94

Preparation of a compound represented by the structural formula:

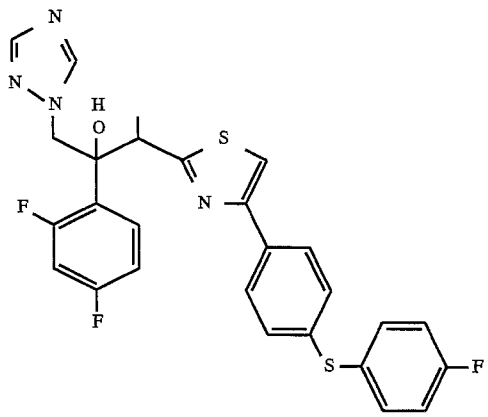

To a suspension of 1.570 g of 60% sodium hydride in 30 ml of DMD, were added 5 g of 4-fluorothiophenol, and the resultant mixture was stirred for 5 minutes at room temperature. To this mixture, 4.9 g of 4'-fluoroacetophenone were added, followed by stirring for 3.5 hours at 80° C. Water was added to the reaction mixture, followed by extraction with ethyl acetate. The extract was dashed with water and then saturated saline, and the solvent was distilled out under reduced pressure, thereby obtaining 10.008 g of 4-fluoro-4'-acetylphenyl sulfide.

After this, an intermediate compound represented by the structural formula:

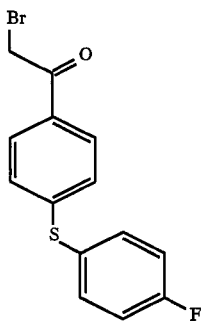

was prepared in accordance with the same procedure as that described in Preparation Example 4. The intended compound was then obtained in accordance with the same procedure as that described in Example 88 except that this compound was used in place of 2-bromo-4'-cyanoacetophenone. Physical properties of this compound are described below.

State: Solid.

NMR: δ solvent (CDCl$_3$) 1.22(3H,d,J=7.0 Hz), 4.05(1H, q,J=7.0 Hz), 4.26(1H,d,J=14.6 Hz), 4.88(1H,d,J=14.6 Hz), 6.04(1H,s), 6.76–6.85(2H,m), 7.07(2H,br-dd,J=8.4,8.4 Hz), 7.32(2H,br-d,J=8.4 Hz), 7.44(1H,br-s), 7.44(2H,br-dd,J= 8.4,8.4 Hz), 7.45–7.54(1H,m), 7.66(1H,s), 7.82(2H,br-d,J= 8.4 Hz), 7.89(1H,s).

MS: MH$^+$=539.

EXAMPLE 95

Preparation of a compound represented by the structural formula:

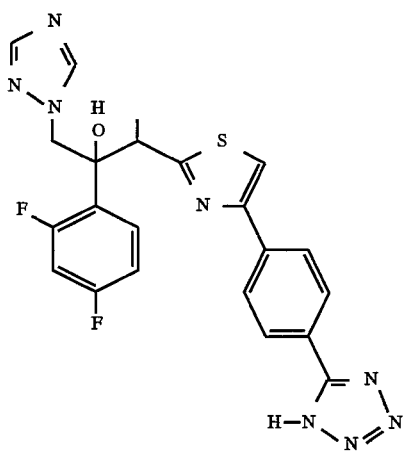

In 4 ml of N-methylpyrrolidone, were dissolved 400 mg of the compound obtained in Example 88, and 123 mg of NaN$_3$ and 260 mg of Et$_3$N·HCl were added to the solution. The resultant mixture was heated for 6.5 hours at an external temperature of 100° C. on an oil bath, and 31 mg of NaN$_3$ and 65 mg of Et$_3$N·HCl were further added to conduct a reaction for 20 hours at 90° C. To the reaction mixture, CH$_2$Cl$_2$ was added, and a salt formed was removed by filtration, followed by evaporation of the liquid reaction mixture. To the residue, were added EtOH, acetone, H$_2$O and 1N HCl, and the resultant mixture was left to stand, thereby depositing solid matter. This solid matter was recovered by filtration, thereby obtaining 390 mg of the intended compound. Physical properties of this compound are described below.

mp: 166°–169° C.

NMR: δ solvent (DMSO-d$^6$) 1.14(3H,d,J=7.3 Hz), 4.11 (1H,q,J=7.3 Hz), 4.37(1H,d,J=14.6 Hz), 4.87(1H,d,J=14.6 Hz), 6.08(1H,s), 6.91–6.96(1H,m), 7.18–7.25(1H,m), 7.27–7.34(1H,m), 7.62(1H,s), 8.11(2H,d,J=8.5 Hz), 8.20 (2H,d,J=8.5 Hz), 8.22(1H,s), 8.29(1H,s).

MS: MH$^+$=481.

EXAMPLE 96

Preparation of a compound represented by the structural formula:

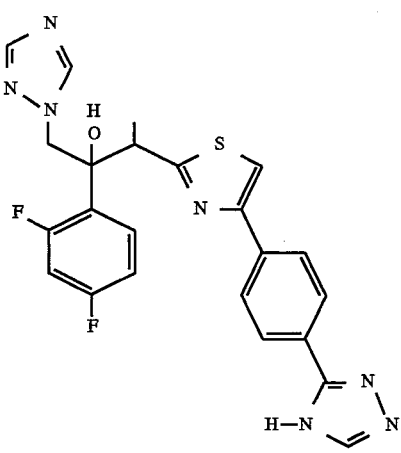

In H$_2$O (4 ml), were suspended 800 mg of the compound obtained in Example 88, and 2.6 ml (16.479 mmol) of a compound represented by the formula:

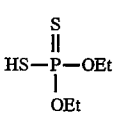

were added to the suspension, followed by heating and refluxing for 30 minutes. To the liquid reaction mixture, H$_2$O was added, and the mixture was subjected to extraction with AcOEt. After the extract was washed with H$_2$O and then a saturated aqueous solution of NaCl and dried over MgSO$_4$, AcOEt was distilled out. The resultant residue was dissolved in 10 ml of acetone without purifying it, and 0.45 ml of CH$_3$I was added to the solution, followed by stirring for 40 minutes at 40° C. To the resulting liquid reaction mixture, H$_2$O was added, and the mixture was subjected to extraction with AcOEt. After the extract was washed with H$_2$O and then a saturated aqueous solution of NaCl and dried over MgSO$_4$, AcOEt was distilled out. The resultant residue was dissolved in 10 ml of EtOH without purifying it, and 220 mg of NH$_2$NHCHO, 0.26 ml of Et$_3$N and one drop of H$_2$SO$_4$ were added to the solution, followed by heating and refluxing for 1 hour. The resulting liquid reaction mixture was added with H₂O and subjected to extraction with AcOEt. After the resultant extract was washed with H₂O and then a saturated aqueous solution of NaCl and dried over MgSO₄, AcOEt was distilled out. The resultant residue was purified by column chromatography (SiO₂: 50 g, eluted with CH₂Cl₂, and then with 1% solution of MeOH in CH₂Cl₂ and with 2% solution of MeOH in CH₂Cl₂), thereby obtaining 369 mg of the intended compound. Physical properties of this compound are described below.

State: Solid.

NMR: δ solvent (CDCl₃) 1.24(3H,d,J=7.1 Hz), 4.08(1H, q,J=7.1 Hz), 4.34(1H,d,J=14.4 Hz), 4.91(1H,d,J=14.4 Hz), 6.15(1H,s), 6.79–6.85(1H.s), 7.52–7.56(2H,m), 7.69(1H,s), 7.97–7.99(3H,m), 8.14(2H,d,J=8.2 Hz), 8.25(1H,s).

MS: MH⁺=480.

EXAMPLE 97

Preparation of a compound represented by the structural formula:

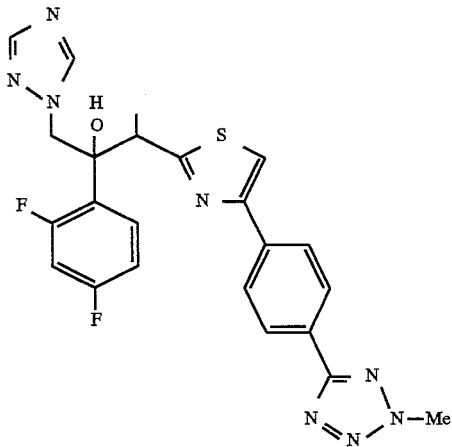

In 3 ml of DMF, were dissolved 250 mg of the compound obtained in Example 95, and 174 mg of CsCO₃ were added to the solution. The resulting mixture was heated for 30 minutes at an external temperature of 60° C. on an oil bath and added with 0.05 ml of CH₃I, followed by stirring for 30 minutes at room temperature. The liquid reaction mixture was added with H₂O and subjected to extraction with AcOEt. After the extract was washed with water and then a saturated aqueous solution of NaCl and dried over MgSO₄, AcOEt was distilled out. The resultant residue was purified by column chromatography (SiO₂: 30 g, eluted with CH₂Cl₂, and then with 1% solution of MeOH in CH₂Cl₂ and with 2% solution of MeOH in CH₂Cl₂), thereby obtaining 125 mg of the intended compound. Physical properties of this compound are described below.

mp: 191°–193° C.

NMR: δ solvent (CDCl₃) 1.25(3H,d,J=7.0 Hz), 4.09(1H, q,J=7.0 Hz), 4.29(1H,d,J=14 Hz), 4.33(3H,s), 4.92(1H,d,J= 14 Hz), 6.01(1H,s), 6.77–6.85(2H,m), 7.49–7.55(1H,m), 7.58(1H,s), 7.67(1H,s), 7.91(1H,s), 8.04(2H,d,J=8.2 Hz), 8.24(2H,d,J=8.2 Hz).

MS: MH⁺=495.

EXAMPLE 98

Preparation of a compound represented by the structural formula:

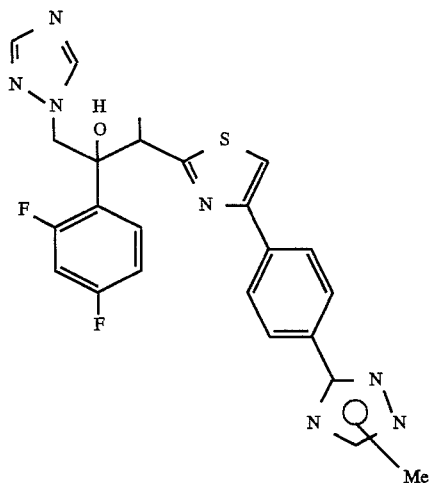

In 5 ml of acetone, were dissolved 200 mg of the compound obtained in Example 96, and 60.6 mg of K₂CO₃ and 0.03 ml of CH₃I were added to the solution. The resulting mixture was stirred for 19 hours at room temperature. The liquid reaction mixture was added with H₂O and subjected to extraction with AcOEt. After the extract was washed with H₂O and then a saturated solution of NaCl and dried over MgSO₄, AcOEt was distilled out. The resultant residue was purified by column chromatography (SiO₂: 40 g, eluted with CH₂Cl₂, and then with 0.5% solution of MeOH in CH₂Cl₂ and with 1% solution of MeOH in CH₂Cl₂), thereby obtaining 142 mg of the intended compound. Physical properties of this product are described below.

State: Solid.

NMR: δ solvent (CDCl₃) 1.13(1H,d,J=6.0 Hz), 1.25(2H, d,J=7.1 Hz), 4.01–4.13(4H,m), 4.27(2/3H,d,J=14 Hz), 4.29 (1/3H,d,J=14 Hz), 4.91(1H,d,J=14 Hz), 5.45(1/3H,s), 6.08 (2/3H,s), 6.70–6.84(2H,m), 7.50–7.55(2H,m), 7.67–7.68(4/ 3H,m), 7.79–7.81(2/3H,m), 7.93(1H,s), 7.96(1H,s), 7.98 (1H,s), 8.10(1H,s), 8.19(2H,d,H=8.4 Hz).

EXAMPLE 99

Preparation of a compound represented by the structural formula:

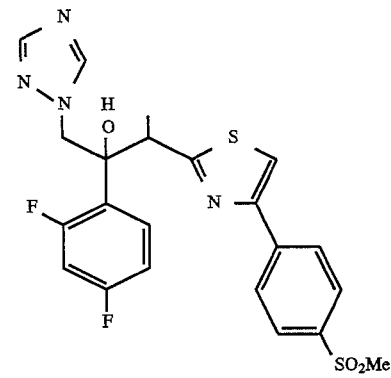

To a solution with 138 mg of the compound obtained in Example 89 dissolved in 3 ml of chloroform, were added 215 mg of meta-chloroperbenzoic acid, followed by stirring at room temperature. After the raw material disappeared, water was added to the liquid reaction mixture, followed by extraction with ethyl acetate. The resultant organic layer was washed with a 50% saturated aqueous solution of sodium hydrogencarbonate, water and saturated saline. After the solvent was distilled out under reduced pressure, the residue was purified by column chromatography on silica gel and crystallized from dichloromethane-diisopropyl ether, thereby obtaining 98.5 mg of the intended compound. Physical properties of this product are described below.

State: Solid.

NMR: δ solvent (CDCl$_3$) 1.24(3H,d,J=7.2 Hz), 3.09(3H, s), 4.09(1H,q,J=7.2 Hz), 4.27(1H,d,J=14.4 Hz), 4.91(1H,d, J=14.4 Hz), 5.78(1H,s), 6.78–6.85(2H,m), 7.47–7.55(1H, m), 7.67(1H,s), 7.69(1H,s), 7.87(1H,s), 8.02(2H,br-d,J=8.4 Hz), 8.10(2H,br-d,J=8.4 Hz).

MS: MH$^+$=491.

EXAMPLE 100

Preparation of a derivative represented by the structural formula:

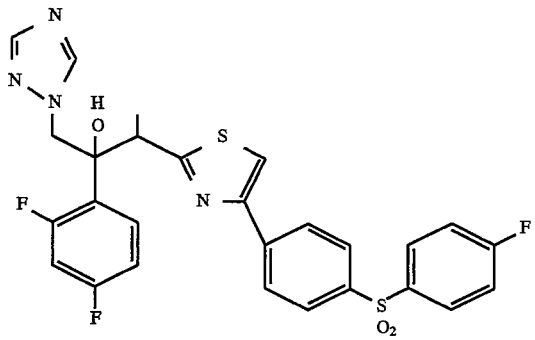

The intended compound was obtained from the compound obtained in Example 7 in accordance with the same procedure as in Example 99. Physical properties of this product are described below.

mp: Solid.

NMR: δ solvent (CDCl$_3$) 1.22(3H,d,J=7.2 Hz), 4.07(1H, q,J=7.2 Hz), 4.23(1H,d,J=14.4 Hz), 4.90(1H,d,J=14.4 Hz), 5.73(1H,s), 6.77–6.84(2H,m), 7.20(2H,br-dd,J=8.4,8.4 Hz), 7.46–7.53(1H,m), 7.63(1H,s), 7.68(1H,s), 7.83(1H,s), 7.97–8.07(6H,m).

MS: MH$^+$=571.

EXAMPLE 101

Preparation of derivatives represented by the structural formulae:

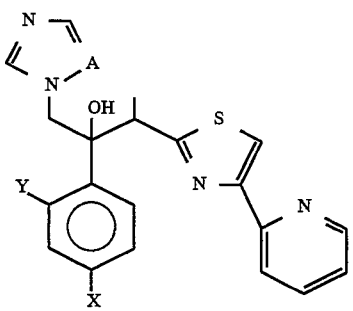

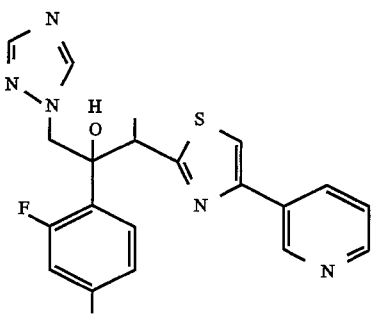

and

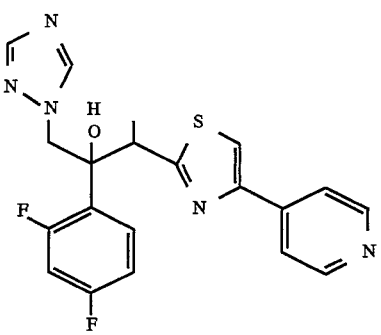

Compounds I, II and III according to this example were obtained in accordance with the same procedure as in Example 88 except that the 4-cyanophenyl moiety in the raw material 3 was changed to their corresponding pyridyl groups which were different in bonding position from each other. Physical properties of these compounds are described below.

(I)

mp: 149°–151° C.

NMR: δ solvent (DMSO-d$^6$) 1.13(3H,d,J=7.1 Hz), 4.07 (1H,q,J=7.1 Hz ), 4.36(1H,d,J=14.3 Hz), 4.86(1H,d,J=14.3 Hz), 6.07(1H,s), 6.91–6.96(1H,m), 7.18–7.24(1H,m), 7.27–7.36(2H,m), 7.61(1H,s), 7.88(1H,t,J=8 Hz), 8.11(1H, d,J=8 Hz), 8.22(1H,s), 8.28(1H,s), 8.60–8.62(1H,m).

MS: MH$^+$=414.

(II)

mp: 148°–149° C.

NMR: δ solvent (CDCl$_3$) 1.24(3H,d,J=7.1 Hz), 4.09(1H, q,J=7.1 Hz), 4.27(1H,d,J=14.3 Hz), 4.92(1H,d,J=14.3 Hz), 5.84(1H,brs), 6.77–6.85(2H,m), 7.40(1H,ddd,J=7.8,4.8,0.92 Hz), 7.48–7.56(1H,m), 7.58(1H,s), 7.68(1H,s), 7.88(1H,s), 8.21(1H,ddd,J=7.8,2.2,1.6 Hz), 8.61(1H,dd,J=4.8,1.6 Hz), 9.15(1H,dd,J=2.2,0.92 Hz).

MS: MH⁺=414.

(III)

State: Solid.

NMR: δ solvent (CDCl₃) 1.24(3Hx4/5,d,J=7.1 Hz), 1.68 (3Hx1/5,d,J=6.2 Hz), 4.08–4.15(1H,m), 4.25(4/5H,q,J=14.5 Hz), 4.73(1/5H,d,J=13.9 Hz), 4.92(1/5H,d,J=13.9 Hz), 4.95 (4/5H,d,J=14.5 Hz), 5.77(4/5H,brs), 5.88(1/5H,brs), 6.49–6.55(1/5H,m), 6.66–6.72(1/5H,m), 6.76–6.85(1H,m), 7.07–7.14(4/5H,m), 7.26(1/5H,s), 7.44(1/5H,s), 7.47–7.55 (4/5H,m), 7.61–7.64(1/5H,m), 7.69(4/5H,s), 7.73(4/5H,s), 7.78–7.81(4/5H,m), 7.87(4/5H,s), 8.03(1/5H,s), 8.64–8.66 (4/5H,m), 8.69–8.72(1/5H,m).

MS: MH⁺=414.

EXAMPLE 102

Preparation of a compound represented by the structural formula:

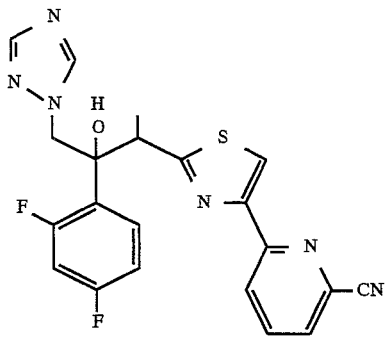

In 7 ml of AcOEt and 5 ml of THF, were dissolved 700 mg of the compound (I) obtained in Example 101, and 500 mg of mCPBA were added to the solution, followed by stirring for 1 hour at room temperature and then further addition of 227 mg (0.882 mmol) of mCPBA. The resultant mixture was stirred for 1 hour. The liquid reaction mixture was added with an aqueous solution of sodium sulfite, stirred for 5 minutes and subjected to extraction with AcOEt. After the extract was washed with an aqueous solution of sodium sulfite, an aqueous solution of NaHCO₃, H₂O and then an aqueous solution of NaCl and dried over MgSO₄, the solvent was distilled out. The residue was crystallized from CH₂Cl₂-IPE, thereby obtaining 510 mg of an N-oxide intermediate. The compound was dissolved in 5 ml of CH₂Cl₂, and 0.49 ml of TMS-CN was added to the solution at room temperature. After 5 minutes, 0.34 ml of Me₂NCOCl was added, and the mixture was heated and refluxed for 1.5 hours. Further, 0.25 ml of TMS-CN and 0.17 ml of Me₂NCOCl were added, and the resultant mixture was heated and refluxed for 2.5 hours. An aqueous solution of NaHCO₃ was added to the liquid reaction mixture, and the mixture was subjected to extraction with AcOEt. After the extract was washed with H₂O and a saturated aqueous solution of NaCl and dried over MgSO₄, the solvent was distilled out. The resulting residue was purified by chromatography on silica (SiO₂: 40 g, eluted with CH₂Cl₂, and then with 1% solution of MeOH in CH₂Cl₂ and with 2% solution of MeOH in CH₂Cl₂), thereby obtaining 198 mg of the intended compound. Physical properties of this compound are described below.

mp: 197°–200° C.

NMR: δ solvent (DMSO-d⁶) 1.14(3H,d,J=7.0 Hz), 4.07–4.11(1H,m), 4.47(1H,q,J=14.3 Hz), 4.84(1H,d,J=14.3 Hz), 6.10(1H,s), 6.91–6.96(1H,m), 7.18–7.22(1H,m), 7.23–7.33(2H,m), 7.61(1H,s), 7.98(1H,d,J=7.7 Hz), 8.14 (1H,t,J=7.7 Hz), 8.21(1H,s), 8.40(1H,d,J=7.7 Hz), 8.44(1H, s).

MS: MH⁺=439.

EXAMPLE 103

Preparation of a compound (I) represented by the structural formula:

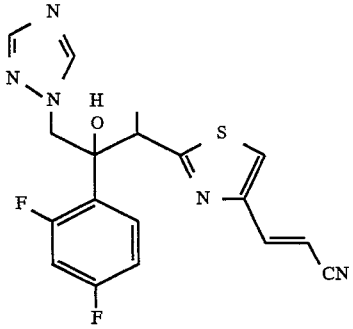

and another compound (II) represented by the structural formula:

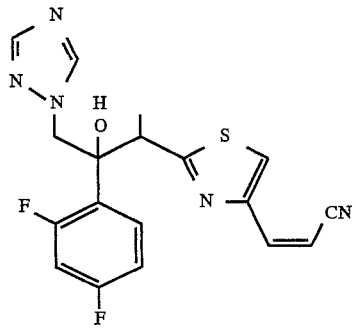

In 16 ml of EtOH, were dissolved 1.6 g of 2-(2,4-difluorophenyl)-3-thioamide-1-(1H-1,2,4-triazol-1-yl) butan-2-ol (156 mg), and 0.71 ml of ethyl bromopyruvate was added to the solution. The resultant mixture was heated and refluxed for 5 hours. The liquid reaction mixture was cooled back to room temperature, neutralized with a saturated aqueous solution of NaHCO₃, and subjected to extraction with AcOEt. After the extract was washed with H₂O and then a saturated aqueous solution of NaCl and dried over MgSO₄, the solvent was distilled out. The residue was purified by chromatography (SiO₂: 150 g, eluted with CH₂Cl₂ and then with 1% solution of MeOH in CH₂Cl₂ and with 2% solution of MeOH in CH₂Cl₂), thereby obtaining 435 mg of 2-(2,4-difluorophenyl)-3-(4-ethoxycarbonylthiazol-2-yl)-1-(1H-1,2,4-triazol-1-yl)butan-2-ol. In 20 ml of THF, were dissolved 1.9 g of this compound, and 5.1 ml of a 1M toluene solution of DIBAL were added slowly to the solution at −78° C. After 40 minutes, 2.3 ml of the 1M toluene solution of DIBAL were further added at the same temperature. After 1 hour, an aqueous solution of NH₄Cl was added to the liquid reaction mixture at −78° C. The reaction mixture was heated back to room temperature, added with H₂O and subjected to extraction with AcOEt. After the extract was washed with H₂O and dried over MgSO₄, the solvent was distilled out, thereby obtaining 989 mg of 2-(2,4-difluorophenyl)-3-(4-formylthiazol-2-yl)-1-(1H-1,2,4-triazol-1-yl)butan-2-ol as a crude product.

To 5 ml of THF, 60% NaH (109 mg) was added while chilling with ice water, and a solution with (Et₂O)₂P(=O) CH₂CN (0.44 ml) dissolved in 5 ml of THF was added dropwise to the mixture. After stirring the mixture for 1 hour, a solution with 989 mg of the above-obtained product dissolved in 10 ml of THF was added slowly to the mixture. After stirring the resulting mixture for 30 minutes at room temperature, H₂O was added to the liquid reaction mixture, followed by extraction with AcOEt. After the extract was washed with H₂O and then a saturated aqueous solution of NaCl and dried over MgSO₄, AcOEt was distilled out. The resultant residue was purified by chromatography on silica gel (SiO₂: 60 g, eluted with CHCl₃, and then with 1% solution of MeOH in CHCl₃ and with 2% solution of MeOH in CHCl₃), thereby obtaining 115 mg of the compound I as the first eluate, and 220 mg of the compound II of geometrical isomer as the second eluate. Physical properties of these compounds are described below.

I

State: Solid.

mp: 175°–177° C.

NMR: δ solvent (CDCl₃) 1.19(3H,d,J=7.1 Hz), 4.02(1H, q,J=7.1 Hz ), 4.16(1H,d,J=14.3 Hz), 4.91(1H,d,J=14.3 Hz), 5.47(1H,s), 6.33(1H,d,J=16.0 Hz), 6.77–6.84(2H,m), 7.33 (1H,d,J=16.0 Hz), 7.46(1H,s), 7.47–7.51(1H,m), 7.72(1H, s), 7.82(1H,s).

MS: MH⁺=388.

II

State: Solid.

NMR: δ solvent (CDCl₃) 1.20(3H,d,J=7.0 Hz), 4.05(1H, q,J=7.0 Hz), 4.45(1H,d,J=14.0 Hz), 4.89(1H,d,J=14.0 Hz), 5.56(1H,d,J=11.9 Hz), 5.78(1H,s), 6.75–6.82(2H,m), 7.17 (1H,d,J=11.9 Hz), 7.50–7.59(1H,m), 7.60(1H,s), 7.75(1H,s), 8.10(1H,s).

MS: MH⁺=388.

EXAMPLE 104

Preparation of a compound represented by the structural formula:

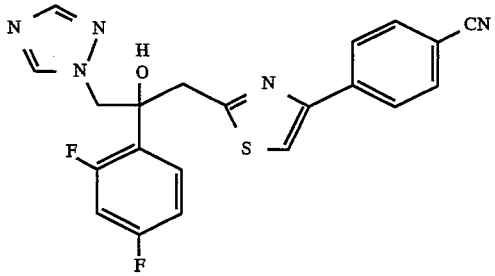

The intended compound was obtained in accordance with the same procedure as in Example 88 except that 2-(2,4-difluorophenyl)-3-thioamide-1-(1H-1,2,4-triazol-1-yl) propan-2-ol was used in place of 2-(2,4-difluorophenyl)-3-thioamide-1-(1H-1,2,4-triazol-1-yl)butan-2-ol. Physical properties of this compound are described below.

mp: 148°–149° C.

NMR: δ solvent (CDCl₃) 3.38(1H,d,J=15.2 Hz), 3.87(1H, d,J=15.2 Hz), 4.65(1H,d,J=14.0 Hz), 4.71(1H,d,J=14.0 Hz), 5.97(1H,s), 6.70–6.76(1H,m), 6.77–6.83(1H,m), 7.42(1H, m), 7.47–7.41(1H,m), 7.69–7.72(2H,m), 7.86(1H,s), 7.86–7.90(2H,m), 8.18(1H,s).

MS: MH⁺=424.

EXAMPLE 105

Preparation of a compound represented by the structural formula:

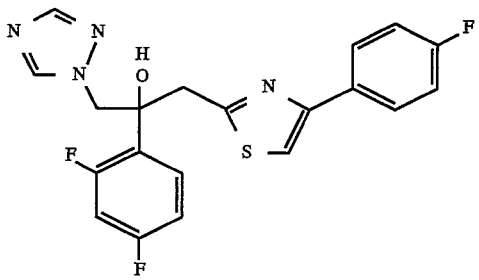

The intended compound was obtained in accordance with the same procedure as that described in Example 104 except that 2-bromo-4'-fluoroacetophenone was used in place of 2-bromo-4'-cyanoacetophenone. Physical properties of this compound are described below.

State: Solid.

NMR: δ solvent (CDCl₃) 3.34(1H,d,J=15.4 Hz), 3.84(1H, d,J=15.4 Hz), 4.62(1H,d,J=14.0 Hz), 4.71(1H,d,J=14.0 Hz), 6.25(1H,s), 6.82–6.69(2H,m), 7.13–7.08(2H,m), 7.17(1H,s), 7.47–7.40(1H,m), 7.76–7.72(2H,m), 7.85(1H,s), 8.21(1H,s).

MS: MH⁺=417.

EXAMPLE 106

Preparation of a compound I represented by the structural formula:

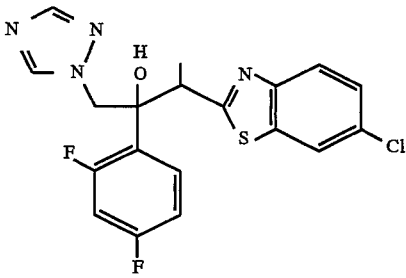

and another compound II which is a diastereomer of the compound I:

After normal-butyllithium (1.6M hexane solution; 313 ml) was added dropwise to diisopropylamine (840 μl ) in 15 ml of tetrahydrofuran at –65° C., the mixture was increased to 4° C., thereby conducting a reaction for 15 minutes to prepare a lithium diisopropylamide solution. After chilling the solution to –63° C., a tetrahydrofuran solution (10 ml) of 2-ethyl-6-chloro-benzothiazole (988 mg) prepared in Preparation Example 5, and a tetrahydrofuran solution (12 ml) of 1-(1H-1,2,4-triazol-1-yl)-2',4'-difluoroacetophenone (1.227 g) were successively added to the amide solution at an internal temperature not higher than –60° C. After conducting a reaction for 15 minutes, the reaction mixture was heated to 0° C. and added with an aqueous solution of ammonium chloride. The resultant mixture was subjected to extraction with ethyl acetate. The resulting organic layer was washed with water and then saline, dried and evaporated to dryness under reduced pressure. The residue was purified through a silica gel column (dichloromethane:methanol= 100:1). The thus-obtained diastereomer mixture was further caused to pass through the silica gel column (dichloromethane:ethyl acetate=10:1→5:1), thereby obtaining 442 mg of the compound I as a low-polar fraction, and 66 mg of the compound II, which is a diastereomer thereof, as a high-polar fraction. Physical properties of these compounds are described below.

I mp: 187° C.

NMR: δ solvent (CDCl₃) 1.25(3H,d,J=7.0 Hz), 4.09(1H, q,J=7.0 Hz), 4.27(1H,d,J=14.4 Hz), 4.93(1H,d,J=14.4 Hz), 5.80(1H,s), 6.85–6.78(2H,m), 7.48(1H,dd,J=8.8 Hz,2.4 Hz), 7.49–7.55(1H,m), 7.67(1H,s), 7.87(1H,s), 7.90(1H,d,J=2.4 Hz), 7.94(1H,d,J=8.8 Hz).

MS: MH⁺=421.

II mp: 127°–130° C.

NMR: δ solvent (CDCl₃) 1.68(3H,d,J=6.8 Hz), 4.13(1H, q,J=6.8 Hz), 4.71(1H,d,J=14 Hz), 4.94(1H,d,J=14 Hz), 5.87(1H,s), 6.46–6.50(1H,m), 6.43–6.69(1H,m), 7.09–7.16(1H, m), 7.38(1H,dd,J=2.0 Hz,8.8 Hz), 7.69(1H,s), 7.72(1H,d,J= 2.0 Hz), 7.80(1H,d,J=8.8 Hz), 8.04(1H,s).

MS: MH⁺=421.

EXAMPLE 107

Preparation of a compound represented by the structural formula:

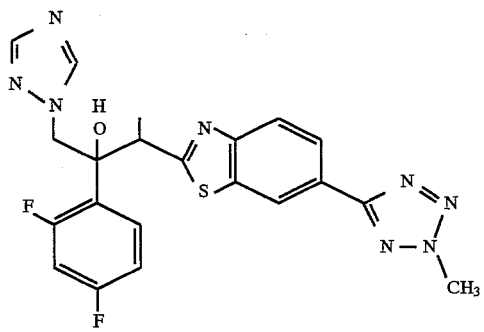

A mixture of 2-ethyl-6-cyanobenzothiazole (1.78 g), sodium azide (1.22 g) and triethylamine hydrochloride (2.59 g) was heated at 100° C. for 3 hours in 300 ml of N-methylpyrrolidone. After cooling the mixture to room temperature, it was added with 150 ml of water, adjusted to pH 3 with concentrated hydrochloric acid and subjected twice to extraction with ethyl acetate. The resultant organic layer was washed with saturated saline and dried. The solvent was distilled out and the remaining solvent was further removed by azeotropic distillation with toluene, thereby obtaining 2-ethyl-6-(tetrazol-5-yl)benzothiazole (1.86 g). This compound was dissolved in dimethylformamide (20 ml), and cesium carbonate (3.06 g) was added to the solution, followed by heating at 80° C. for 1.5 hours. Then, 1.17 ml of iodomethane were added to the reaction mixture while chilling with ice. The mixture was allowed to back to room temperature and stirred for 7 hours. Water and ethyl acetate were added to separate the mixture into liquids, and the resultant organic layer was washed with water and dried. The residue was purified through a silica gel column (hexane:ethyl acetate=4:1), thereby obtaining 2-ethyl-6-(2-methyl-tetrazol-5-yl)benzothiazole (930 mg). Using the compound thus produced, the intended compound was obtained in the same manner as in Example 106. Physical properties of this compound are described below.

mp: 182°–185° C.

NMR: δ solvent (CDCl₃) 1.28(3H,d,J=7.2 Hz), 4.13(1H, q,J=7.2 Hz), 4.31(1H,d,J=14.2 Hz), 4.44(3H,s), 4.96(1H,d, J=14.2 Hz), 5.89(1H,s), 6.78–6.86(2H,m), 7.50–7.58(1H, m), 7.67(1H,s), 7.89(1H,s), 8.13(1H,dd,J=0.4 Hz,8.8 Hz), 8.30(1H,dd,J=1.6 Hz,8.8 Hz), 8.74(1H,dd,J=0.4 Hz,1.6 Hz).

EXAMPLE 108

Preparation of a compound represented by the structural formula:

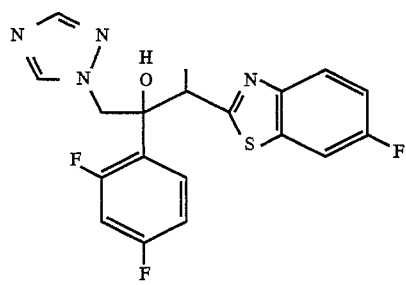

The intended compound was prepared in the same manner as in Example 106 except that 2-ethyl-6-fluoro-benzothiazole was used in place of 2-ethyl-6-chloro-benzothiazole. Physical properties of this compound are described below.

mp: 151°–153° C.

NMR: δ solvent (CDCl₃) 1.25(3H,d,J=7.1 Hz), 4.08(1H, q,J=7.1 Hz), 4.28(1H,d,J=14.4 Hz), 4.93(1H,d,J=14.4 Hz), 5.83(1H,s), 6.77–6.85(2H,m), 7.23–7.29(1H,m), 7.49–7.56 (1H,m), 7.58–7.62(1H,m), 7.67(1H,s), 7.87(1H,s), 7.96–8.00(1H,m).

MS: MH⁺=405.

EXAMPLE 109

Preparation of a compound represented by the structural formula:

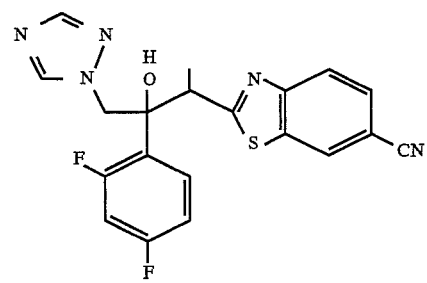

The intended compound was prepared in the same manner as in Example 106 except that 2-ethyl-6-cyano-benzothiazole was used in place of 2-ethyl-6-chloro-benzothiazole. Physical properties of this compound are described below.

mp: 186°–188° C.

NMR: δ solvent (CDCl₃) 1.27(3H,d,J=7.2 Hz), 4.16(1H, q,J=7.2 Hz), 4.24(1H,d,J=14.0 Hz), 4.96(1H,d,J=14.0 Hz), 5.67(1H,s), 6.79–6.86(2H,m), 7.49–7.56(1H,m), 7.69(1H,s), 7.77(1H,dd,J=1.6 Hz,8.4 Hz), 7.83(1H,s), 8.11(1H,d,J=8.4 Hz), 8.27(1H,d,J=1.6 Hz).

MS: MH⁺=412.

EXAMPLE 110

Preparation of a compound represented by the structural formula:

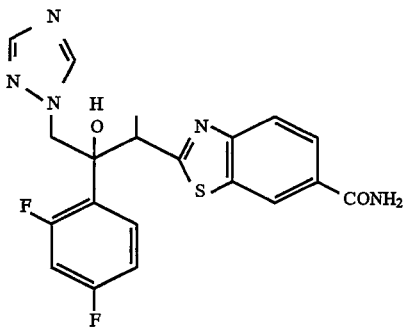

The compound (506 mg) obtained in Example 109 was suspended in methanol (10 ml), and 0.37 ml of a 1N aqueous solution of sodium hydroxide and 30% aqueous hydrogen peroxide (0.42 ml) were successively added to the suspension. The resultant mixture was stirred for 2 hours at room temperature, and water and ethyl acetate were added to conduct extraction. The resulting organic layer was washed with water, dried, followed by subjecting to distillation. The residue was purified through a silica gel column (dichloromethane:methanol=50:1→20:1), thereby obtaining the intended compound (311 mg). Physical properties of this compound are described below.

mp: 112°–117° C.

NMR: δ solvent (CDCl$_3$) 1.25(3H,d,J=7.0 Hz), 4.13(1H, q,J=7.0 Hz), 4.29(1H,d,J=14.4 Hz), 4.94(1H,d,J=14.4 Hz), 5.82(1H,s), 5.60–6.25(2H,br), 6.78–6.86(2H,m), 7.50–7.56 (1H,m), 7.67(1H,s), 7.87(1H,s), 7.90(1H,dd,J=1.6 Hz,8.4 Hz), 8.08(1H,dd,J=1.6 Hz,8.4 Hz), 8.48(1H,dd,J=0.6 Hz,1.6 Hz).

MS: MH$^+$=430.

EXAMPLE 111

Preparation of a compound represented by the structural formula:

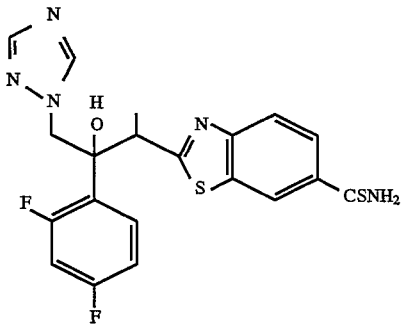

The compound (507 mg) obtained in Example 109 and one drop of triethylamine were dissolved in dimethylformamide (5 ml), and the solution was saturated with hydrogen sulfide gas at room temperature and left over for 6 hours at room temperature. The liquid reaction mixture was added with an aqueous solution of sodium hydrogencarbonate and ethyl acetate to separate into liquids. The resultant organic layer was washed with water, dried and then concentrated. The residue was purified through a silica gel column (eluting solvent: dichloromethane:methanol=50:1), thereby obtaining the intended compound (538 mg). Physical properties of this compound are described below.

mp: 157°–160° C.

NMR: δ solvent (CDCl$_3$) 1.23(3H,d,J=7.2 Hz), 4.13(1H, q,J=7.2 Hz), 4.27(1H,d,J=14.0 Hz), 4.94(1H,d,J=14.0 Hz), 5.81(1H,s), 6.78–6.85(2H,m), 7.24–7.30(1H,br-s), 7.39–7.56(1H,m), 7.67(1H,s), 7.66–7.72(1H,brs), 7.86(1H, s), 7.95(1H,dd,J=2.0 Hz,8.8 Hz), 8.02(1H,d,J=8.8 Hz), 8.59 (1H,d,J=2.0 Hz).

MS: MH$^+$=446.

EXAMPLE 112

Preparation of a compound (1:1 diastereomer mixture) represented by the structural formula:

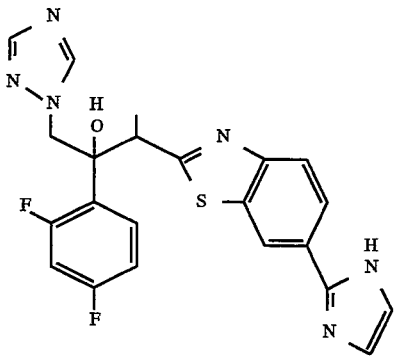

The compound (2.67 g) obtained in Example 111 was suspended in 130 ml of acetone, and 1.12 ml of iodomethane were added to the suspension to heat and reflux the resultant mixture at 40° C. for 8 hours. The solvent was distilled out to obtain an intermediate compound represented by the structural formula:

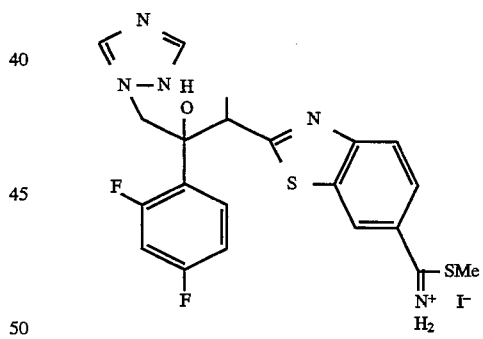

This intermediate compound (584 mg) was dissolved in ethanol (5.8 ml), and aminodiethyl acetal (174 μl) was added to the solution to heat and reflux the resultant mixture for 5 hours. Then, 6N hydrochloric acid (5 ml) was added to the mixture, followed by heating and refluxing for 1 hour. Aqueous sodium hydrogencarbonate and ethyl acetate were added to the liquid reaction mixture to separate the mixture into liquids. The resultant organic layer was washed with water, dried and evaporated to dryness. The residue was purified through a silica gel column (dichloromethane:methanol=100:1 - 10:1), thereby obtaining the intended compound as a 1:1 diastereomer mixture.

State: Solid.

NMR: δ solvent (CDCl$_3$) 1.27(3H,d,J=7.2 Hz), 1.73(3H, d,J=7.2 Hz), 4.10(1H,q,J=7.2 Hz), 4.15(1H,q,J=7.2 Hz), 4.32(1H,d,J=14.0 Hz), 4.73(1H,d,J=14.0H), 4.94(1H,d,J=

14.0 Hz), 4.95(1H,d,J=14.0 Hz), 5.92(1H,s), 5.98(1H,s), 6.44–6.50(1H,m), 6.63–6.70(1H,m), 6.77–6.84(2H,m), 7.12–7.17(1H,m), 7.17(1H,br-s), 7.22(1H,br-s), 7.50–7.57 (1H,m), 7.66(1H,s), 7.69(1H,s), 7.84(1H,dd,J=1.6 Hz,8.4 Hz), 7.89(1H,s), 7.91(1H,d,J=8.4 Hz), 7.93(H,dd,J=1.6 Hz,8.4 Hz), 8.05(1H,d,J=8.4 Hz), 8.06(1H,s), 8.27(1H,d,J= 1.6 Hz), 8.46(1H,d,J=1.6 Hz).

EXAMPLE 113

Preparation of a compound represented by the structural formula:

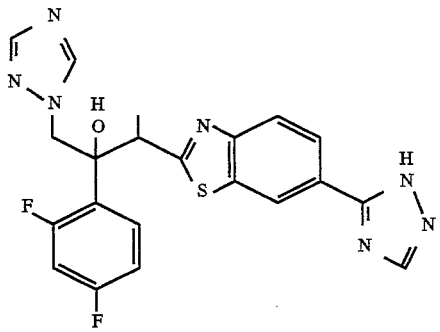

The intermediate compound (1.17 g) in Example 112 was dissolved in ethanol (12 ml), and formylhydrazine (240 mg), triethylamine (250 µl) and one drop of concentrated sulfuric acid were successively added to the solution, thereby conducting a reaction for 40 minutes at room temperature and then for 1.5 hours while heating and refluxing the reaction mixture. After cooling the reaction mixture, ethyl acetate and water were added to conduct extraction. The resultant organic layer was washed with water, dried and concentrated. The residue was purified by a column chromatography on silica gel (dichloromethane:methanol=20:1), thereby obtaining the intended compound (742 mg). Physical properties of this compound are described below.

mp: 138°–140° C.

NMR: δ solvent (CDCl₃) 1.27(3H,d,J=7.2 Hz), 4.13(1H, q,J=7.2 Hz), 4.33(1H,d,J=14.2 Hz), 4.95(1H,d,J=14.2 Hz), 5.96(1H,s), 6.78–6.86(2H,m), 7.51–7.57(1H,m), 7.67(1H,s), 7.91(1H,s), 8.10(1H,d,J=8.4 Hz), 8.25(1H,d,J=8.4 Hz), 8.32 (1H,s), 8.69(1H,s).

MS: MH⁺=472.

EXAMPLE 114

Preparation of a compound represented by the structural formula:

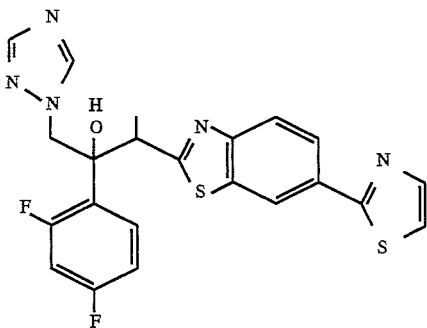

The compound (264 mg) obtained in Example 111, bromoacetoaldehyde dimethylacetal (390 µl) and one drop of concentrated sulfuric acid were heated and refluxed for 1 hour in ethanol (2.5 ml). After bromoacetoaldehyde dimethylacetal (390 µl) was added to heat and reflux the mixture further for 1 hour, ethyl acetate and water were added to the liquid reaction mixture to separate the mixture into liquids. The resultant organic layer was washed with water and dried, and the solvent was distilled out. Hexane was added to the residue, and precipitate formed was collected by filtration, thereby obtaining the intended compound (180 mg). Physical properties of this compound are described below.

mp: 153°–158° C.

NMR: δ solvent (CDCl₃) 1.28(3H,d,J=7.2 Hz), 4.12(1H, q,J=7.2 Hz), 4.31(1H,d,J=14.2 Hz), 4.96(1H,d,J=14.2 Hz), 5.89(1H,s), 6.78–6.25(2H,m), 7.40(1H,d,J=3.4 Hz), 7.66 (1H,s), 7.89(1H,s), 7.92(1H,d,J=3.4 Hz), 8.09(1H,d,J=0.4 Hz), 8.10(1H,d,J=1.6 Hz), 8.75(1H,dd,J=0.4 Hz,1.6 Hz).

MS: MH⁺=470.

EXAMPLE 115

Preparation of compounds represented by the structural formula A:

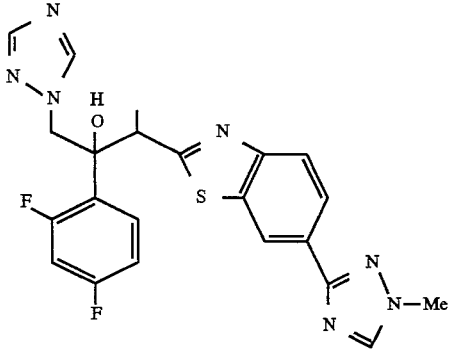

and the structural formula B:

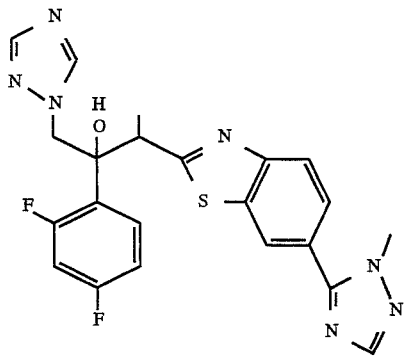

The compound (453 mg) obtained in Example 113 was dissolved in acetone (4.5 ml), and potassium carbonate powder (138 mg) and iodomethane (62 µl) were added to the solution. The resultant mixture was stirred overnight at room temperature. The mixture was subjected to extraction with ethyl acetate-water. The resultant organic layer was washed with water and dried, and the solvent was distilled out. The residue was purified through a silica gel column (dichloromethane:methanol=50:1→30:1) and then separated and purified through an ODS column (methanol:water =60:40→65:35), thereby obtaining a compound (192 mg) of the structural formula A and a compound (52 mg) of the structural formula B. Physical properties of these compounds are described below.

A
mp: 180°–190° C.
NMR: δ solvent (CDCl₃)
 1.27(3H,d,J=7.0 Hz), 4.01(3H,s), 4.11(1H,q,J=7.0 Hz),
 4.32(1H,d,J=14.0 Hz), 4.94(1H,d,J=14.0 Hz), 5.99(1H,s),
 6.77–6.86(2H,m), 7.50–7.57(1H,s), 7.65(1H,s),
 7.91(1H,s), 8.08(1H,d,J=8.4 Hz), 8.10(1H,s),
 8.27(1H,dd,J=8.4 Hz,1.6 Hz), 8.67(1H,d,J=1.6 Hz).
MS: MH⁺=454.
B
mp: 196°–197° C.
NMR: δ solvent (CDCl₃)
 1.29(3H,d,J=7.2 Hz), 4.07(3H,s), 4.15(1H,q,J=7.2 Hz),
 4.30(1H,d,J=14.2 Hz), 4.97(1H,d,J=14.2Hz), 5.82(1H,s),
 6.79–6.86(2H,m), 7.50–7.58(1H,m), 7.68(1H,s),
 7.82(1H,dd,J=1.8 Hz,8.4Hz), 7.87(1H,s), 7.99(1H,s),
 8.16(1H,d,J=8.4 Hz), 8.281 H,d,J=1.8 Hz).

EXAMPLE 116

Preparation of a compound represented by the structural formula:

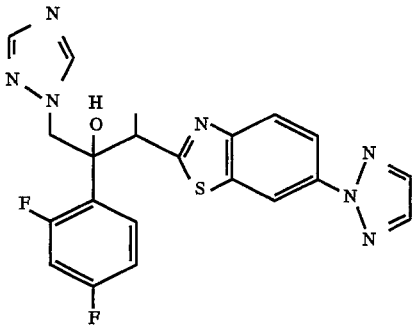

The intended compound (120 mg) was obtained in accordance with the same procedure as that described in Example 106 except that 2-ethyl-6-(1,2,3-triazol-2-yl)-benzothiazole (529 mg), which was the raw material 5 prepared in Preparation Example 7, was used in place of 2-ethyl-6-chlorobenzothiazole. Physical properties of this compound are described below.
State: Oily.
NMR: δ solvent (CDCl₃)
 1.29(3H,d,J=7.1 Hz), 4.12(1H,q,J=7.1 Hz),
 4.32(1H,d,J=14.2 Hz), 4.97(1H,d,J=14.2 Hz),
 5.87(1H,brs), 6.79–6.83(2H,m), 7.50–7.58(1H,m),
 7.67(1H,s), 7.87(2H, s), 7.89(1H,s),
 8.12 (1H,d,J=9.0 Hz), 8.30(1H,dd,J=8.8,2.2 Hz),
 8.65 (1H,d,J=2.2 Hz).

EXAMPLE 117

Preparation of a compound (1:1 diastereomer mixture) represented by the structural formula:

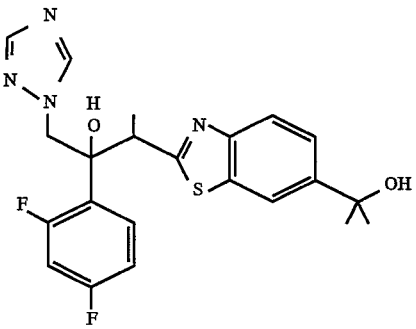

2-Ethyl-6-methoxycarbonylbenzothiazole was prepared in accordance with the same procedure as in Preparation Example 7. This compound was dissolved in 1 ml of diethyl ether, and methylmagnesium iodide (2.0 M diethyl ether solution, 1.2 ml) was added to the solution at 0° C. After stirring the mixture at room temperature, it was added with a saturated aqueous solution of ammonium chloride and subjected to extraction with ethyl acetate. The resulting organic layer was washed with water and then saturated saline, and the solvent was distilled out under reduced pressure. The thus-obtained crude product was purified by column chromatography on silica gel to obtain (2-methyl-2-(2-ethylbenzothiazol-6-yl)ethanol) (138 mg). The intended compound (1:1 diastereomer mixture) was obtained in accordance with the same procedure as that described in Example 19 except that this product was used instead of 2-ethyl-6-chlorobenzothiazole and n-butyllithium was used in an amount twice as much as that of Example 116. Physical properties of this compound are described below.
mp:
State: Solid.
NMR: δ solvent (CDCl₃)
 1.25(1.5 H,d,J=7.2 Hz), 1.60(3H,s), 1.67(3H,s),
 1.80(1.5H,d,J=8.4 Hz), 4.05–4.17(1H,m),
 4.27(0.5H,d,J=14.4 Hz), 4.71(0.5 H,d,J=14.0 Hz),
 4.90–4.95(1H,n), 6.02(0.5H,s), 6.13(0.5H,d,J=1.6 Hz),
 6.44–6.51(0.5H,m), 6.63–6.70(0.5H,m),
 6.63–6.70(0.5H,m), 6.76–6.85(1H,m), 7.10–7.17(0.5 H,m),
 7.50–7.56(1H,m), 7.61–7.65(0.5H,m), 7.64(0.5H,s),
 7.66(0.5H,s), 7.84(0.5H,d,J=8.8 Hz), 7.89(0.5H,s),
 7.91(0.5H,d,J=1.6 Hz), 8.00(0.5 H,d,J=8.8 Hz),
 8.06(0.5H,s), 8.10(0.5H,d,J=1.6 Hz).
MS: MH⁺=445.

EXAMPLE 118

Preparation of a compound (1:1 diastereomer mixture) represented by the structural formula:

The same 2-ethyl-6-methoxycarbonylbenzcthiazole (699 mg) as that used in Example 117 was dissolved in a 1:1 mixed solvent (20 ml) of water and methanol, and 1N aqueous NaOH (8 ml) was added to the solution, followed by heating and refluxing for 2.5 hours. The reaction mixture was added with 8 ml of 1N HCl and then common salt and subjected to extraction with ethyl acetate. After the extract was washed with saturated saline, the solvent was distilled out under reduced pressure, thereby obtaining 6-carboxy-2-ethylbenzothiazole (642 mg). This product (1.957 g) was dissolved in xylene (50 ml) without purifying it, and 2-amino-2-methyl-1-propanol (6 ml) was added to the solution. The resulting mixture was then heated and refluxed for 3 days by means of a Dean-Stack trap. The solvent was distilled under reduced pressure out of the liquid reaction mixture, and the resultant residue was purified By column chromatography on silica gel, thereby obtaining an intermediate compound represented by the structural formula:

Using this intermediate compound, the intended compound was obtained in accordance with the same procedure as in Example 106. Physical properties of this compound are described below.

mp:
State: Solid.
NMR: δ solvent (CDCl$_3$)
  1.27(1.5H,d,J=6.8 Hz), 1.38(3H,s), 1.42(3H,s),
  1.70(1.5H,d,J=6.8 Hz), 4.08–4.18(1H,m), 4.12(1H,s),
  4.18(1H,s), 4.29(0.5H,d,J=14.4 Hz),
  4.74 (0.5H,d,J=14 Hz), 4.94 (0.5H,d,J=14.4 Hz),
  4.95(0.5H,d,J=14 Hz), 5.90(0.5H,s),
  5.94(0.5H,d,J=1.6 Hz), 6.43–6.49(0.5H,m),
  6.62–6.69(0.5H,m), 6.77–6.85(1H,m), 7.07–7.14(0.5H, m),
  7.49–7.57(0.5H,m), 7.66(0.5H,s), 7.68(0.5H,s),
  7.89(0.5H,d,J=8.4 Hz), 7.89(0.5H,s),
  8.00(0.5H,dd,J=1.6,8.4 Hz), 8.03(0.5H,d,J=8.4 Hz),
  8.05(0.5H,s), 8.10(0.5H,dd,J=1.6,8.4 Hz),
  8.35(0.5H,d,J=1.6 Hz), 8.53 (0.5H,d,J=1.6 Hz).
MS: MS$^+$=484.

EXAMPLE 119

Preparation of a compound (I) represented by the structural formula:

and another compound (II) which is a diastereomer thereof:

2-Ethyl-6-methylthiobenzothiazole was prepared in accordance with the same procedure as that described in Preparation Example 7, and a mixture of diastereomers which were the intended compounds was prepared in accordance with the same procedure as in Example 106 except that this product was, used. The mixture was subjected to chromatography on silica gel to separate the compound (I) and the compound (II), which was a diastereomer thereof, from each other.

(I)
State: Solid.
NMR: δ solvent (CDCl$_3$)
  1.24(3H,d,J=7.0 Hz), 2.57(3H,s), 4.06(1H,q,J=7.0 Hz),
  4.27(1H,d,J=14.2 Hz), 4.92 (1H,d,J=14.2 Hz), 5.93 (1H, s),
  6.76–6.84(2H,m), 7.42(1H,dd,J=2.0,8.4 Hz),
  7.47–7.55(1H,m), 7.65(1H,s), 7.76(1H,d,J=2.0),
  7.88(1H,s), 7.92(1H,d,J=8.4 Hz).
MS: MH$^+$=433.

(II)
State: Solid.
NMR: δ solvent (CDCl$_3$)
  1.24(3H,d,J=7.0 Hz), 2.57(3H,s), 4.06(1H,q,J=7.0 Hz),
  4.27(1H,d,J=14.2 Hz), 4.92(1H,d,J=14.2 Hz), 5.93(1H,s),
  6.76–6.84(2H,m), 7.42(1H,dd,J=2.0,8.4 Hz),
  7.47–7.55(1H,m), 7.65(1H,s), 7.76(1H,d,J=2.0),
  7.88(1H,s), 7.92(1H,d,J=8.4 Hz).
MS: MH$^+$=433.

EXAMPLE 120

Preparation of a compound (I) represented by the structural formula:

and another compound (II) which is a diastereomer thereof:

119

The above compound (I) and the compound (II) which was a diastereomer thereof were obtained from the compounds obtained in Example 119 and the diastereomer thereof, respectively, in accordance with the same procedure as that described in Example 99. Physical properties of these compounds are described below.

(I)
State: Solid.
NMR: δ solvent (CDCl₃)
1.29(3H,d,J=7.2 Hz), 3.13(3H,s), 4.18(1H,q,J=7.2 Hz),
4.24(1H,d,J=14.12 Hz), 4.98(1H,d,J=14.2 Hz), 5.68(1H, s),
6.79–6.86(2H,m), 7.49–7.56(1H,m), 7.70(1H,s),
7.84(1H,s), 8.06(1H,dd,J=2.0,8.8 Hz),
8.19(1H,d,J=8.8 Hz), 8.58(1H,d,J=2.0 Hz).
MS: MH⁺=465.

(II)
State: Solid.
NMR: δ solvent (CDCl₃)
1.71(3H,d,J=6.8 Hz), 3.08(3H, s), 4.22(1H,q,J=6.8 Hz),
4.73(1H,d,J=14.0 Hz), 4.98(1H,d,J=14.0 Hz), 5.72(1H, s),
6.47–6.54(1H,m), 6.64–6.71(1H,m), 7.12–7.19(1H,m),
7.72(1H,s), 7.96(1H,dd,J=1.7,8.8 Hz), 8.02(1H,s),
8.04(1H,d,J=8.8 Hz), 8.41(1H,brd,J=1.7 Hz).
MS: MH⁺=465.

EXAMPLE 121

Preparation of a compound represented by the structural formula:

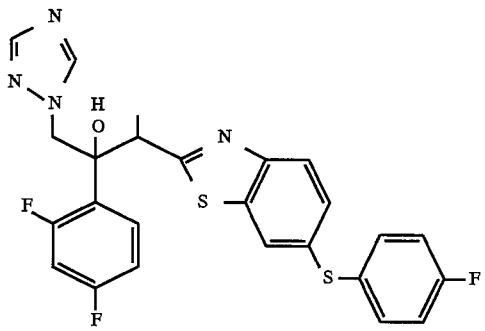

The intended compound was prepared in accordance with the same procedure as that described in Example 106 except that 2-ethyl-6-(4-fluorophenylthio)benzothiazole prepared in accordance with the same procedure as that described in Preparation Example 6 was used in place of 2-ethyl-6-chlorobenzothiazole. Physical properties of this compound are described below.
State: Solid.
NMR: δ solvent (CDCl₃)
1.24(3H,d,J=7.2 Hz), 4.07(1H,q,J=7.2 Hz),
4.26(1H,d,J=14.4 Hz), 4.92(1H,d,J=14.4 Hz), 5.84(1H,s),
6.76–6.84 (2H,m), 7.06 (2H,br-dd,J=8.6,8.6 Hz),
7.39–7.44(3H,m), 7.47–7.55(1H,m), 7.66(1H,s),
7.77(1H,d,J=1.6 Hz), 7.86(1H,s), 7.93(1H,d,J=8.8 Hz).
MS: MH⁺=513.

EXAMPLE 122

Preparation of a compound (I) represented by the structural formula:

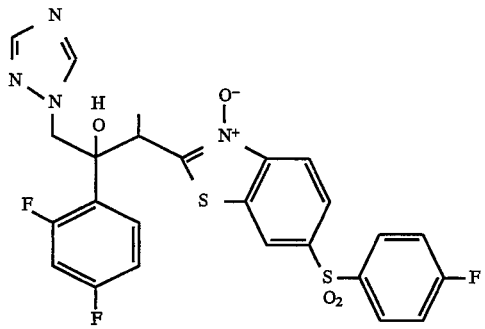

and
another compound (II) represented by the structural formula:

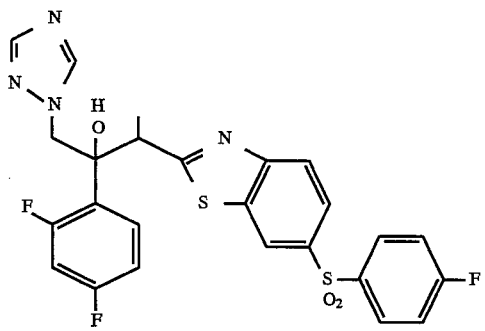

A mixture of the above compounds was prepared from the compound, which had been prepared according to Example 121, in accordance with the same procedure as that described in Example 99. This mixture was subjected to chromatography on silica gel to separate the compounds from each other, thereby obtaining the individual compounds. Physical properties of these compounds are described below.

(I)
State: Solid.
NMR: δ solvent (CDCl₃)
1.27(3H,d,J=7.2 Hz), 4.22 (1H,d,J=14.4 Hz),
4.63 (1H,q,J=7.2 Hz), 5.11(1H,d,J=14.4 Hz), 6.56(1H, brs),
6.76–6.87(2H,m), 7.23 (2H,br-dd,J=8.4,8.4 Hz),
7.46–7.54(1H,m), 7.68(1H,s), 7.92(1H,s),
7.99–8.04(2H,m), 8.12 (1H,dd,J=1.6,8.4 Hz),
8.32 (1H,d,J=8.4 Hz), 8.51 (1H,br-d,J=1.6 Hz).
MS: MH⁺=561.

(II)
State: Solid.
NMR: δ solvent (CDCl₃)
1.26(3H,d,J-7.2 Hz), 4.14(1H,q,J=7.2 Hz);
4.19(1H,d,J=14.4 Hz), 4.94(1H,d,J=14.4 Hz),
5.64(1H,s), 6.78–6.85(2H,m),
7.20(2H,br-dd,J=8.6,8.6 Hz), 7.47–7.54(1H,m),
7.68(1H,s), 7.81(1H,s), 7.98–8.03(3H,m),
8.12 (1H,d,J=8.8 Hz), 8.58 (1H,d,J=2.0 Hz).
MS: MH⁺=545.

EXAMPLE 123

Preparation of a compound represented by the structural formula:

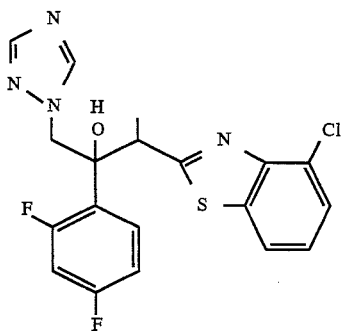

The intended compound was prepared in accordance with the same procedure as that described in Example 106 except that 2-ethyl-4-chloro-benzothiazole was used in place of 2-ethyl-6-chloro-benzothiazole. Physical properties of this compound are described below.
State: Oily.
NMR: δ solvent (CDCl₃)
 1.26(3H,d,J=8.0 Hz), 4–19(1H,q,J=8.0 Hz),
 4.34(1H,d,J=15.2 Hz), 4.96(1H,d,J=15.2 Hz),
 5.92(1H,brs), 6.78–6.84(2H,m), 7.34–7.40(1H,m),
 7.50–7.58(2H,m), 7.68(1H,s), 7.78–7.58(2H,m),
 7.68(1H,s), 7.78–7.85(1H,m), 7.92(1H,s).

EXAMPLE 124

Preparation of a compound represented by the structural formula:

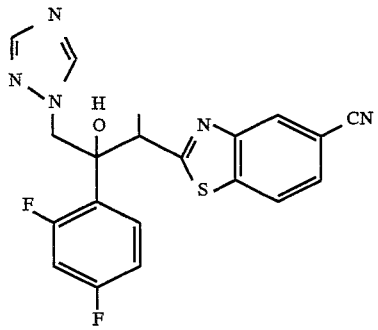

The intended compound was prepared in accordance with the same procedure as that described in Example 109 except that 2-ethyl-4-cyano-benzothiazole was used in place of 2-ethyl-6-cyano-benzothiazole. Physical properties of this compound are described below.
State: Oily.
NMR: δ solvent (CDCl₃)
 1.26(3H,d,J=7.1 Hz), 4.15(1H,q,J=7.1 Hz),
 4.22(1H,d,J=14.2 Hz), 4.98(1H,d,J=14.2 Hz),
 5.63(1H,brs), 6.78–6.86(2H,m), 7.48–7.56(1H,m),
 7.67(1H,dd,J=8.2,1.5 Hz), 7.70(1H,s), 7.84(1H,s),
 8.03(1H,d,J=8.2 Hz), 8.33(1H,d,J=1.5 Hz).

EXAMPLE 125

Preparation of a compound represented by the structural formula:

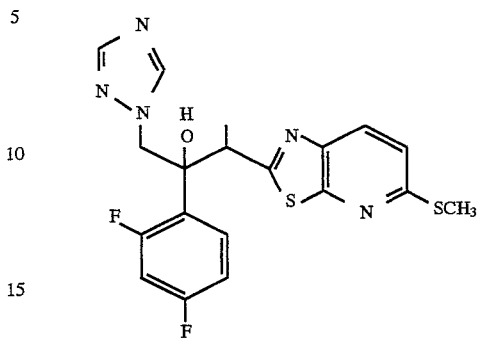

2-Ethyl-6-chloro-7-azabenzothiazole (3.16 g) and sodium thiomethoxide (1.67 g) were reacted for 1 hour at 90° C. in N-methylpyrrolidone (9 ml). After cooling the reaction mixture, water and ethyl acetate were added to the reaction mixture to separate the mixture into liquids. The resulting organic layer was washed with water and dried, and the solvent was distilled out. The residue was purified through a silica gel column (hexane:ethyl acetate=10:1), thereby obtaining an intermediate compound, 2-ethyl-6-thiomethoxy-7-azabenzothiazole (2.25 g). Using this intermediate compound, the intended compound was obtained in accordance with the same procedure as in Example.106. Physical properties of this compound are described below.
mp: 185°–186° C.
NMR: δ solvent (CDCl₃)
 1.25(3H,d,J=7.2 Hz), 2.65(3H,s), 4.03(1H,q,J=7.2 Hz),
 4.30(1H,d,J=14.2 Hz), 4.94(1H,d,J=14.2 Hz), 5.75(1H,s),
 6.77–6.85(2H,m), 7.31(1H,d,J=8.4 Hz), 7.48–7.55(1H, m),
 7.68(1H,s), 7.86(1H,s), 8.02(1H,d,J=8.4 Hz).

EXAMPLE 126

Preparation of a compound represented by the structural formula:

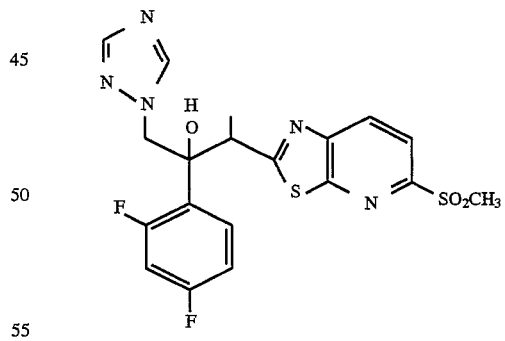

The compound (400 mg) obtained in Example 125 was dissolved in dichloromethane (4 ml), and metachloroperbenzoic acid (476 mg) was added to the solution, followed by stirring for 1.5 hours at room temperature. The reaction mixture was washed successively with aqueous sodium hydrogen-carbonate to which dichloromethane was added, and water, and dried. The solvent was distilled out to obtain the intended product (452 mg). Physical properties of this compound are described below.
mp: 211°–214° C.
NMR: δ solvent (CDCl₃)

1.30(3H,d,J=7.0 Hz), 3.32(3H,s), 4.14(1H,q,J=7.0 Hz), 4.23(1H,d,J=14.4 Hz), 5.01(1H,d,J=14.4 Hz), 5.59(1H,s), 6.80–6.86(2H,m), 7.48–7.56(1H,m), 7.72(1H,s), 7.82(1H,s), 8.25(1H,d,J=8.4 Hz), 8.47(1H,d,J=8.4 Hz).
MS: MH⁺=466.

EXAMPLE 127

Preparation of a compound represented by the structural formula:

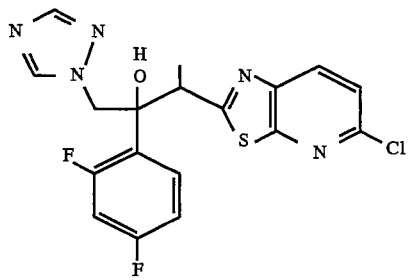

The intended compound was prepared in accordance with the same procedure as that described in Example 125 except that 2-ethyl-6-chloro-7-azabenzothiazole was used as an intermediate compound. Physical properties of this compound are described below.
mp: 177°–178° C.
NMR: δ solvent (CDCl$_3$)
1.27(3H,d,J=7.2 Hz), 4.07(1H,d,J=7.2 Hz), 4.27(1H,d,J=14.0 Hz), 4.96(1H,d,J=14.0 Hz), 5.63(1H,s), 6.78–6.85(2H,m), 7.47(1H,d,J=8.4 Hz), 7.48–7.55(1H,m), 7.70(1H,s), 7.83(1H,s), 8.19 (1H,d,J=8.4 Hz).

EXAMPLE 128

Preparation of a compound represented by-the structural formula:

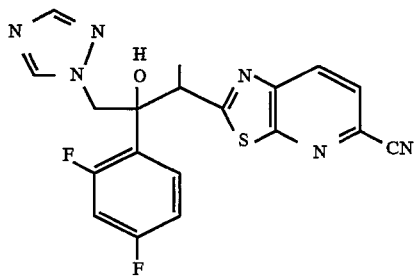

2-Ethyl-7-azabenzothiazole (2.95 g) was dissolved in dichloromethane (30 ml), and meta-chloroperbenzoic acid (4.7 g) was added to the solution at room temperature. After 3.5 hours, meta-chloroperbenzoic acid (2.3 g) was further added. After completion of a reaction, the reaction mixture was treated with an aqueous solution of sodium sulfite while chilling with ice water. The thus-treated reaction mixture was diluted with dichloromethane, and the resultant organic layer was washed with aqueous sodium hydrogencarbonate, water and saline in that order, and dried. The solvent was distilled out to obtain 2-ethyl-7-azabenzothiazole-7-oxide (2.69 g). This compound was added to dichloromethane (27 ml), and dimethylaminocarbamoyl chloride (4.16 g), trimethylsilyl cyanide (5.69 ml) and triethylamine (6.3 ml) were successively added to conduct a reaction for 8 hours at room temperature. Trimethylsilyl cyanide (2.5 ml) and dimethylaminocarbamoyl chloride (2.5 ml) were further added. After the reaction was conducted for 2 days at room temperature, aqueous sodium hydrogencarbonate was added to the reaction mixture, followed by stirring for 1 hour. The reaction mixture was subjected to extraction with ethyl acetate, and the resultant organic layer was washed with water, dried and evaporated. After purifying the residue through a silica gel column (eluthion with dichloromethane: methanol=200:1), recrystallization from dichloromethaneisopropyl ether was conducted to form 2-ethyl-6-cyano-7-azabenzothiazole (1.37 g). The intended compound was obtained in accordance with the same procedure as that of Example 106 except that the above compound was used in place of 2-ethyl-6-chlorobenzothiazole. Physical properties of this compound are described below.
mp: 170°–173° C.
NMR: δ solvent (CDCl$_3$)
1.30(JH,d,J=7.0 Hz), 4.13(1H,qd,J=7.0 Hz, 0.8 Hz), 4.25(1H,d,J=14.0 Hz), 4.98(1H,d,J=14.0 Hz), 5.59(1H,d,J=0.8 Hz), 5.59(1H,d,J=0.8 Hz), 6.79–6.86 (2H,m), 7.49–7.56(1H,m), 7.72(1H,s), 7.81(1H,s), 7.84(1H, d,J=S.4 Hz), 8.35(1H,d,J=8.4 Hz).
MS: MH⁺=413.

EXAMPLE 129

Preparation of a compound represented by the structural formula:

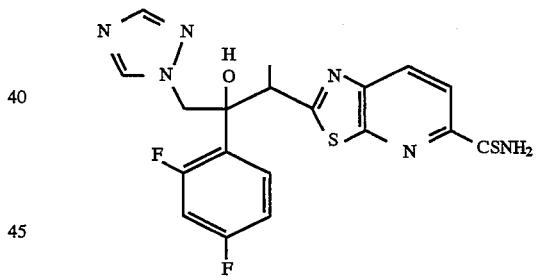

The intended compound was prepared from the compound, which had been prepared according to Example 128, in accordance with the same procedure as that described in Example 111. Physical properties of this compound are described below.
State: Solid.
NMR: δ solvent (CDCl$_3$) 1.30(3H,d,J=7.2 Hz), 4.12(1H,q, J=7.2 Hz), 4.28(1H,d,J-14.4 Hz), 5.00(1H,d,J=14.4 Hz), 5.65(1H,s), 6.80–6.87(2H,m), 7.49–7.56(1H,m), 7.70 (1H,s),
7.70–7.76(1H,brs), 7.80(1H,s), 8.33(1H,d,J=8.8 Hz), 8.91(1H,d,J=8.8 Hz), 9.32–8.38(1H,br-s).

EXAMPLE 130

Preparation of a compound represented by the structural formula:

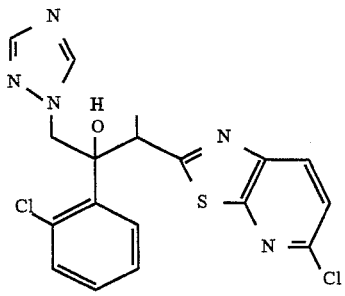

The intended compound was prepared in accordance with the same procedure as that described in Example 127 except that 1-(1H-1,2,4-triazol-1-yl)-2'-chloroacetophenone was used in place of 1-(1H-1,2,4-triazol-1-yl)-2',4'-difluoroacetophenone. Physical properties of this compound are described below.
State: Solid.
NMR: δ solvent (CDCl$_3$)
1.22(3H,d,J=7.2 Hz), 4.22(1H,d,J=14.4 Hz),
4.67(1H,q,J=7.2 Hz), 5.55(1H,s), 5.60(1H,d,J=14.4 Hz),
7.18–7.22(2H,m), 7.34–7.38(1H,m), 7.46(1H,d,J=8.8 Hz),
7.68(1H,s), 7.69–7.73(1H,2), 7.81(1H,s),
8.20 (1H, d,J=8.8 Hz).

EXAMPLE 131

Preparation of a compound represented by the structural formula:

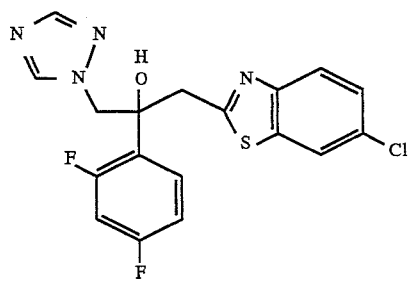

The intended compound was prepared in accordance with the same procedure as that described in Example 106 except that 2-methyl-6-chlorobenzothiazole was used in place of 2-ethyl-6-chlorobenzothiazole. Physical properties of this compound are described below.
State: Solid.
NMR: δ solvent (CDCl$_3$)
3.43(1H,d,J=15.2 Hz), 3.88(1H,d,J=15.2 Hz),
4.65(1H,d,J=14.2 Hz), 4.70(1H,d,J=14.2 Hz), 6.03(1H,s),
6.69–6.74(1H,m), 6.76–6.81(1H,m),
7.40(1H,dd,J=8.8 Hz,2.0 Hz), 7.42–7.50(1H,m),
7.75(1H,dd,J=2.0 Hz), 7.82(1H,d,J=8.8 Hz), 7.85(1H,s),
8.18(1H,s).

EXAMPLE 132

Preparation of a compound represented by the structural formula:

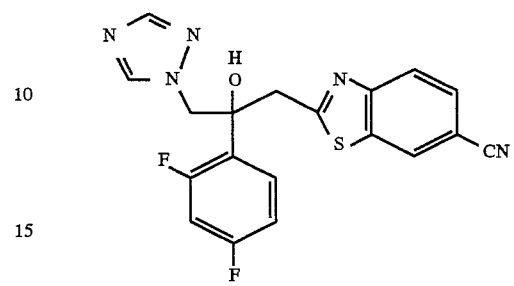

The intended compound was prepared in accordance with the same procedure as that described in Example131 except that 2-methyl-6-cyanobenzothiazole was used in place of 2-methyl-6-chlorobenzothiazole. Physical properties of this compound are described below.
mp: 176°–178° C.
NMR: δ solvent (CDCl$_3$)
3.52(1H,d,J=15.4 Hz), 3.95(1H,d,J=15.4 Hz), 4.69(2H, s),
5.87(1H,s), 6.71–6.82(1H,m), 7.51–7.45(1H,m),
7.69(1H,dd,J=1.6 Hz,8.6 Hz), 7.86(1H,s),
7.99(1H,dd,J=0.4 Hz,8.6 Hz), 8.13(1H,dd,J=0.4 Hz,1.6 Hz),
8.15(1H,s).

EXAMPLE 133

Preparation of a compound represented by the structural formula:

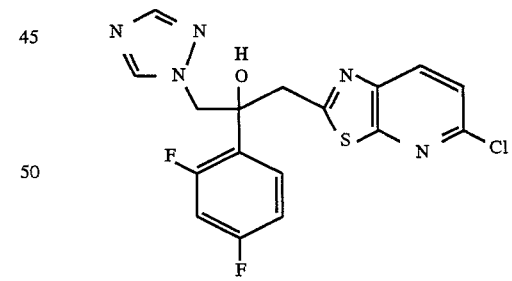

The intended compound was prepared in accordance with the same procedure as that described in Example 127 except that 2-methyl-6-chloro-7-azabenzothiazole was used in place of 2-ethyl-6-chloro-7-azabenzothiazole. Physical properties of this compound are described below.
mp: 145°–147° C. (MeOH).
NMR: δ solvent (CDCl$_3$)
3.47(1H,d,J=15.2 Hz), 3.90(1H,d,J=15.2 Hz), 4.69(2H,s),
5.76(1H,s), 6.70–6.83(2H,m), 7.39(1H,d,J=8.4 Hz),
7.42–7.49(1H,m), 7.86(1H,s), 8.08(1H,d,J=8.4 Hz),
8.13 (1H,s).

EXAMPLE 134

Preparation of a compound represented by the structural formula:

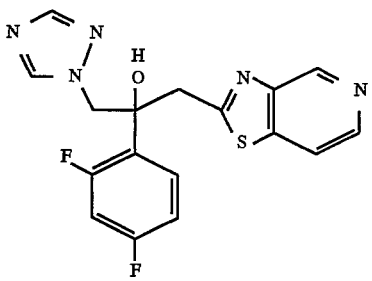

3-Nitro-4-chloropyridine hydrochloride (2038 mg) was dissolved in ethanol (42 ml), and sodium hydrogensulfide (2148 mg) was added to the solution, followed by stirring for 40 minutes at room temperature. An aqueous solution of sodium hydrosulfite (6.67 g) was added to this reaction mixture, and the resultant mixture was heated and stirred at 80° C. for 12 hours. After insoluble matter was separated by filtration, the solution was concentrated. The concentrate was dissolved in methanol-water, and the solution was mixed with silica gel and dried under reduced pressure. Thereafter, elution was conducted with 5:1 chloroform-methanol and then 1:1 chloroform-methanol, thereby obtaining 3-amino-4-mercaptopyridine (892 mg). To this product, 7 ml of ethyl acetate and molecular sieve 4Å were added, and the resultant mixture was heated and refluxed for 20 minutes in a nitrogen atmosphere. The reaction mixture was dried under reduced pressure and dissolved in methanol. The solution was caused to be adsorbed on silica gel. This solution was eluted with 50:1 chloroform-methanol, thereby obtaining 590 mg of 2-methyl-5-azabenzothiazole. The intended compound was obtained in accordance with the same procedure as that described in Example 131 except that the above-described 2-methyl-5-azabenzothiazole was used in place of 2-methyl-6-chlorobenzothiazole. Physical properties of this compound are described below.

mp: 137°–148 ° C.

NMR: δ solvent (CD$_3$OD)

3.69 (1H,d,J=14.8 Hz), 4.08 (1H,d,J=14.8 Hz), 4.77(1H,d,J=14.4 Hz), 4.87(1H,d,J=14.4 Hz), 6.71–6.84(1H,m), 6.92–7.04(1H,m), 7.32–7.46(1H,m), 7.83(1H,s), 7.97(1H,d,J=5.2 Hz), 8.37(1H,d,J=5.2 Hz), 8.37(1H,s), 9.06(1H,s).

EXAMPLE 135

Preparation of a compound represented by the structural formula:

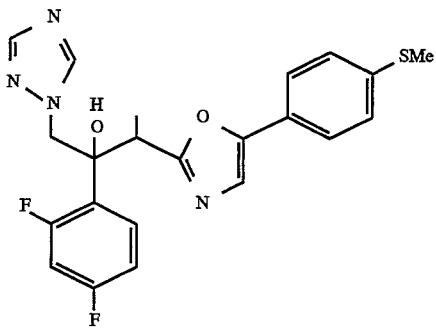

Sodium azide (2301 mg) was dissolved in dimethyl sulfoxide (60 ml), and 2-bromo-4'-thiomethylacetophenone (3000 mg) was added to this solution, followed by stirring for 20 minutes at room temperature. The reaction mixture was poured into 200 ml of ice water and then subjected to extraction with ethyl acetate (200 ml×5). The extract was dried over anhydrous magnesium sulfate, concentrated under reduced pressure and then purified by column chromatography on silica gel (hexane - hexane-ethyl acetate= 8:1), thereby obtaining 2-azide-4'-thiomethylacetophenone (2155 mg). After a lithium diisopropylamine solution generated from diisopropylamine (1.75 ml) and a 1.6 M hexane solution (7.8 ml) of n-buthyllithium in 47 ml of tetrahydrofuran while chilling with ice water was chilled to –78° C., a tetrahydrofuran solution (19 ml) of 2-azide-4'-thiomethylacetophenone (2155 mg) was added dropwise thereto over 5 minutes, followed by stirring for 1 hour at –78° C. Propionyl chloride (1.81 ml) was then added dropwise, and the resultant mixture was left to stand at –78° C. for 10 minutes, heated to room temperature as it is, and stirred for 10 minutes at room temperature. The reaction mixture was poured into ice water and subjected to extraction with ether (300 ml×3). The extract was dried over anhydrous magnesium sulfate and then concentrated under reduced pressure. The resultant oily substance was purified by column chromatography on silica gel (hexane→hexane:ethyl acetate= 10:1), thereby obtaining 2-azide-1-(4'-thiomethylphenyl) vinyl propionate (1.98 g). This product was dissolved in cyclohexane (38 ml), and an ester of phosphorous acid was added to the solution. The resultant mixture was stirred for 1 hour at room temperature in a nitrogen atmosphere and then for 20 hours at 90° C. with heating. The reaction mixture was purified by column chromatography on silica gel (hexane→hexane:ethyl acetate=30:1) as it is, thereby obtaining 2-ethyl-5-(4-thiomethylphenyl)oxazole (630 mg). Using this compound in place of 2-ethyl-6-chlorobenzothiazole, the intended compound was obtained in accordance with the same procedure as that described in Example 106. Physical properties of this compound are described below.

State: Oily.

NMR: δ solvent (CDCl₃)
1.55(3H,d,J=8.0 Hz), 2.50(3H,s), 3.88(1H,q,J=8.0 Hz), 4.69(1H,d,J=13.3 Hz), 4.98(1H,d,J=13.3 Hz), 5.56(1H,brs), 6.60–6.72(2H,m), 7.20–7.26(2H,m), 7.22–7.34(1H,m), 7.27(2H,s), 7.33–7.38(2H,m), 7.70(1H,s), 8.30(1H,s).

EXAMPLE 136

Preparation of a compound represented by the structural formula:

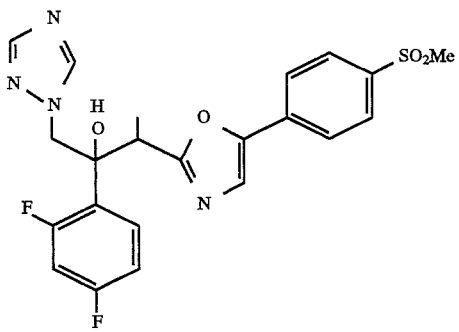

The product (77 mg) of Example 135 was dissolved in dichloromethane (6.0 ml), and meta-chloroperbenzoic acid (156 mg) was added to the solution while chilling with ice water. After heating the mixture to room temperature, it was stirred for 1 hour. To the reaction mixture, were added a saturated aqueous solution of sodium thiosulfate and a saturated aqueous solution of sodium hydrogencarbonate. Dichloromethane (10 ml) was added to the resultant mixture to separate the mixture into liquids. The resulting water layer was subjected to further extraction with dichloromethane (10 ml×2). The organic layers were put together, washed with saturated saline, dried over anhydrous magnesium sulfate and then concentrated under reduced pressure. The thus-obtained oily substance was purified by column chromatography on silica gel (hexane-ethyl acetate= 4:1→dichloromethane-methanol=10:1), thereby obtaining the intended compound (54 mg). Physical properties of this compound are described below.

State: Oily.

NMR: δ solvent (CDCl₃)
1.60(3H,d,J=7.2 Hz), 3.07(3H,s), 3.91(1H,q,J=7.1 Hz), 4.71(1H,d,J=14.1 Hz), 5.00(1H,d,J=14.1 Hz), 5.40–5.50(1H,brs), 6.62–6.72(2H,m), 7.26–7.33(1H,m), 7.31(1H, s), 7.60–7.64(2H,m), 7.73(1H,s), 7.92–7.97(2H,m), 8.05(1H, s).

MS: m/e FAB 475 ( MH⁺).

EXAMPLE 137

Preparation of a compound represented by the structural formula:

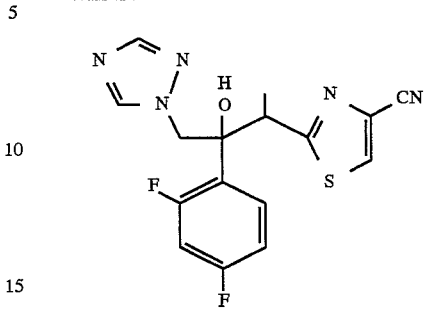

and a diastereomer thereof:

A solution of 2-ethyl-4-cyano-5-trimethylsilylthiazole (1.58 g) in 10 ml of tetrahydrofuran was added dropwise to 20 ml of a tetrahydrofuran solution of lithium diisopropylamide (prepared from 1.40 ml of diisopropylamine and 3.2 ml of butyllithium (1.6 M hexane solution)) at −65° C. Then, 10 ml tetrahydrofuran solution of (1H-1,2,4-triazol-1-yl)-2, 4-difluorophenylacetophenone was added dropwise at −65° C. After stirring the mixture for 1.5 hours, an aqueous solution of ammonium chloride was added thereto, and the resulting mixture was separated with ethyl acetate and water into liquids. The resultant organic layer was washed with water and dried, and the solvent was distilled out. The residue was dissolved in 20 ml or tetrahydrofuran, and 20 ml of a tetrahydrofuran solution (1.0 M) of tetrabutylammonium fluoride was added to the solution, followed by stirring for 1 hour at room temperature. After the reaction mixture was separated with ethyl acetate and water into liquids, the resultant organic layer was washed with water, dried and concentrated to dryness. The residue was purified by column chromatography on silica gel (dichloromethane:methanol= 200:1), thereby obtaining a single diastereomer compound (I) (464 mg). A fraction containing the other diastereomer and (1H-1,2,4-triazol-1-yl)-2,4-difluoroacetophenone was treated with sodium borohydride in methanol and subjected to separation through a silica gel column, thereby obtaining 564 mg of the other diastereomer compound (II). Physical properties of these compounds are described below.

(I)
mp: 198°–205° C.

NMR: δ solvent (CDCl₃)
1.20(3H,d,J=7.1 Hz), 4.06(1H,q,J=14.4 Hz), 4.08(1H,q,J=7.1 Hz), 4.96(1H,d,J=14.4 Hz), 5.41(1H, s), 6.77–6.83(2H,m), 7.42–7.49(1H,m), 7.75(1H, s), 7.80(1H,s), 8.05(1H,s).

MS: MH⁺=362.

(II)
mp: 191°–194° C.

NMR: δ solvent (CDCl₃)
1.61(3H,d,J=7.1 Hz), 4.08 (1H,q,J=7.1 Hz), 4.66(1H,d,J=14.0 Hz), 4.98(1H,d,J=14.0 Hz), 5.37(1H,s), 6.58–6.70(2H,m), 7.12–7.18(1H,m), 7.75(1H,s), 7.79(1H,s), 7.97(1H,s).

MS: MH⁺=362.

EXAMPLE 138

Preparation of a compound represented by the structural formula:

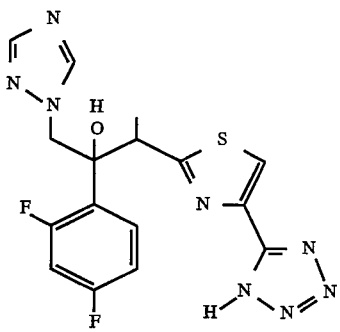

In 2 ml of N-methyl-pyrrolidone, were dissolved 150 mg of the compound prepared in Example 137, and 54 mg of NaN₃ and 115 mg of Et3N-HCl were added to the solution, followed by heating for 5 hours at an external temperature of 100° C. on an oil bath. Water was added to the liquid reaction mixture, which was then subjected 3 times to extraction with AcOEt. After the extract was washed with water and then a saturated aqueous solution of NaCl and dried over MgSO₄, AcOEt was distilled out. To the residue, were added 2 ml of acetone, 4 ml of EtOH and 10 ml of H₂O. The resultant mixture was adjusted to pH 3 with a 1N aqueous solution of HCl and then left to stand. As a result, solid matter was deposited. The solid matter was recovered by filtration to obtain 82 mg of the intended compound. Physical properties of this compound are described below.
State: Solid.
NMR: δ solvent (DMSO-d⁶).
1.13(3H,d,J=7.0 Hz), 4.11–4.14(1H,m),
4.34(1H,d,J=14.2 Hz), 4.80(1H,d,J=14.2 Hz), 6.16(1H,s),
6.93–6.98(1H,m), 7.18–7.24(1H,m), 7.28–7.33(1H,m),
7.61(1H,s), 8.22(1H,s), 8.45(1H,br-s).
MS: MH⁺=405.

EXAMPLE 139

Preparation of a compound represented by the structural formula:

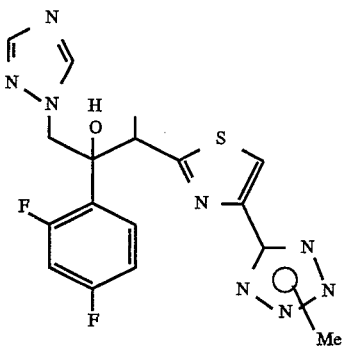

In 1 ml of DMF, were dissolved 80 mg of the compound obtained in Example 138, and 65 mg CsCO₃ were added to the solution, followed by heating for 30 minutes at an external temperature of 60° C. on an oil bath. Further, 0.02 ml of CH₃I was added to the reaction mixture, followed by stirring for 30 minutes at room temperature. The liquid reaction mixture was added with H₂O to subject it to extraction with AdOEt. After the extract was washed with water and then a saturated aqueous solution of NaCl and dried over MgSO₄. AcOEt was distilled cut. The resultant residue was purified by column chromatography (SiO₂:20 g, eluted with CH₂Cl₂, and then with 1% solution of MeOH in CH₂Cl₂ and with 2% solution of MeOH in CH₂Cl₂), thereby obtaining 58 mg of the intended compound. Physical properties of this compound are described below.
State: Solid.
NMR: δ solvent (CDCl₃)
1.22(0.9H,d,J=7.1 Hz), 1.25(2.1H,d,J=7.1 Hz),
4.08–4.21(2H,m), 4.45(0.9H,s), 4.49(2.1H,s),
4.95(0.7H,d,J=14.2 Hz), 5.00(0.3H,d,$J$=14.8 Hz),
5.40(0.7H,s), 5.53(0.3H,s), 6.76–6.84(2H,m),
7.45–7.52(1H,m), 7.72(0.3H,s), 7.75(0.7H,s),
7.78(0.7H,s), 7.81(0.3H,s), 8.14(0.3H,s),
8.35(0.7H,s).
MS: MH⁺=419.

EXAMPLE 140

Preparation of a compound (I) represented by the structural formula:

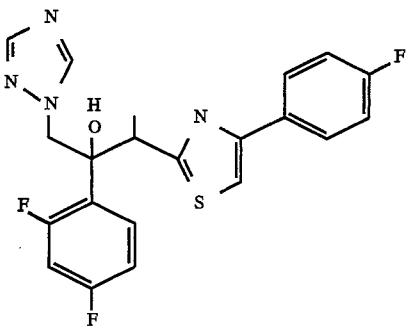

and a diastereomer compound (II) thereof:

The respective intended compounds were obtained in accordance with the same procedure as that described in Example 137 except that 2-ethyl-4-(4'-fluorophenyl)-5-trimethylsilylylthiazole was used in place of 2-ethyl-4-cyano-5-trimethylsilyl-thiazole. Physical properties of these compound are described below.
(I)
mp: 122°–124° C.
NMR: δ solvent (CDCl₃)
1.67(3H,d,J=7.0 Hz), 4.09(1H,q,J=7.0 Hz),
4.73(1H,d,J=13.8 Hz), 4.93 (1H,d,J=13.8 Hz),
6.14(1H,d,J=1.7 Hz), 6.48–6.54(1H,m), 6.66–6.73(1H, m),
7.06–7.12(3H,m), 7.67(1H,s), 7.71–7.74(2H,m),
8.05 (1H, s).
(II)
mp: 87°–89° C.
NMR: δ solvent (CDCl₃)
1.23(3H,d,J=7.1 Hz), 4.06(1H,q,$J$=7.1 Hz),
4.28(1H,d,J=14.4 Hz), 4.89(1H,d,J=14.4 Hz), 6.04(1H,s),
6.77–6.85(2H,m), 7.13–7.17(1H,m), 7.41(1H,s),
7.47–7.55(1H,m), 7.67(1H,s), 7.85–7.92(2H,m),
7.90 (1H,s).

EXAMPLE 141

Preparation of a compound (i) represented by the structural formula:

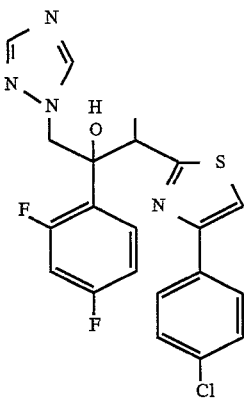

and a diastereomer compound (II) thereof:

The respective intended compounds were obtained in accordance with the same procedure as that described in Example 137 except that 2-ethyl-4-(4'-chlorophenyl)-5-trimethylsilylthiazole was used in place of 2-ethyl-4-cyano-5-trimethylsilylthiazole. Physical properties of these compounds are described below.

(I)
mp: 132°–133° C.
NMR: δ solvent (CDCl$_3$)
1.67(3H,d,J=7.0 Hz), 4.10(1H,q,$J$=7.0 Hz),
4.73 (1H,d,J=13.9 Hz), 4.93 (1H,d,J=13.9 Hz),
6.09(1H,s), 6.46–6.55(2H,m), 7.65–6.73(1H,m),
7.05–7.13(1H,m), 7.17(1H,s), 7.35–7.40(2H,m),
7.65–7.70(2H,m), 8.04(1H,s).

(II)
mp: 162°–164° C.
NMR: δ solvent (CDCl$_3$)
1.23 (3H,d,J=7.1 Hz), 4.06 (1H,q,J=7.1 Hz),
4.27 (1H,d,J=14.4Hz), 4.89(1H,d,J=14.4 Hz), 5.97(1H,s),
6.76–6.85(2H,m), 7.40–7.55(4H,m), 7.67(1H,s),
7.72–7.77 (2H,m), 7.89(1H,s).

EXAMPLE 142

Preparation of a compound represented by the structural formula:

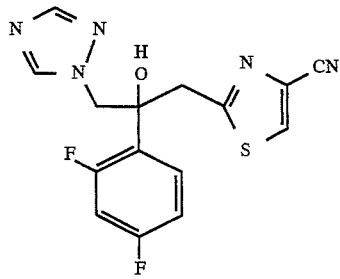

The intended compound was obtained in accordance with the same procedure as that described in Example 137 except that 2-methyl-4-cyano-5-trimethylsilylthiazole was used in place of 2-ethyl-4-cyano-5-trimethylsilylthiazole. Physical properties of this compound are described below.
State: Solid.
NMR: δ solvent (CDCl$_3$)
3.44(1H,d,J=15.0 Hz), 3.81(1H,d,J=15.0 Hz),
4.58(1H,d,J=14.2 Hz), 4.74(1H,d,J=14.2 Hz,
5.48(1H,s), 6.74–6.82(2H,m), 7.40–7.46(1H,m),
7.85(1H,s), 7.87(1H.s), 8.07(1H,s).
MS: MH$^+$=348.

EXAMPLE 143

Preparation of a compound represented by the structural formula:

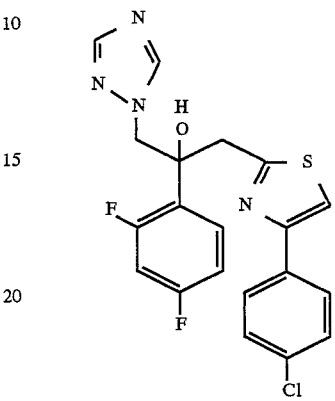

The intended compound was obtained in accordance with the same procedure as that described in Example137 except that 2-methyl-4-(4'-chlorophenyl)-5-trimethylsilylthiazole was used in place of 2-ethyl-4-cyano-5-trimethylsilyl-thiazole. Physical properties of this compound are described below.
State: Solid.
NMR: δ solvent (CDCl$_3$)
3.34(1H,d,J=15.3 Hz), 3.85(1H,d,J=15.3 Hz),
4.62(1H,d,J=14.2 Hz), 4.71(1H,d,J=14.2 Hz),
6.21(1H,s), 6.69–6.83(2H,m), 7.27(1H,s),
7.36–7.46(3H,m), 7.68–7.73(2H,m),
7.85(1H,s), 8.20(1H,s).

EXAMPLE 144

Preparation of a compound represented by the structural formula:

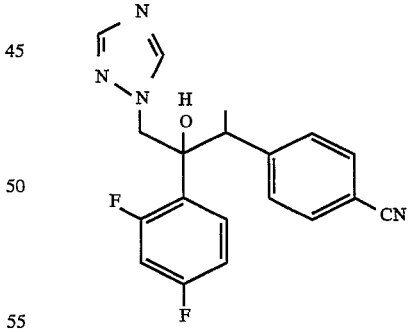

Difluorobenzene (5.77 g) was added to a suspension of AlCl$_3$ (5.88 g) in CH$_2$Cl$_2$ (50 ml), and a solution of 2-(4-cyanophenyl)acetyl chloride (5.28 g) in CH$_2$Cl$_2$ (30 ml) was then added dropwise to the resulting mixture. After the mixture was heated and refluxed for 6 hours, ice water was added thereto. A product extracted from CHCl$_3$ was subjected to column chromatography (SiO$_2$) to conduct elution with CH$_2$Cl$_2$-hexane (1:1), thereby obtaining 4-(2-(2,4-difluorophenyl)-2-oxo)ethylbenzonitrile (2.45 g).

To a solution of this compound in EtOH (12 ml), was added 50% NaOH (0.67 g), and MeI (0.46 ml) was then added dropwise. The resulting mixture was stirred for 4 hours at room temperature. After the mixture was added with ethyl acetate and washed with water, the residue obtained by the evaporation of the organic layer was purified by column chromatography (SiO$_2$; hexane-CH$_2$Cl$_2$=3:1→1:1), thereby obtaining 0.5 g of a compound, 4-(2-(2,4-difluorophenyl)-1-methyl-2-oxo)ethylbenzonitrile.

A 1.0 M ether solution (3.9 ml) of TMSCH$_2$MgCl was chilled to −78°, and an ether solution (5 ml) of the above-described compound (0.5 g) was added dropwise thereto. Thereafter, the mixture was heated to 0° C. and stirred for 10 minutes. A saturated aqueous solution of ammonium chloride was added to the mixture, followed by extraction with AcOEt. The resultant organic layer was evaporated to dryness, and added with CH$_2$Cl$_2$ (10 ml) and BF$_3$-OEt$_2$ (0.24 ml) at 0°, followed by stirring for 1.5 hours at the same temperature. After the mixture was added with AcOEt and washed with an aqueous solution of NaHCO$_3$ and then saturated saline, the solvent was distilled out. The resulting residue was purified by column chromatography (SiO$_2$; hexane-CH$_2$Cl$_2$=3:1 →1:1), thereby obtaining a compound, 4-(2-(2,4-difluorophenyl)-1-methyl-2-propenylbenzonitrile (0.2 g).

Meta-chloroperbenzoic acid (490 mg) was added to a solution of this compound (200 mg) in chloroform (4 ml) while chilling with ice water, and the resultant mixture was left to stand overnight. After the liquid reaction mixture was washed with diluted Na$_2$CO$_3$ and then water, 5 ml of DMF was added to the residue obtained by the evaporation of the resultant organic layer. The thus-obtained mixture was added to a solution of sodium 1,2,4-triazole in DMF (3 ml), which had been prepared from 1,2,4-triazole (272 mg) and 60% NaH (141 mg). After conducting a reaction for 2 hours at 90° C., ethyl acetate was added to the reaction mixture, followed by washing with water. The solvent was distilled out, and the resultant residue was subjected to column chromatography (SiO$_2$; hexane-ethyl acetate=1:1→1:2), thereby obtaining 50 mg of the intended compound. Physical properties of this compound are described below.
mp: 208°–209° C.
NMR: δ solvent (CDCl$_3$)
1.13(3H,t,J=7.1 Hz), 3.38(1H,q,J=7.1 Hz),
3.79(1H,d,J=14.5 Hz), 4.79(1H,d,J=14.5 Hz),
4.98(1H,d,J=8.4 Hz), 6.74–6.81(2H,m),
7.44–7.51(1H,m), 7.64(2H,d,J=8.4 Hz),
7.67(2H,d,J=8.4 Hz), 7.72(1H,s), 7.75(1H,s).

EXAMPLE 145

Preparation of a compound represented by the structural formula A:

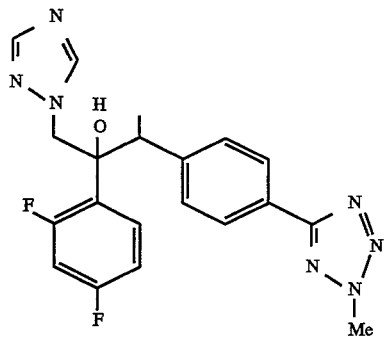

and a compound represented by the structural formula B:

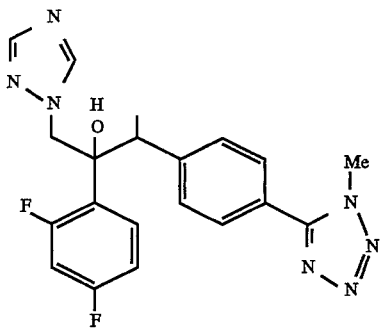

i) The compound (625 mg) obtained in Example 144 was dissolved in N,N-dimethylformamide (2 ml), and the solution was heated together with NaN$_3$ (345 mg) and Et$_3$N·HCl (731 mg) for 7 hours at 100°. After removing insoluble matter by filtration, the solvent was distilled out under reduced pressure, and a small amount of ethanol and water were added to the resulting residue. Thereafter, the resultant mixture was adjusted to pH 2 with HCl. Solid matter deposited was recovered by filtration, washed with water and then dried.

Yield: 539 mg.

ii) The above solid matter (514 mg) was dissolved in N,N-dimethylformamide (5 ml), and Cs$_2$CO$_3$ (422 mg) and MeI (0.089 ml) were added to the solution, followed by stirring for 4 hours at room temperature. Ethyl acetate was added, and the resultant organic layer was washed 3 times with water. Thereafter, the solvent was distilled out, and the residue was purified by column chromatography (SIO$_2$; CH$_2$Cl$_2$→CH$_2$Cl$_2$:EtOAc=4:1), thereby obtaining the compound (333 mg) of the structural formula A and the compound (93 mg) of the structural formula B. physical properties of these compounds are described below.

A mp: 216°–218 ° C.
NMR: δ solvent (CDCl$_3$)
1.17(3H,t,J=7.0 Hz), 3.39 (1H,q,J=7.0 Hz),
3.89 (1H,d,J=14.3 Hz), 4.41(3H,s), 4.83(1H,d,J=14.3 Hz),
4.83 (1H,d,J=1.5 Hz), 6.74–6.81(2H,m),
7.44–7.54(1H,m),
7.64 (2H,d,J=8.4 Hz), 7.71(1H, s), 7.75(1H,s),
8.14 (2H, d,J=8.4 Hz).

B mp: 169°–171° C.
NMR: δ solvent (CDCl$_3$)
1.17(3H,d,J=7.1 Hz), 3.42 (1H,q,J=7.1 Hz),
4.22(3H,s), 4–83(1H,d,J=14.1 Hz),
3.88 (1H,d,J=14.1 Hz), 4.22(3H,s), 4.83(1H,d,J=14.1 Hz),
4.95(1H,d,J=1.5 Hz), 6.75–6.82(2H,m), 7.44–7.55(1H, m),
7.70–7.78 (6H,m).

EXAMPLE 146

Preparation of a compound A represented by the structural formula:

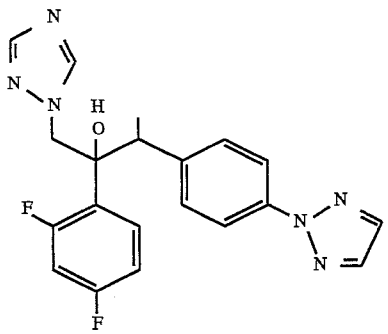

and a diastereomer compound B thereof:

The intended compounds were obtained in accordance with the same procedure as that described in Example 144 except that 2-(4-(1,2,3-triazol-2-yl)phenyl)acetyl chloride was used in place of 2-(4-cyanophenyl)acetyl chloride. Physical properties of these compounds are described below.

A
mp: 198°–199° C.

NMR: δ solvent (CDCl$_3$)
1.16(3H,d,J=7.1 Hz), 3.39(1H,q,J=7.1 Hz), 3.89(1H,d,J=14.1 Hz), 4.83 (1H,d,J=14.1 Hz), 4.85(1H,s), 6.72–6.80(2H,m), 7.44–7.55(1H,m), 7.64(2H,d,J=8.6 Hz), 7.72(1H,s), 7.76(1H,s), 7.83(2H,s), 8.08(2H,d,J=8.6 Hz).

B
State: Solid.
NMR: δ solvent (CDCl$_3$)
1.58(3H,d,J=7.0 Hz), 3.46(1H,q,J=7.0 Hz), 4.67(1H,d,J=13.9 Hz), 4.85(1H,d,J=1.3 Hz), 5.03(1H,d,J=13.9 Hz), 6.42–6.48(1H,m), 6.61–6.67(1H, m), 6.93–6.99(1H,m), 7.14(2H,brd,J=8.6 Hz), 7.75(2H, s), 7.76(1H,s), 7.80(2H,brd,J=8.6 Hz), 7.86(1H,s).

Experimental Example 2:

Five-membered Groups of ICR mice were infected through their tail veins with a Candida albicans MCY8622 strain (2×10$^6$ cfu/mouse). After 1 hour, compounds shown in Table 4 were orally administered in a dose of 2.5 mg or 10 mg per kg of a mouse to the respective groups of mice. Observation was carried out for 7 days to calculate the average number of surviving days in each group. This average number was used as an index indicative of antifungal activity in vivo.

TABLE 4

| Compound | Average number surviving days (days) | |
|---|---|---|
| | 2.5 mg/kg | 10 mg/kg |
| (structure with CN group) | 7.0 | 7.0 |
| (structure with SMe group) | 2.8 | 6.8 |

TABLE 4-continued

| Compound | Average number surviving days (days) | |
|---|---|---|
| | 2.5 mg/kg | 10 mg/kg |
| [structure: triazole-CH2-C(OH)(2,4-F2-C6H3)-CH(CH3)-thiazole-C6H4-SO2Me] | 2.6 | 5.6 |
| [structure: triazole-CH2-C(OH)(2,4-F2-C6H3)-CH(CH3)-thiazole-C6H4-NC2] | 5.8 | 7.0 |
| [structure: triazole-CH2-C(OH)(2,4-F2-C6H3)-CH(CH3)-benzothiazole-CN] | 7.0 | 7.0 |
| [structure: triazole-CH2-C(OH)(2,4-F2-C6H3)-CH(CH3)-benzothiazole-SMe] | 7.0 | 7.0 |

TABLE 4-continued

| Compound | Average number surviving days (days) | |
|---|---|---|
| | 2.5 mg/kg | 10 mg/kg |
| (structure: 2,4-difluorophenyl with triazole, OH, methyl, benzothiazole-SC₂Me) | 7.0 | 6.4 |
| (structure: 2,4-difluorophenyl with triazole, OH, methyl, benzothiazole-tetrazole-N-CH₃) | 6.8 | 7.0 |
| (structure: 2,4-difluorophenyl with triazole, OH, methyl, thiazolopyridine-Cl) | 6.6 | 6.2 |
| (structure: 2,4-difluorophenyl with triazole, OH, methyl, thiazolopyridine-CN) | 6.4 | 6.4 |

TABLE 4-continued

| Compound | Average number surviving days (days) | |
|---|---|---|
| | 2.5 mg/kg | 10 mg/kg |
| 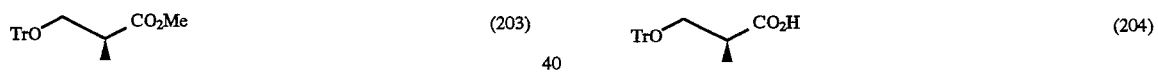 (structure: 2,4-difluorophenyl / 4-cyanophenyl with triazolyl-hydroxy propyl) | 7.0 | 7.0 |
| (structure: 2,4-difluorophenyl / 4-(N-methyltetrazolyl)phenyl with triazolyl-hydroxy propyl) | 6.8 | 7.0 |

EXAMPLE 147

TrO–CH₂–CH(CO₂Me)–  (203)

In 33 ml of pyridine, were dissolved 6.6 ml (60 mmol) of (S)-methyl hydroxy-2-methylpropionate. To the resultant solution, were added 18.1 g (1.5 equivalents) of triphenylchloromethane, followed by heating for 1 hour at 80° C. The reaction mixture was cooled to room temperature and then added little by little into 350 ml of water. Crystals deposited were collected by filtration, washed with water and dried. The thus-obtained product was recrystallized from ethanol to obtain 18.3 g (yield: 85%) of the intended compound (203).

$C_{24}H_{24}O_3$ MH⁺ = 360

| | H | C | N |
|---|---|---|---|
| Calculated % | 6.71 | 79.97 | 0 |
| Found % | 6.76 | 79.77 | 0.05 |

Crystal melting point: 84°–85° C.
¹H-NMR (δ, CDCl₃):
1.15(3H,d;J=7.1 Hz), 2.69–2.77(1H,m), 3.17(1H,dd;J=5.6 Hz, 8.8 Hz), 3.29(1H,dd;J=5.6 Hz,8.8 Hz),
3.70(3H,s), 7.20–7.44(15H,m).

TrO–CH₂–CH(CO₂H)–  (204)

In a liquid mixture of 108 ml of tetrahydrofuran and 54 ml of methanol, were dissolved 10.8 g (30.0 mmol) of the compound (203). While chilling with ice water, 54 ml of an aqueous solution of 2.52 g (2 equivalents) of lithium hydroxide monohydrate were added dropwise to the resultant solution over 15 minutes with stirring. After the resulting mixture was heated to room temperature and stirred for 4 hours, 3.6 ml of glacial acetic acid were added, and the organic solvent was distilled out under reduced pressure. After the residue was subjected to extraction with ethyl acetate, the extract was washed with water, dried and concentrated to obtain 10.4 g of the intended compound (204). A sample for (quantitative) analysis was obtained by recrystallization from dichloromethane-hexane.

$C_{23}H_{22}O_3$ MH⁺ = 347

| | C | H | N |
|---|---|---|---|
| Calculated % | 79.74 | 6.47 | 0 |
| Found % | 79.59 | 6.47 | 0.07 |

Crystal melting point: 99°–102° C.
¹H-NMR (δ, CDCl₃):
1.18(3H,d;J=7.2 Hz), 2.69–2.78(1H,m), 3.25(1H,dd;J=5.6 Hz,8.8 Hz), 3.32(1H,dd;J=5.6 Hz,8.8 Hz), 7.15–7.45(15H,m).

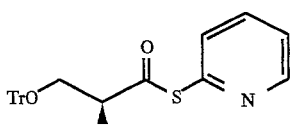
(205)

In 50 ml of dichloromethane, were dissolved 10.3 g (29.8 mmol) of the compound (204). While chilling with ice water, 3.64 g (1.1 equivalents) of 2-mercaptopyridine, 3.64 g (0.1 equivalent) of 4-dimethylaminopyridine and 6.76 g (1.1 equivalents) of dicyclohexylcarbodiimide were successively added to the resultant solution. After the resulting mixture was stirred for 3.5 hours while chilling with ice water and for 2 hours at room temperature, the precipitate formed was separated by filtration. After the filtrate was diluted with ethyl acetate, it was washed twice with water and with saturated saline and dried over magnesium sulfate, and the solvent was distilled out under reduced pressure.

The residue was purified through a silica gel column (eluted with hexane:ethyl acetate=9:1), thereby obtaining 11.9 g (yield: 91%) of the intended compound (205) in the form of a yellow oil.

$^1$H-NMR ($\delta$, CDCl$_3$):
1.21(3H,d;J=7.2 Hz), 2.99–3.09(1H,m),
3.21(1H,dd;J=5.6 Hz,9.2 Hz), 3.44(1H,dd;J=7.6 Hz,9.2 Hz),
7.21–7.33(10H,m), 7.43–7.47(6H,m), 7.63(1H,d;J=8.0 Hz),
7.73(1H,t;J=8.0 Hz), 8.63(1H,d;J=4.8 Hz).

EXAMPLE 148

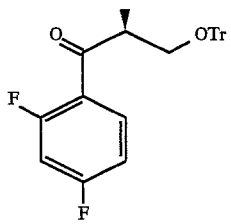
(206)

In 7.8 ml of tetrahydrofuran, were suspended 780 mg [1.2 equivalents to the compound (205)] of magnesium powder activated by stirring overnight at 120° C. in a nitrogen stream. One drop of 2,4-difluorobromobenzene and one piece of iodine crystal were added to this suspension to stir the resulting mixture, to which a solution with 3.67 ml [1.2 equivalents to the compound (205)] of 2,4-difluorobromobenzene dissolved in 17 ml of tetrahydrofuran was added dropwise while maintaining the internal temperature at 40° to 60° C. After 20 ml of tetrahydrofuran were added, the resulting mixture was chilled to the internal temperature of −30° C. A solution with 11.9 g (27.1 mmol) of the compound (205) dissolved in 90 ml of tetrahydrofuran was added dropwise to the mixture while maintaining the internal temperature at −25° to −30° C. After the resulting mixture was stirred for 15 minutes at −30° C. and for 2 hours at room temperature, a saturated aqueous solution of ammonium chloride was added to the reaction mixture, followed by stirring for 15 minutes. Ethyl acetate and water were added to the mixture to recover an organic layer. The organic layer was washed twice with water and once with saturated saline and then dried over anhydrous magnesium sulfate, and the solvent was distilled out under reduced pressure. The residue was purified through a silica gel column (eluted with hexane:ethyl acetate=9:1) and further recrystallized from methanol, thereby obtaining 7.46 g (yield: 62%) of the intended compound (206).

| $C_{29}H_{24}F_2O_2$, MH$^+$ = 442 | | | |
|---|---|---|---|
| | H | C | N |
| Calculated % | 5.47 | 78.7 | 0 |
| Found % | 5.48 | 78.73 | 0 |

Crystal melting point: 94°–97° C.
$^1$H-NMR ($\delta$, CDCl$_3$):
1.21(3H,d;J=6.8 Hz), 3.21(1H,dd;J=5.2 Hz,8.8 Hz),
3.42(1H,dd;J=6.4 Hz,8.8 Hz), 3.56(1H,m), 6.80(1H,m),
6.94(1H,m), 7.17–7.31(15H,m), 7.77–7.83(6H,m).

EXAMPLE 149

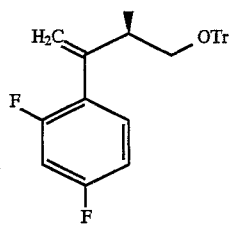
(207)

In 64 ml of tetrahydrofuran, were suspended 6.43 g [1.2 equivalents to the compound (206)] of methyltriphenylphosphonium bromide in a nitrogen stream. To this suspension, 11.2 ml [1.2 equivalents to the compound (206)] of butyllithium (1.6 mol hexane solution) were added dropwise while chilling with ice water. After the resultant mixture was heated back to room temperature and then stirred for 2 hours, a solution of 6.63 g (15.0 mmol) of the compound (206) in 30 ml of tetrahydrofuran was added dropwise, followed by stirring for 30 minutes. To the liquid reaction mixture, 500 ml of hexane and 300 ml of water were added, and insoluble matter was removed by filtration.

An organic layer was recovered and washed 3 times with water and once with saturated saline and dried over anhydrous magnesium sulfate, and the solvent was then distilled out under reduced pressure. The residue was purified through a silica gel column (eluted with hexane:ethyl acetate=50:1), thereby obtaining 5.4 g (yield: 85%) of an oily product (207).

$^1$H-NMR ($\delta$, CDCl$_3$):
1.16(3H,d;J=7.0 Hz), 2.81–2.89(1H,m),
2.97–3.01(1H,dd;J=6.0 Hz,9.2 Hz),
3.04–3.08(1H,dd;J=6.0 Hz,9.2 Hz), 5.11(1H,S),
6.68–6.75(2H,m), 7.00–7.06(1H,m), 7.18–7.28(9H,m),
7.35–7.39 (6H,m).

EXAMPLE 150

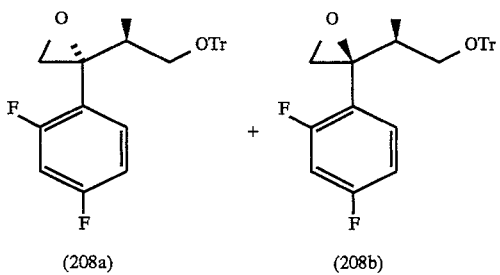

(208a)      (208b)

In 25 ml of dichloromethane, were dissolved 2.70 g (6.14 mmol) of the compound (207). While chilling with ice waters, 1.46 g (1.1 equivalent) of meta-chloroperbenzoic acid (purity: 80%) were added to the solution, followed by stirring for 12 hours at 4° C. Meta-chloroperbenzoic acid in an amount of 290 mg (0.34 equivalent) was added to the reaction mixture, followed by stirring further for 5 hours at room temperature. A 10% aqueous solution of sodium hydrogensulfite was added to the mixture, followed by extraction with ethyl acetate. The resultant organic layer was washed successively with water, a saturated aqueous solution of sodium hydrogencarbonate, water and saturated saline, and then dried over magnesium sulfate, and the solvent was distilled cut under reduced pressure, thereby obtaining 2.813 g of an oily compound (208). As a result of proton NMR analysis, it was found that this compound was a 2:1 mixture of the desired isomer (208a) and its diastereomer (208b).

$^1$H-NMR (δ, CDCl$_3$):

0.93(3H,d;J=8.8 Hz)<a>, 0.98 (3H,d;J=8.8 Hz)<b>, 2.04–2.12(1H,m)<b>, 2.20–2.28(1H,m)<a>, 2.76(1H,d;J=5.2 Hz)<a>, 2.76(1H,d;J=5.2 Hz)<b>, 2.88(1H,dd;J=7.2 Hz,9.2 Hz)<a>, 2.96(1H,dd;J=7.2 Hz,9.2 Hz)<b>, 3.00–3.06(1H,m)<a+b>, 3.02(1H,d;J=5.2 Hz)<a>, 3.11(1H,d;J=5.2 Hz)<b>, 6.61–6.73(2H,m)<a+b>, 7.12–7.50(16H,m)<a+b>.

EXAMPLE 151

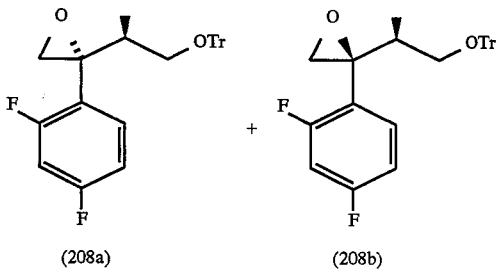

(208a)    (208b)

<Alternative process>

A 1.6 M hexane solution of butyllithium was added dropwise to a solution of 221 mg of the compound (206) and 44 μl (1.2 equivalents) of chloroiodomethane in tetrahydrofuran (2.2 ml) at −70° C. while being purged with nitrogen. The resultant mixture was stirred for 5 minutes at this temperature and then heated until its internal temperature reached room temperature to stir for 1 hour. An aqueous solution of ammonium chloride and ethyl acetate were successively added to the mixture to separate liquids. The resulting organic layer was washed with water and with saturated saline and dried over magnesium sulfate, and the solvent was distilled out under reduced pressure. The residue was purified through a silica gel column (eluted with hexane:ethyl acetate=9:1), thereby obtaining 219 mg (yield: 96%) of a compound (208). As a result of proton NMR analysis, it was found that this compound was a diastereomeric mixture containing the compounds (208a) and (208b) in a ratio of 1:2.5.

EXAMPLE 152

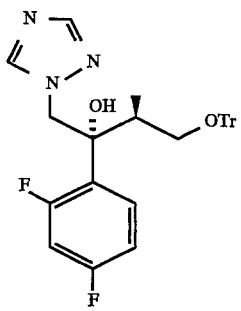

(209a)

In 8.5 ml of dimethylformamide, were suspended 370 mg [1.5 equivalents to the compound (208)] of sodium hydride (60% dispersion in mineral oil), and 851 mg [2 equivalents to the compound (208)] of 1,2,4-triazole were added to the suspension. After stirring for 15 minutes at room temperature, a solution with 2.813 g (6.17 mmol) of the compound (208) (diastereomeric mixture of <a>:<b>=2:1) dissolved in 22 ml of dimethylformamide was added to the suspension, and the resulting mixture was stirred for 7.5 hours at 80° C. After cooling to room temperature, water and ethyl acetate were added to the mixture to separate liquids. The resultant organic layer was washed with saline and then dried over magnesium sulfate, and the solvent was distilled out under reduced pressure. The residue was purified through a silica gel column (eluted with dichloromethane:methanol =200:1), thereby separately obtaining 860 mg of the intended compound (209a), 99 mg of its diastereomer (209b) having high polarity and 867 mg of a mixture of both compounds as white solids.

$^1$H-NMR (δ, CDCl$_3$):

0.87(3H,d;J=7.6 Hz), 2.37–2.45(1H,m), 3.40(1H,dd;J=3.2 Hz,10.0 Hz), 3.55(1H,dd;J=5.6 Hz,10.0 Hz), 4.19(1H,d;J=14.4 Hz), 4.65(1H,d;J=14.4 Hz), 4.88(1H,s), 6.64–6.72(2H,m), 7.22–7.30(6H,m), 7.32–7.37(6H,m), 7.46–7.50(6H,m), 7.64(1H,S), 7.84 (1H,s).

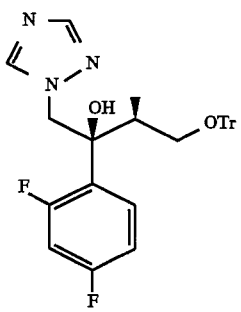

(209b)

See the description of the compound (209a). Solid
$^1$H-NMR (δ, CDCl$_3$):

1.48(3H,d;J=7.6 Hz), 2.47–2.56(1H,m), 2.92(1H,dd;J=3.2 Hz,9.6 Hz), 3.19(1H,dd;J=3.2 Hz, 9.6 Hz), 4.56(1H,d;J=14.0 Hz), 4.69(1H,d;J=14.0 Hz), 4.78(1H,s), 6.49–6.61(2H,m), 7.01–7.09(1H,m), 7.16–7.37(15H,m), 7.63(1H,s), 7.88(1H,s).

EXAMPLE 153

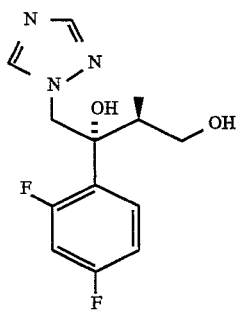

(210)

In 7.4 ml of methanol, were dissolved 740 mg (1.41 mmol) of the compound (209a), and 295 mg (1.1 equivalents) of toluenesulfonic acid monohydrate were added to the resulting solution, followed by stirring for 1 hour at room temperature. To the resulting mixture, 295 mg (1.1 equivalent) of toluenesulfonic acid monohydrate were added, followed by stirring further for 3 hours at room temperature. An aqueous saturated solution of sodium hydrogen-carbonate and ethyl acetate were added to the mixture to separate liquids. The resulting organic layer was washed with water and then with saturated saline and dried over magnesium sulfate, and the solvent was distilled out under reduced pressure. The residue was purified through a silica gel column (eluted successively with mixtures of dichloromethane and methanol in ratios of 100:1, 50:1 and 25:1), thereby obtaining 246 mg of a crude product. The product was recrystallized from a mixed solvent of dichloromethane and isopropyl ether to obtain 190 mg (yield: 48%) of the intended compound (210) as a pure product.

| $C_{13}H_{14}F_2N_3O_2$, $MH^+$ = 284 | | | |
|---|---|---|---|
| | H | C | N |
| Calculated % | 5.34 | 55.12 | 14.83 |
| Found % | 5.33 | 55.09 | 14.93 |

Melting point: 134°–135° C.
$^1$H-NMR (δ, CDCl$_3$):
0.84(3H,d,J=7.2 Hz), 2.30–2.39(1H,m),
2.67–2.77(1H,br, s), 3.83 (1H,dd;J=5.4 Hz11.2 Hz),
3.99(1H,dd;J=3.2 Hz, 11.2 Hz), 4.76(1H,d,J=14.0 Hz),
4.97(1H,d,J=14.0 Hz), 5.28(1H,s), 6.69–6.78(2H,m),
7.36–7.43(1H,m), 7.75(1H,s), 7.91(1H,s).

EXAMPLE 154

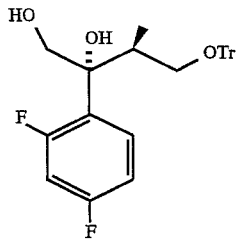

(211a)

In a mixed solution of 5 ml of water and 2.5 ml of acetone, were dissolved 144 mg of N-methylmorpholine oxide (50% aqueous solution), and 36 μl of osmium tetroxide (4% aqueous solution) and an solution of 247 mg of the compound (207) in 2.54 ml of acetone were added successively to the resulting solution. After stirring overnight at room temperature, 100 μl of osmium tetroxide (4% aqueous solution) were added to the mixture, followed by stirring further for 24 hours at room temperature. To the mixture, was added a 10% aqueous solution of sodium hydrogensulfite, followed by extraction with ethyl acetate. The resultant organic layer was washed with saline and dried over magnesium sulfate, and the solvent was then distilled out under reduced pressure. The residue was purified through a silica gel column (eluted successively with mixtures of hexane and ethyl acetate in ratios of 10:1 and 4:1), thereby obtaining 153 mg of a main product (211a) in a solid form and 23 mg of its diastereomer (211b) having high polarity.

$^1$H-NMR (δ, CDCl$_3$):
0.75(3H,d;J=8.8 Hz), 1.80(1H,dd;J=5.2 Hz,8.4 Hz),
2.44–2.53(1H,m), 2.77(1H,dd;J=5.6 Hz, 8.4 Hz),
3.21 (1H,dd;J=8.4 Hz,14.0 Hz),
3.32 ( 1H, dd ;J=2.8 Hz, 14.0 Hz ),
3.63 (1H,dd;J=8.4 Hz, 11.2 Hz),
3.96(1H,ddd;2.8 Hz,5.6 Hz,11.2 Hz), 4.39(1H,s),
6.69–6.76(1H,m), 6.79–6.84(1H,m), 7.22–7.30(3H,m),
7.32–7.37(6H,m), 7.43–7.47(6H,m), 7.52–7.58 (1H,m).

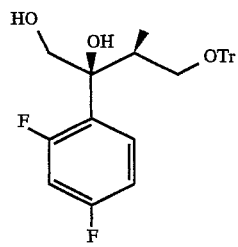

(211b)

See the description of the compound (211a). Solid.
$^1$H-NMR (δ, CDCl$_3$):
1.35(3H,d;J=7.2 Hz), 2.34–2.44(1H,m),
2.93 (1H,dd;J=3.6 Hz,9.6 Hz), 3.19(1H,dd;J=3.6 Hz,9.6 Hz),
3.82 (1H,dd;J=6.8 Hz, 10.6 Hz),
3.96(1H,dd;J=5.2 Hz,10.6 Hz), 4.50(1H,s),
6.57–6.64(1H,m), 6.70–6.75(1H,m), 7.18–7.31(15H,m),
7.39–7.45(1H,m).

EXAMPLE 155

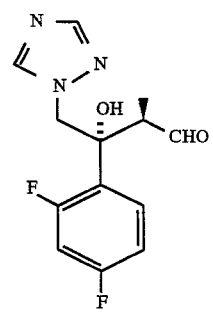

(212)

In 3.3 ml of dichloromethane, were dissolved 96 μl (2.2 equivalents to the substrate) of oxalyl chloride, and a solution of 185 μl (4.8 equivalents to the substrate) of dimethyl sulfoxide in dichloromethane (0.9 ml) was added dropwise to the resulting solution at –60° C. in a nitrogen stream. After stirring for 5 minutes, a solution of 142 mg (0.500 mmol) of the compound (210a) in dichloromethane (4.2 ml) was added dropwise. After stirring for 30 minutes, 350 μl (5 equivalents to the substrate) of triethylamine were added. The resultant mixture was heated to room temperature. Water was added to the mixture, followed by extraction twice with dichloromethane. The resulting organic layer was washed twice with water and once with saturated saline and dried over magnesium sulfate, and the solvent was then distilled out under reduced pressure. The residue was purified through a silica gel column (eluted with dichloromethane:methanol=50:1), thereby obtaining 106 mg (yield: 75%) of the intended product (212).

| $C_{13}H_{13}F_2N_3O_2$ MH⁺ = 262 | | | |
|---|---|---|---|
| | H | C | N |
| Calculated % | 4.66 | 55.52 | 14.94 |
| Found % | 4.68 | 55.44 | 14.96 |

Melting point: 140°–144° C.
¹H-NMR (δ, CDCl₃):
1.01(3H,d;J=7.2 Hz), 2.96–3.03(1H,m),
4.62(1H,d;J=14.0 Hz), 4.90(1H,d,J=14.0 Hz), 5.16(1H, s),
6.73–6.81(2H,m), 7.37–7.44(1H,m), 7.79(1H,s),
7.86(1H,s), 9.85(1H,d;J=3.2 Hz).

EXAMPLE 156

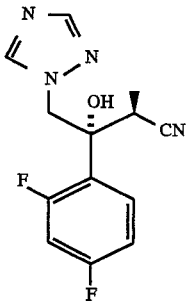
(202)

In 0.36 ml of water, were suspended 36 mg (0.128 mmol) of the compound (212), and 17 mg (1.2 equivalents) of hydroxylaminesulfonic acid were added to the suspension, followed by heating for 1.5 hours at 50° C. To the resultant mixture, 21 mg of hydroxylaminesulfonic acid were added, followed by heating further for 40 minutes. Ethyl acetate and an aqueous solution of sodium hydrogencarbonate were added to the liquid reaction mixture to separate liquids. The resultant organic layer was washed with water and with saturated saline and dried over magnesium sulfate, and the solvent was then distilled out under reduced pressure. The residue was purified through a silica gel column (eluted with dichloromethane:methanol=100:1), thereby obtaining 2 mg of the intended product (202).

$C_{13}H_{12}F_2N_4O_1$ MH⁺=279
Melting point: 181°–182° C.
¹H-NMR (δ, CDCl₃):
1.17(3H,d;J=7.2 Hz), 3.29(1H,q;J=7.2 Hz),
4.82(1H,d;J=14.0 Hz), 4.97(1H,d;J=14.0 Hz),
5.44(1H,d;J=0.8 Hz), 6.74–6.82(2H,m), 7.39–7.46(1H, m),
7.83(1H,s), 7.84(1H,s).

EXAMPLE 157

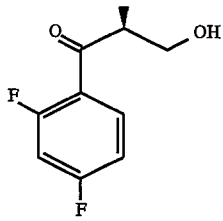
(213)

In 1.1 ml of methanol, were dissolved 110 mg of the compound (206), and 53 mg (1.1 equivalents) of p-toluenesulfonic acid monohydrate was added to the solution, followed by stirring for 20 minutes at 40° C. Water and ethyl acetate were added to the mixture to subject it to extraction. The resultant organic layer was washed with saturated saline and dried over magnesium sulfate, and the solvent was then distilled out under reduced pressure. The residue was purified through a silica gel column to obtain 32 mg (yield: 58%) of the intended compound (213) in an oily form. An optical purity of this compound was measured by high-performance liquid chromatography making use of a chiral column. The optical purity was 90.0% ee. The conditions for the analysis are described below.

Column: Chiral Cell OB (internal diameter: 4 mm, length: 250 mm)

Mobile phase: Hexane:isopropanol=9:1

Flow rate: 0.5 ml/min
¹H-NMR (δ, CDCl₃):
1.18(3H,d;J=6.8 Hz), 2.50(1H,t;J=6.0 Hz),
3.45–3.54(1H,m), 3.72–3.79(1H,m), 3.84–3.92(1H,m),
6.82–6.88(1H,m), 6.92–6.98(1H,m), 7.83–7.90(1H,m).

EXAMPLE 158

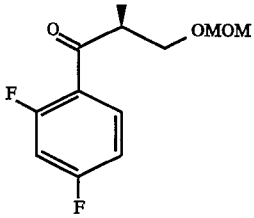
(214)

In 5 ml of dichloramethane, were dissolved 472 mg (2.36 mmol) of the compound (213), and 448 µl (2.5 equivalents) of chloromethyl methyl ether, 822 µl (2 equivalents) of diethylisopropylamine and a catalytic amount of 4-dimethylaminopyridine were added to the solution, followed by overnight stirring at room temperature. Dichloromethane and water were added to the mixture to subject it to extraction. The resultant organic layer was washed with water and with saturated saline and dried over magnesium sulfate, and the solvent was then distilled out under reduced pressure. The residue was purified through a silica gel column (eluted with hexane:ethyl acetate=10:1), thereby obtaining 485 mg (yield: 84%) of the intended product (214) as an oily product.

¹H-NMR (δ, CDCl₃):
1.22(3H,d;J=6.8 Hz), 3.29(3H,s), 3.85–3.68 (2H,m),
3.87–3.94(1H,m), 4.56(1H,d;J=8.4 Hz),
4.59(1H,d;J=8.4 Hz), 6.84–6.91(1H,m), 6.94–6.99(1H, m),
7.85–7.92 (1H,m).

EXAMPLE 159

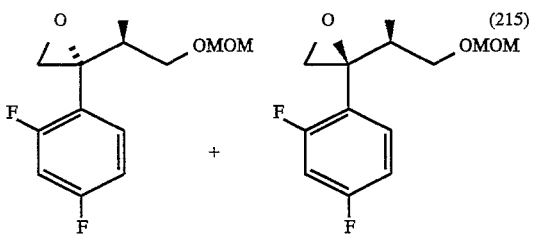

The intended compound (215) in an oily form was obtained as a 1:1 diastereomeric mixture in accordance with the alternative process for the synthesis of the compound (208).

$^1$H-NMR ($\delta$, CDCl$_3$):

0.99(3H,d;J=6.8 Hz)<a>, 1.20(3H,d;J=6.8 Hz)<b>, 2.08–2.22 (1H,m)<a+b>, 2.78 (1H,d;J=5–2 Hz)<a+b>, 3.09(1H,d;J=5.2 Hz), 3.33(1H,s)<a>, 3.36(1H,s)<b>, 3.19–3.38(1H,m)<a+b>, 3.45–3.54(1H,m)<a+b>, 4.57(2H,s)<a>, 4.61(1H,s)<b>, 6.75–6.88(2H,m)<a+b>, 7.32–7.45 (1H,m) <a+b>.

EXAMPLE 160

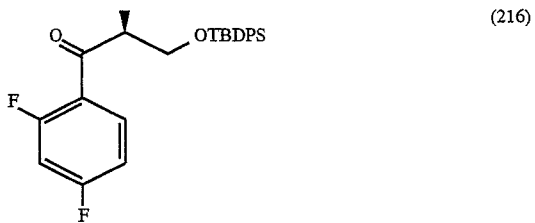

In 2.5 ml of dimethylformamide, were dissolved in 500 mg of the compound (213), and 715 mg of imidazole and 715 μl of t-butyldiphenylsilyl chloride were successively added to the solution, followed by stirring for 2.5 hours at room temperature. Ethyl acetate and water were added to the reaction mixture to separate liquids. The resultant organic layer was washed with water and with saturated saline and dried over magnesium sulfate. The product was purified through a silica gel column (eluted with hexane:ethyl acetate=9:1), thereby obtaining 939 mg of the intended product (216) in a solid form.

$^1$H-NMR ($\delta$, CDCl$_3$):

0.94(9H,s), 1.19(3H,d;J=10.0 Hz), 3.58(1H,m), 3.75(1H,ddd;J=10.0 Hz,5.2 Hz, 0.8 Hz), 3.94(1H,ddd;J=10.0 Hz,6.8 Hz, 1.6 Hz), 6.82–6.87(1H, m), 6.92–6.98(1H,m), 7.29–7.44(6H,m), 7.49–7.52(2H,m), 7.57–7.61(2H,m), 7.79–7.85(1H,m).

EXAMPLE 161

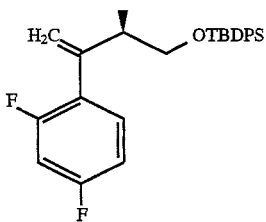

A solution of 438 mg (1.00 mmol) of the compound (216) in 4.4 ml of diethyl ether was added dropwise to 3.0 ml of a 1.0 M diethyl ether solution of trimethylmagnesium chloride at room temperature in a nitrogen stream, followed by stirring for 2.5 hours at room temperature. After an aqueous solution of ammonium chloride was added to the resultant mixture, it was subjected to extraction with ethyl acetate. The extract was washed with water and with saturated saline and then dried over magnesium sulfate. Azeotropic distillation with toluene gave 524 mg of a solid product.

The product in an amount of 262 mg was dissolved in 2.5 ml of dichloromethane, and 69 μl of a boron trifluoride-diethyl ether complex were added dropwise to the solution while chilling with ice water. After stirring for 10 minutes, an aqueous solution of sodium hydrogencarbonate was added to the reaction mixture, followed by extraction with dichloromethane. The extract was washed with water and with saturated saline and dried over magnesium sulfate, and the solvent was then distilled out under reduced pressure. The residue was purified through a silica gel column (eluted with hexane:ethyl acetate=20:1), thereby obtaining 174 mg of the intended product (217) as an oily product.

$^1$H-NMR ($\delta$, CDCl$_3$):

1.02(9H,s), 1.17(3H,d;J=6.8 Hz), 2.72–2.80(1H,m), 3.50(1H,dd;J=6.4 Hz, 10.0 Hz), 3.64(1H,dd;J=5.2 Hz,10.0 Hz), 5.13(1H,s), 5.23(1H,s), 6.71–6.78(2H,m), 7.04–7.11(1H,m), 7.31–7.43(6H,m), 7.58–7.63 (4H,m).

EXAMPLE 162

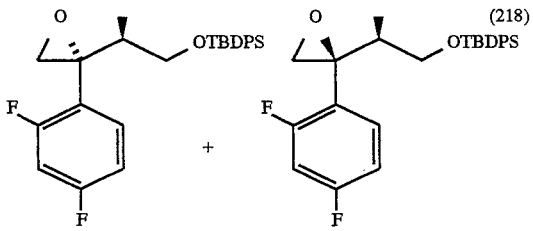

The process for the synthesis of the compound (208) was followed. As a result of proton NMR analysis, the diastereomeric ratio of an oily product (218) was found to be 1:2.

$^1$H-NMR ($\delta$, CDCl$_3$):

0.92 (3H,d;J=8.8 Hz) <a>, 0.97 (3H,d;J=8.8 Hz) <b>, 1.03(9H,s)<b>, 1.06(9H,s)<a>, 1.96–2.05(1H,m<b>, 2.14 –2.22 (1H, m)<a>, 2.78(1H, d; J=5.2 Hz) <b>, 2.79 (1H,d;J=5.2 Hz) <a>, 3.08 (1H,d;J=5.2 Hz) <b>, 3.17 (1H,d;J=5.2 Hz) <a>, 3.45–3.66 (2H,m) <a+b>, 6.70–6.82 (2H,m) <a+b>, 7.30–7.45(6H,m) <a+b>, 7.59–7.68 (4H,m) <a+b>.

EXAMPLE 163

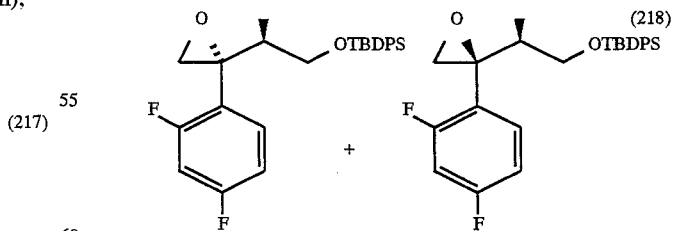

<Alternative process>

In 2 ml of tetrahydrofuran, were dissolved 72 mg (0.16 mmol) of the compound (216) and 3.2 μl (0.18 mmol) of chloroiodomethane. The resultant solution was chilled to −78° C. in a nitrogen stream. To this solution, 0.12 ml (0.17 mmol) of a 1.5 M diethyl ether solution of a methyllithium-lithium bromide complex was added dropwise. The resulting mixture was stirred for 1 hour while heating it to room temperature. A saturated aqueous solution of ammonium chloride was added to the reaction mixture, followed by extraction with ethyl acetate. The resultant organic layer was washed with saturated saline, dried and then concentrated under reduced pressure, thereby obtaining 86 mg of an oily compound (218). As a result of proton NMR analysis, the diastereomeric ratio of the product was found to be 1:1.

EXAMPLE 164

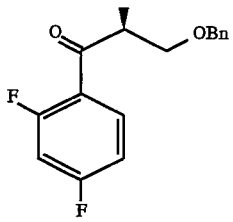
(219)

The compound (213) (223 mg; 0.507 mmol) was dissolved in 5.0 ml of toluene, and 141 mg (0.609 mmol) of silver oxide and 84 μl (0.710 mmol) of benzyl bromide were added to the solution, followed by stirring for 7 days at room temperature. The reaction mixture was filtered through Celite, and the resultant filtrate was washed with ether. The filtrate was concentrated and then purified by column chromatography on silica gel (eluted with hexane and then hexane:ethyl acetate=12:1), thereby obtaining 66 mg (yield: 44%) of a compound (219) as a colorless oily product.
$^1$H-NMR (δ, CDCl$_3$):
  1.21(3H,d;J=7.0 Hz), 3.54(1H,dd;J=8.8 Hz,5.5 Hz), 3.60–3.70(1H,m), 3.82(1H,dd;J=8.8,3.6 Hz), 4.47(1H,d;J=11.9 Hz), 4.54(1H,d;J=11.9 Hz), 6.80–6.98(2H,m), 7.20–7.40(5H,m), 7.82–7.88(1H,m).

EXAMPLE 165

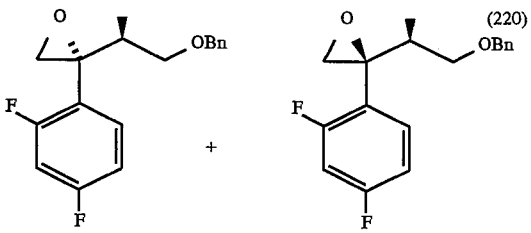
(220)

In 2ml of anhydrous tetrahydrofuran, were dissolved 66 mg (0.23 mmol) of the compound (219) and 18 μl (0.25 mmol) of chloroiodomethane. The resultant solution was chilled to –78° C. To this solution, 0.16 ml (0.24 mmol) of a 1.5 M diethyl ether solution of a methyllithium-lithium bromide complex was added dropwise. The resulting mixture was then heated to room temperature and stirred for 2.5 hours. A saturated aqueous solution of ammonium chloride was added to the reaction mixture, followed by extraction with ethyl acetate. The resultant organic layer was washed with saturated saline, dried over anhydrous magnesium sulfate and then concentrated under reduced pressure, thereby obtaining 60 mg (yield: 86%) of a compound (220) as an oily product.

Incidentally, the compound (220) is a 1:1 mixture of diastereomers.
$^1$H-NMR (δ, CDCl$_3$):
  0.97(3H,d;J=7.2 Hz)<a>, 1.01(3H,d;J=7.5 Hz)<b>, 2.14–2.18(1H,m)<a>, 2.20–2.28(1H,m)<b>, 2.77–2.80(2H,m)<a+b>, 3.07–3.10(2H,m)<a+b>, 3.24–3.32(2H,m)<a+b>, 3.38–3.46(2H,m)<a+b>, 4.40–4.52(4H,m)<a+b>, 6.75–6.84(4H,m)<a+b>, 7.26–7.40 (12H,m) <a+b>.

Preparation Examples
Preparation examples from the compound (202) to a final compound will hereinafter be described.
Preparation Example 8

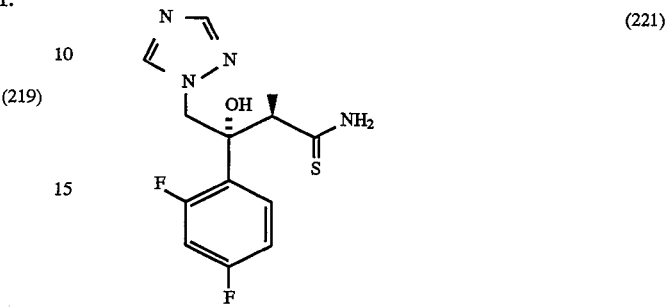
(221)

To 33 g of the compound (202), 33 ml of H$_2$O and 172 ml of 0,0-diethyl dithiophosphate were added, and the mixture was heated and refluxed for 30 minutes. The reaction mixture was cooled back to room temperature and added with water, followed by extraction with ethyl acetate. The resultant ethyl acetate layer was washed with water and with saturated saline and dried over magnesium sulfate, and the solvent was distilled out. To the resulting residue, 70 ml of diethyl ether were added to form crystals. The thus-formed crystals were collected by filtration to obtain the intended compound (35 g) as a crude product. The crude product (13.9 g) was dissolved in ethyl acetate, and the solution was washed with a 5% aqueous solution of sodium carbonate, and the solvent was then distilled cut. The resultant residue was recrystallized from diethyl ether and diisopropyl ether, thereby obtaining 7.8 g of the intended compound (221).
MH$^+$=313
Melting point: 132°–134° C.
$^1$H-NMR (δ, CDCl$_3$):
  1.11(3H,d;J=7.1 Hz), 3.71(1H,q;J=7.1 Hz), 4.55(1H,d;J=14.3 Hz), 5.08(1H,d;J=14.3 Hz), 6.71–6.80(2H,m), 7.42–7.48(1H,m), 7.80(1H,brs), 7.94(1H, s), 8.41(1H,brs).

Preparation Example 9

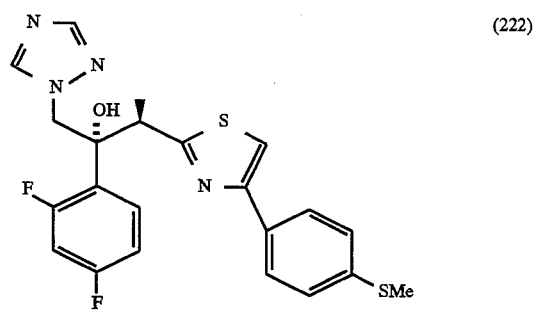
(222)

The compound (221) (15.02 g) was dissolved in ethanol (150 ml), and 2-bromo-4'-methylthioacetophenone (14.97 mg) was added, followed by heating and refluxing for 4 hours. The liquid reaction mixture was chilled to 0° C. and then neutralized with an aqueous solution of sodium hydrogen-carbonate, followed by extraction with ethyl acetate. The extract was washed with water and then with saturated saline and dried over magnesium sulfate, and ethyl acetate was distilled out. The residue was purified by chromatography on silica gel (SiO$_2$, eluted with dichloromethane and then with a solution of 1% methanol in dichloromethane), thereby obtaining the intended compound (222) (10.19 g) as a solid product.

MH⁺=459

¹H-NMR (δ, CDCl₃):

1.23(3H,d;J=7.2 Hz), 2.54(3H,s), 4.05(1H,q;J=7.2 Hz), 4.28(1H,d;J=14.4 Hz), 4.88(1H,d;J=14.4 Hz), 6.13(1H,s), 6.75–6.85(2H,m), 7.33(2H,br-d:J=8.4 Hz), 7.42(1H,s), 7.46–7.54(1H,m), 7.66(1H,s), 7.82(2H,br-d:J=8.4 Hz), 7.92 ( 1H, s).

Preparation Example 10

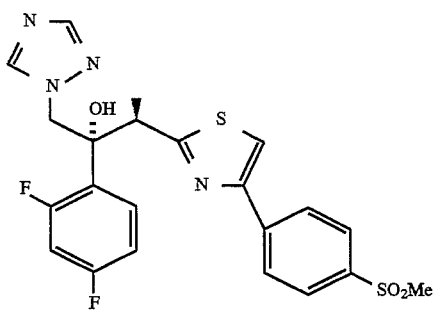
(223)

To a solution with the compound (222) (10.19 g) dissolved in 150 ml of chloroform, 18.35 g of metachloroperbenzoic acid were added, followed by stirring at room temperature. After the raw material disappeared, water was added to the liquid reaction mixture, followed by extraction with chloroform. The resultant organic layer was washed with a 50% saturated aqueous solution of sodium hydrogencarbonate, water and then saturated saline, and dried over magnesium sulfate. After the solvent was distilled out under reduced pressure, the residue was purified by column chromatography on silica gel, thereby obtaining the intended compound (223) (8.2 g) as a solid product.

MH⁺=491

¹H-NMR (δ, CDCl₃):

1.24(3H,d;J=7.2 Hz), 3.09(3H,s), 4.09(1H,q;J=7.2 Hz), 4.27(1H,d;J=14.4 Hz), 4.91(1H,d;J=14.4 Hz), 5.78(1H,s), 6.78–6.85(2H,m), 7.47–7.55(1H,m), 7.67(1H,s), 7.69(1H,s), 7.87(1H,s), 8.02(2H,br-d:J=S.4 Hz), 8.10(2H,br-d:J=8.4 Hz).

Experimental Example 3:

Five-membered Groups of ICR mice were infected through their tail veins with a Candida albicans MCY8622 strain (2×10⁶ cfu/mouse). After 1 hour, the above compound (223) according to the present application was orally administered in a dose of 2.5 mg or 10 mg per kg of a mouse to the respective groups of mice. Observation was carried cut for 7 days to calculate the average number of surviving days in each group. This average number was used as an index indicative of antifungal activity in vivo.

[Result]

The result of the experiment is shown in the following Table 5.

TABLE 5

| Compound | Average number of surviving days (days) | |
|---|---|---|
| | 2.5 mg/kg | 10 mg/kg |
| 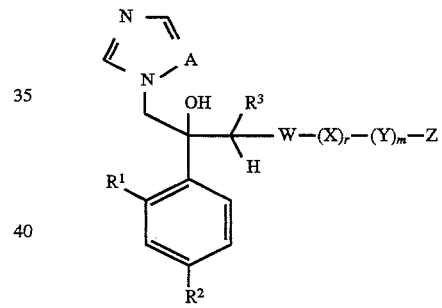 | 6.6 | 7.0 |

As apparent even from this result, the compounds prepared from the intermediates for synthesis by the preparation processes according to the present application exhibit excellent antifungal activity and are hence useful for the prophylaxis of and treatment for various mycotic infectious diseases.

What is claimed is:

1. A compound represented by the formula:

wherein $R^1$ and $R^2$ are identical with or different from each other and denote individually a halogen atom or hydrogen atom;

$R_3$ means a hydrogen atom or lower alkyl group;

r and m may be identical with or different from each other and stand individually for 0 or 1;

A is N;

W denotes thiazole, azabenzothiazole, 5-azabenzothiazole, 7-benzothiazole or oxazole;

X denotes a non-hetero aromatic ring, imidazole, triazole, tetrazole, pyridine or oxazole, each of which may have one or more substituent groups;

Y denotes a group represented by —S—, >SO, >SO₂, >C=S, >C=O, —O—, >N—R⁶, >CH—R⁶, >C=N—OR⁶ or —(CH₂)ⱼ—, in which R⁶ denotes a hydrogen atom or lower alkyl group, and j denotes an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenyl group which may have one or more substituent groups, phenoxy group which may have one or more substituent groups, pyridyl group which may have one or more substituent groups, imidazolyl group which may have one or more substituent groups, triazolyl group which may have one or more substituent groups, tetrazolyl group which may have one or more substituent groups, or amino group which may have one or more substituent groups, excluding compounds where R³ is a methyl group, and Z is a hydrogen atom, methyl group or trifluoro-methyl group when r=m=0, or a salt thereof.

2. Compounds separately having the structural formulae:

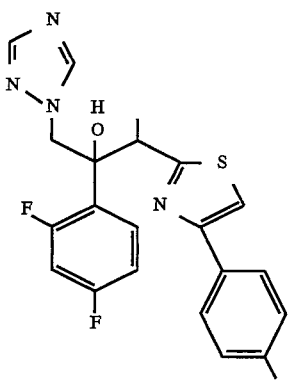

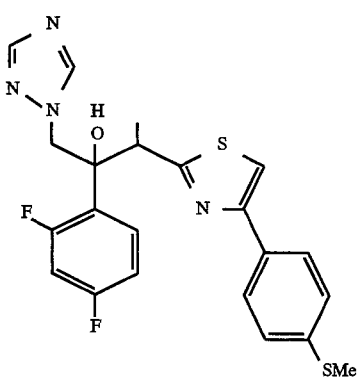

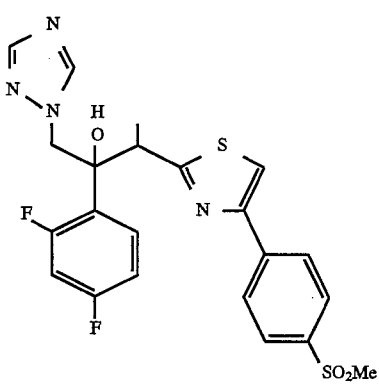

-continued

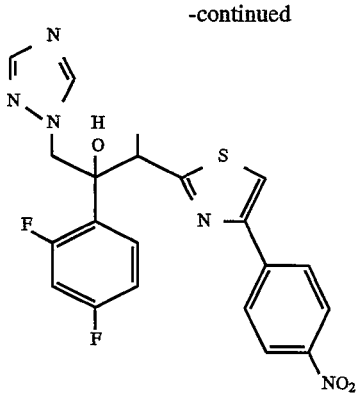

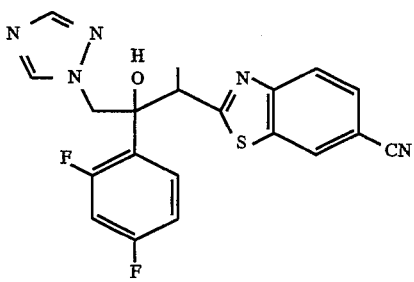

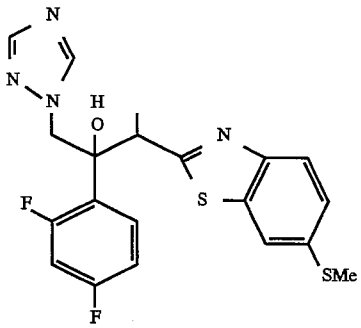

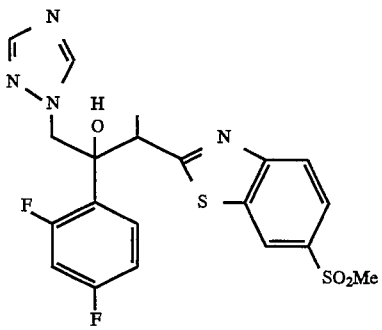

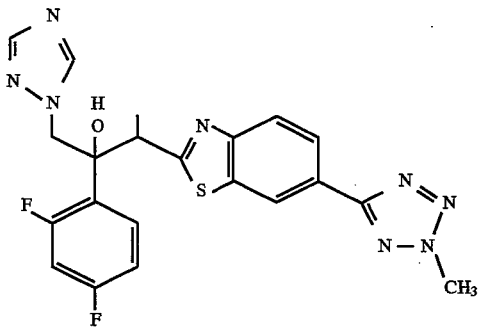

161

-continued

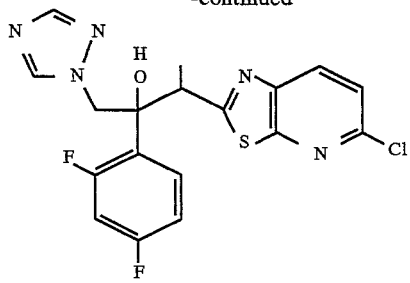

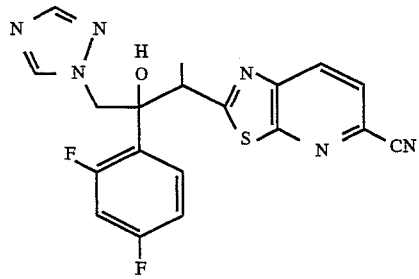

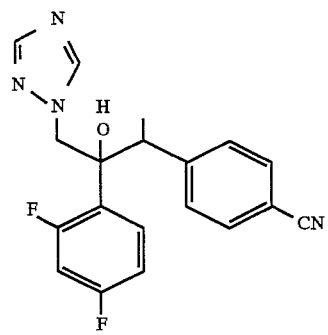

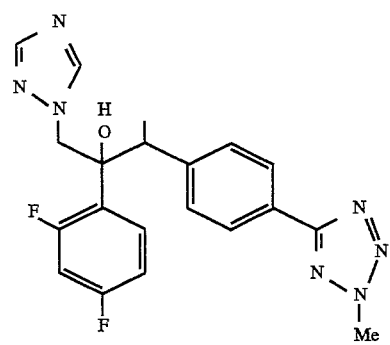

or acid-addition salts thereof.

3. A pharmaceutical composition comprising a compound represented by the formula:

162

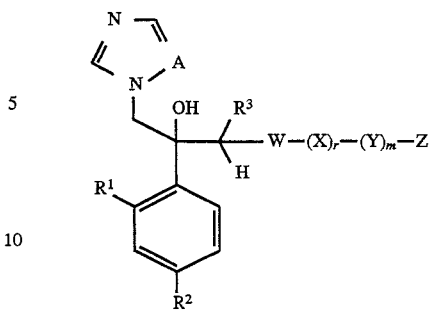

wherein $R^1$ and $R^2$ are identical with or different from each other and denote individually a halogen atom or hydrogen atom;

$R_3$ means a hydrogen atom or lower alkyl group;

r and m may be identical with or different from each other and stand individually for 0 or 1;

A is N;

W denotes thiazole, azabenzothiazole, 5-azabenzothiazole, 7-benzathiazole or oxazole;

X denotes a non-hetero aromatic ring, imidazole, triazole, tetrazole, pyridine or oxazole, each of which may have one or more substituent groups;

Y denotes a group represented by —S—, >SO, >SO$_2$, >C=S, >C=O, —O—, >N—R$^6$, >CH—R$^6$, >C=N—OR$^6$ or —(CH$_2$)$^J$—, in which R$^6$ denotes hydrogen atom or lower alkyl group, and J denotes an integer of 1–4; and Z denotes a hydrogen atom, halogen atom, lower alkyl group, halogenated lower alkyl group, lower alkoxy group, halogenated lower alkoxy group, hydroxyl group, thiol group, nitro group, cyano group, lower alkanoyl group, phenyl group which may have one or more substituent groups, phenoxy group which may have one or more substituent groups, pyridyl group which may have one or more substituent groups, imidazolyl group which may have one or more substituent groups, triazolyl group which may have one or more substituent groups, tetrazolyl group which may have one or more substituent groups, or amino group which may have one or more substituent groups, excluding compounds where $R^3$ is a methyl group, and Z is a hydrogen atom, methyl group or trifluoro-methyl group when r=m=0, or a pharmaceutically acceptable salt thereof and a carrier.

4. The pharmaceutical composition according to claim 3 which is suitable for use as an antifungal agent.

* * * * *

UNITED STATES PATENT AND TRADEMARK OFFICE
CERTIFICATE OF CORRECTION

| | |
|---|---|
| PATENT NO. : | 5,648,372 |
| DATED : | July 15, 1997 |
| INVENTOR(S) : | Toshihiko NAITO et al. |

It is certified that error appears in the above-identified patent and that said Letters Patent is hereby corrected as shown below:

Claim 1, line 10 (counting the formula as one line), change "azabenzothiazole" to --benzothiazole--; and
        line 11, change "7-benzothiazole" to --7-azabenzothiazole--.

Claim 3, line 11 (counting the formula as one line), change "azabenzothiazole" to --benzothiazole--; and
        line 12, change "7-benzothiazole" to --7-azabenzothiazole--.

Signed and Sealed this

Twenty-first Day of July, 1998

Attest:

Attesting Officer

BRUCE LEHMAN

Commissioner of Patents and Trademarks